US009500636B2

(12) United States Patent
Prindle et al.

(10) Patent No.: US 9,500,636 B2
(45) Date of Patent: Nov. 22, 2016

(54) MULTISCALE PLATFORM FOR COORDINATING CELLULAR ACTIVITY USING SYNTHETIC BIOLOGY

(71) Applicant: The Regents of the University of California, Oakland, CA (US)

(72) Inventors: Arthur Prindle, San Diego, CA (US); Phillip Samayoa, La Jolla, CA (US); Jeff Hasty, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 190 days.

(21) Appl. No.: 14/364,207

(22) PCT Filed: Dec. 14, 2012

(86) PCT No.: PCT/US2012/069914
§ 371 (c)(1),
(2) Date: Jun. 10, 2014

(87) PCT Pub. No.: WO2013/090818
PCT Pub. Date: Jun. 20, 2013

(65) Prior Publication Data
US 2015/0133339 A1    May 14, 2015

Related U.S. Application Data

(60) Provisional application No. 61/576,976, filed on Dec. 16, 2011.

(51) Int. Cl.
*G01N 33/18* (2006.01)
*C12Q 1/02* (2006.01)
(Continued)

(52) U.S. Cl.
CPC .......... *G01N 33/1866* (2013.01); *C12N 15/70* (2013.01); *C12Q 1/02* (2013.01); *C12Q 1/6897* (2013.01)

(58) Field of Classification Search
None
See application file for complete search history.

(56) References Cited

U.S. PATENT DOCUMENTS

2006/0057607 A1    3/2006  Lenz et al.

FOREIGN PATENT DOCUMENTS

WO    2013-090818    6/2013

OTHER PUBLICATIONS

Danino et al. (2010) "A synchronized quorum of genetic clocks" Nature 463(7279):326-330.*

(Continued)

*Primary Examiner* — Karen S Weiler
(74) *Attorney, Agent, or Firm* — Weaver Austin Villeneuve & Sampson LLP

(57) ABSTRACT

This invention provides a multiscale platform for coordinating behavior using synthetic biology. The platform reduces the impact of underlying noise, making outputs more coherent and reliable at the macroscopic level. In one aspect, the invention provides a frequency-modulated biosensor, comprising a microfluidic array comprising two or more separate colonies or populations of sensing cells to grow and communicate by gas exchange, wherein the colonies or populations of sensing cells output synchronized oscillating signals.

45 Claims, 19 Drawing Sheets

(51) Int. Cl.
*C12N 15/70* (2006.01)
*C12Q 1/68* (2006.01)

(56) References Cited

OTHER PUBLICATIONS

WO patent application No. PCT/US2012/069914, International Search Report and Written Opinion mailed Apr. 19, 2013.
WO patent application No. PCT/US2012/069914, International Preliminary Report on Patentability mailed Jun. 26, 2014.
Danino, Tal et al., "A synchronized quorum of genetic clocks," Nature; 463(7279): 326-330, Jan. 21, 2010.
Garcia-Ojalvo, Jordi et al., "Modeling a synthetic multicellular clock: Repressilators coupled by quorum sensing," PNAS, Jul. 27, 2004, vol. 101, No. 30, 10955-10960.
Prindle, Arthur et al., "Sensing array of radically coupled genetic biopixels," Nature; 481(7379): 39-44, Dec. 18, 2011.
Saeidi, Nazanin et al., "Engineering microbes to sense and eradicate *Pseudomonas aeruginosa*, a human pathogen," Molecular Systems Biology, vol. 7, No. 521, pp. 1-11, Aug. 16, 2011.

* cited by examiner

MULTISCALE PLATFORM FOR COORDINATING CELLULAR ACTIVITY USING SYNTHETIC BIOLOGY

CROSS-REFERENCE TO RELATED APPLICATIONS

This application is a U.S. national phase under 35 U.S.C. §371 of Intl. Appl. No. PCT/US2012/069914, filed on Dec. 14, 2012, which claims the benefit under 35 U.S.C. §119(e) of U.S. Provisional Application No. 61/576,976, filed on Dec. 16, 2011, which are hereby incorporated herein by reference in their entirety for all purposes.

STATEMENT OF GOVERNMENTAL SUPPORT

This invention was made with government support under Grant No. GM069811 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 10, 2014, is named UCSDP023_SL.txt and is 58,055 bytes in size.

FIELD OF THE INVENTION

The present invention relates to a multiscale platform for coordinating behavior using synthetic biology. The platform reduces the impact of underlying noise, making outputs more coherent and reliable at the macroscopic level.

BACKGROUND OF THE INVENTION

Synthetic biology can be broadly broken down into the 'top-down' synthesis of genomes (Gibson, et al., *Science* (2010) 329:52-56) and the 'bottom-up' engineering of relatively small genetic circuits (Hasty, et al., *Nature* (2001) 420:224-230 (2002); Sprinzak, et al., *Nature* 438:443-448 (2005); Endy, *Nature* (2005) 438:449-453; Ellis, et al., *Nature Biotechnol.* (2009) 27:465-471; Kobayashi, et al. *Proc. Natl Acad. Sci. USA* (2004) 101: 8414-8419; You, et al., *Nature* (2004) 428:868-871; Basu, et al., *Nature* (2005) 434:1130-1134; Mukherji, et al., *Nature Rev. Genet.* 10:859-871; Grilly, et al., *Mol. Syst. Biol.* (2007) 3:127). In the field of genetic circuits, toggle switches (Gardner, et al., *Nature* (2000) 403:339-342) and oscillators (Elowitz, et al., *Nature* (2000) 403, 335-338) have progressed into triggers (Lu, et al., *Proc. Natl Acad. Sci. USA* 104:11197-11202), counters (Friedland, et al., *Science* (2009) 324:1199-1202) and synchronized clocks (Danino, et al., *Nature* (2010) 463:326-330). Sensors have arisen as a major focus in the context of biotechnology (Kobayashi, et al. *Proc. Natl Acad. Sci. USA* (2004) 101: 8414-8419; Tamsir, et al., *Nature* (2011) 469: 212-215; Tabor, et al., *Cell* (2009) 137:1272-1281), while oscillators have provided insights into the basic-science functionality of cyclic regulatory processes (Stricker, et al., *Nature* (2008) 456:516-519; Mondragon-Palomino, et al., *Science* (2011) 333:1315-1319; Tigges, et al., *Nature* (2009) 457:309-312). A common theme is the concurrent development of mathematical modelling that can be used for experimental design and characterization, as in physics and the engineering disciplines.

The synchronization of genetic clocks provides a particularly attractive avenue for synthetic biology applications. Oscillations permeate science and technology in a number of disciplines, with familiar examples including alternating current (AC) power (U.S. Pat. No. 373,035), the global positioning system (GPS) (Lewandowski, et al., *Proc. IEEE* (1999) 87:163-172) and lasers (Vladimirov, et al., *Europhys. Lett.* (2003) 61:613). These technologies have demonstrated that operating in the frequency domain can offer considerable advantages over steady-state designs in terms of information gathering and transmission. In particular, oscillatory sensors confer a number of advantages to traditional ones (Gast, *J. Phys. E: Sci. Instrum.* (1985) 18:783), as frequency is easily digitized and can be quickly updated with repeated measurements. For sensors that use optical reporters, measurements of frequency are less sensitive to experimental factors such as beam power and exposure time than intensity measurements, which must be normalized and calibrated.

Although the bottom-up approach to synthetic biology is increasingly benefiting from DNA synthesis technologies, the general design principles are still evolving. In this context, a substantial challenge is the construction of robust circuits in a cellular environment that is governed by noisy processes such as random bursts of transcription and translation (Ozbudak, et al., *Nature Genet.* (2002) 31:69-73; Elowitz, et al., *Science* (2002) 297:1183-1186; Golding, et al., *Cell* (2005) 123:1025-1036; Blake, et al., *Mol. Cell* (2006) 24:853-865; Austin, et al. *Nature* (2006) 439:608-611). Such an environment leads to considerable intercellular variability in circuit behavior, which can impede coherent functionality at the colony level. An ideal design strategy for reducing variability across a cellular population would involve both strong and long-range coupling that would instantaneously synchronize the response of millions of cells. Quorum sensing typically involves strong intercellular coupling over tens of micrometers (Basu, et al., *Nature* (2005) 434:1130-1134; Danino, et al., *Nature* (2010) 463: 326-330; Waters, et al., *Annu. Rev. Cell Dev. Biol.* (2005) 21:319-346), yet the relatively slow diffusion time of molecular communication through cellular media leads to signalling delays over millimeter scales. Faster communication mechanisms, such as those mediated in the gas or vapor phase, may increase the length scale for instantaneous communication, but are comparatively weak and short lived because the vapor species more readily disperse.

SUMMARY OF THE INVENTION

In one aspect, the invention provides a frequency-modulated biosensor, comprising a microfluidic array comprising two or more separate colonies or populations of sensing cells to grow and communicate by gas exchange, wherein the colonies or populations of sensing cells output synchronized oscillating signals. In some embodiments, the colonies or populations of sensing cells are selected from the group consisting of microbial cells, bacterial cells, yeast cells, mammalian cells, insect cells, photosynthetic cells, and plant cells. In some embodiments, thousands of small oscillating cell colonies or populations are operatively coupled in a microfluidic array. In some embodiments, the degree to which neighboring colonies or populations are able to influence each other via fluid diffusion is negligible owing to the high media channel flow rates. In some embodiments, the colonies or populations of sensing cells output synchronized oscillations of approximately 2.5 million cells across a distance of about 5 mm. In some embodiments, the colonies or populations of sensing cells are in two or more devices that share no common fluid sources or channels. In some embodiments, the two or more devices comprise oxygen-permeable polydimethylsiloxane (PDMS) walls. In some embodiments, the colonies or populations of sensing cells are bacterial cells and the operative or intercellular coupling or communication of the cell colonies or populations involves redox signaling by hydrogen peroxide ($H_2O_2$). In some embodiments, the biosensor comprises a detector that detects oscillating bursts of $H_2O_2$ released from the colonies of cells. In some embodiments, the colonies or populations of sensing cells are bacterial cells and the synchronized oscillations are coordinated by hydrogen peroxide ($H_2O_2$). In some embodiments, the bacterial cells are E. coli cells. In some embodiments, the cells comprise a gene coding for NADH dehydrogenase II (ndh) under the control of a second lux promoter. In some embodiments, the cells comprise a gene coding for green fluorescent protein (GFP) under the control of a second lux promoter. In some embodiments, the cells comprise an of acyl-homoserine lactone (AHL) synthase LuxI, under the control of a native arsenite-responsive promoter that is repressed by ArsR in the absence of arsenite. In some embodiments, the cells comprise a luxR gene or an acyl-homoserine lactone (AHL) synthase LuxI gene controlled by an response element selected from the group consisting of an arsenite response element (pArsR), a cadmium response element (yodA/cadA/cadR), a copper response element (copA/cueR), a mercury response element (merR), a cobalt response element, a lead response element, a zinc response element, a cyanide response element (CNO), a microcystin response element (mlrABCD), and an organo-phosphorus (OP) neurotoxin response element.

In varying embodiments of the biosensor, the colonies or populations of cells (e.g., each, all or substantially all cells in a colony or population) comprise the following expression cassettes:
  i) a LuxR gene under the control of a response element promoter;
  ii) an aiiA gene under the control of a luxI promoter;
  iii) an acyl-homoserine lactone (AHL) synthase LuxI gene under the control of the luxI promoter; and
  iv) a nucleic acid encoding a protein that produces free radicals or oxygen reactive species (e.g., $H_2O_2$) under the control of the luxI promoter, wherein the colonies or populations of cells comprise a thresholding sensor that produces an oscillating signal in the presence of concentrations of an analyte above a threshold concentration, wherein the analyte binds to the response element promoter. In some embodiments, the colonies or populations of cells comprise a first expression cassette comprising at least 90% sequence identity, e.g., at least 91%, 92%, 93%, 94%, 95%, 96%, 97%, 98%, 99% or 100% sequence identity, to nucleic acid residues 27-756 of SEQ ID NO:1, a second expression cassette comprising at least 90% sequence identity, e.g., at least 91%, 92%, 93%, 94%, 95%, 96%, 97%, 98%, 99% or 100% sequence identity, to nucleic acid residues 901-1744 of SEQ ID NO:1, a third expression cassette comprising at least 90% sequence identity, e.g., at least 91%, 92%, 93%, 94%, 95%, 96%, 97%, 98%, 99% or 100% sequence identity, to nucleic acid residues 10-913 of SEQ ID NO:2, and a fourth expression cassette comprising at least 90% sequence identity, e.g., at least 91%, 92%, 93%, 94%, 95%, 96%, 97%, 98%, 99% or 100% sequence identity, to nucleic acid residues 7-1366 of SEQ ID NO:3. In some embodiments, the colonies or populations of cells comprise a first plasmid comprising at least 90% sequence identity, e.g., at least 91%, 92%, 93%, 94%, 95%, 96%, 97%, 98%, 99% or 100% sequence identity, to SEQ ID NO:1, a second plasmid comprising at least 90% sequence identity, e.g., at least 91%, 92%, 93%, 94%, 95%, 96%, 97%, 98%, 99% or 100% sequence identity, to SEQ ID NO:2, and a third plasmid comprising at least 90% sequence identity, e.g., at least 91%, 92%, 93%, 94%, 95%, 96%, 97%, 98%, 99% or 100% sequence identity, to SEQ ID NO:3.

In varying embodiments of the biosensor, the colonies or populations of cells comprise the following expression cassettes:
  i) an acyl-homoserine lactone (AHL) synthase LuxI gene under the control of a response element promoter;
  ii) a LuxR gene under the control of a luxR promoter and an aiiA gene under the control of a luxI promoter;
  iii) a LuxR gene under the control of a luxR promoter and a nucleic acid encoding a protein that produces free radicals or oxygen reactive species (e.g., $H_2O_2$) under the control of a luxI promoter; and
  iv) a LuxR gene under the control of a luxR promoter and a LuxI gene under the control of a luxI promoter, wherein the colonies or populations of cells comprise a period modulation sensor that produces a changed oscillating signal in the presence of concentrations of an analyte above a threshold concentration, wherein the analyte binds to the response element promoter. In some embodiments, the changed oscillating signal comprises increased oscillatory amplitude and period. In some embodiments, the colonies or populations of cells comprise a first expression cassette comprising at least 90% sequence identity, e.g., at least 91%, 92%, 93%, 94%, 95%, 96%, 97%, 98%, 99% or 100% sequence identity, to nucleic acid residues 7-1795 of SEQ ID NO:4, a second expression cassette comprising at least 90% sequence identity, e.g., at least 91%, 92%, 93%, 94%, 95%, 96%, 97%, 98%, 99% or 100% sequence identity, to nucleic acid residues 1895-3488 of SEQ ID NO:4, a third expression cassette comprising at least 90% sequence identity, e.g., at least 91%, 92%, 93%, 94%, 95%, 96%, 97%, 98%, 99% or 100% sequence identity, to nucleic acid residues 10-1771 of SEQ ID NO:5, and a fourth expression cassette comprising at least 90% sequence identity, e.g., at least 91%, 92%, 93%, 94%, 95%, 96%, 97%, 98%, 99% or 100% sequence identity, to nucleic acid residues 1-1203 of SEQ ID NO:6. In some embodiments, the colonies or populations of cells comprise a first plasmid comprising at least 90% sequence identity, e.g., at least 91%, 92%, 93%, 94%, 95%, 96%, 97%, 98%, 99% or 100% sequence identity, to SEQ ID NO:4, a second plasmid comprising at least 90% sequence identity, e.g., at least 91%, 92%, 93%, 94%, 95%, 96%, 97%, 98%, 99% or 100% sequence identity, to SEQ ID NO:5, and a third plasmid comprising at least 90% sequence identity, e.g., at least 91%, 92%, 93%, 94%, 95%, 96%, 97%, 98%, 99% or 100% sequence identity, to SEQ ID NO:6.

In varying embodiments of the biosensor, the expression cassettes are on one or multiple plasmids. In some embodiments, the response element promoter is selected from the group consisting of an arsenite response element (pArsR), a cadmium response element (yodA/cadA/cadR), a copper response element (copA/cueR), a mercury response element (merR), a cobalt response element, a lead response element, a zinc response element, a cyanide response element (CNO), a microcystin response element (mlrABCD), and an organo-phosphorus (OP) neurotoxin response element. In some embodiments, the nucleic acid encoding a detectable protein encodes a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the measurable output is detected optically. In some embodiments, the optical detection is selected from Luminescence, Fluorescence, and/or Colorimetry. In some embodiments, the measurable output is electrochemical. In some embodiments, the electrochemical detection is selected from Amperometric, Potentiometric, and/or Conductimetric signals. In some embodiments, the cellular biosensor is directly linked to an electronic system to convert the output. In some embodiments, the biosensor is a continuous monitoring system. In some embodiments, the microfluidic array comprises trapping chambers outside the flow of fluid for growing and housing the colonies of cells. In some embodiments, the trapping chambers are of a size of about 100× (80-100) $\mu m^2$. In some embodiments, the microfluidic array is 24 mm×12 mm and comprises over 12,000 communicating colonies of cells. In some embodiments, the microfluidic array comprises ports for infusing nutrient media and test compounds or solutions. In varying embodiments, the microfluidic array comprises a configuration as depicted in FIG. 3. In varying embodiments, the microfluidic array comprises multiple devices and comprises a configuration as depicted in FIG. 7. In some embodiments, the biosensor does not need to be calibrated. In some embodiments, the cells are in a fresh, frozen or dehydrated form. In some embodiments, the biosensor is implantable in a human. In some embodiments, cameras and/or microscopes and/or computers are used to monitor output. In some embodiments, wireless transmitters are used to monitor output.

In a related aspect, the invention comprises a kit comprising a biosensor as described herein.

In another aspect, the invention comprises methods of measuring and/or detecting the levels of an analyte, comprising contacting a test sample suspected of comprising the analyte with the biosensor as described herein, e.g., under conditions that allow the analyte to bind to a response element for the analyte, and measuring an oscillating signal output from the biosensor, thereby measuring the levels of the analyte. In some embodiments, the analyte is a small molecule. In some embodiments, the small molecule is selected from the group consisting of a small organic molecule, a small inorganic molecule, an element, a heavy metal, a peptide, a carbohydrate or a nucleic acid. In some embodiments, the analyte is selected from the group consisting of arsenic (arsenite), cadmium, copper, mercury, cobalt, lead, zinc, cyanide, a cyanobacterial microcystin, and an organophosphorus (OP) neurotoxin. In varying embodiments, the presence of the oscillating signal output indicates the detection of the analyte. In varying embodiments, the increased frequency and amplitude of the oscillating signal output indicates the detection of the analyte. In some embodiments, the test sample is blood, water or air.

In a related aspect, the invention is also directed to sets of expression cassettes, as described above and herein. The sets of expression cassettes, when expressed in a population of host cells (e.g., *E. coli*) produce colonies of cells that can communicate via gas or vapor phase and output synchronized oscillating signals. Further aspects include, plasmid, cells, colonies of cell and biosensors comprising the sets of expression cassettes, as described above and herein.

In one aspect, the invention provides methods of reducing background signal noise in biosensors and/or improving or augmenting biosensor signal detection. In some embodiments, the methods comprise synchronizing signaling from colonies or populations of reporter cells. In a further aspect, the invention provides methods comprising using frequency modulation as a mode of detection in biosensors. In various embodiments, the methods employ a biosensor as described herein. In some embodiments of the methods and biosensors, the cells are synchronized by production of a diffusible signal. In some embodiments, the signal is a redox reactant. In some embodiments, the redox reactant is $H_2O_2$. In some embodiments, the biosensor comprises microbial, mammalian, and/or photosynthetic cells. In some embodiments, the measurable output or reporter is a fluorescent probe. In some embodiments, the fluorescent probe is GFP. In some embodiments, the reporter is detected optically. In some embodiments, the optical detection is selected from Luminescence, Fluorescence, and/or Colorimetry. In some embodiments, the measurable output is electrochemical. In some embodiments, the electrochemical detection is selected from Amperometric, Potentiometric, and/or Conductimetric signals. In some embodiments, the cellular biosensor is directly linked to an electronic system to convert the output.

In a related aspect, the invention provides methods of assaying water quality, comprising synchronizing signaling from colonies or populations of reporter cells or using frequency modulation as a mode of detection in biosensors. In various embodiments, the methods employ a biosensor as described herein. In some embodiments, the levels of a heavy metal or a toxic metal (e.g., iron, manganese, aluminum, mercury, cadmium, beryllium, arsenic (arsenite), plutonium, lead, cadmium, chromium, cobalt, copper, manganese, nickel, tin, thallium, zinc) in water are determined. In some embodiments, the levels of one or more of arsenic (arsenite), cadmium, mercury, lead, and iron in the water are determined. In some embodiments, the water is potable water.

In a related aspect, the invention provides methods of assaying biomolecules, comprising synchronizing signaling from colonies or populations of reporter cells or using frequency modulation as a mode of detection in biosensors. In various embodiments, the methods employ a biosensor as described herein. In various embodiments, the analyte or biomolecule is selected from proteins, peptides (e.g., cytokines, hormones, antigens), carbohydrates, nucleic acids (e.g., DNA, RNA, micro RNA) and small organic compounds (e.g., metabolites, vitamins, hormones). In various embodiments, the levels of the biomolecules in a blood sample are assayed.

In another aspect, the invention provides methods of assaying small organic and/or inorganic compounds, comprising synchronizing signaling from colonies or populations of reporter cells or using frequency modulation as a mode of detection in biosensors. In various embodiments, the methods employ a biosensor as described herein. In some embodiments, the small organic and/or inorganic compounds are assayed in samples of water, blood or air.

In another aspect, the invention provides methods for spatial and temporal coordination of cellular behavior across two or more populations of cells utilizing a diffusible signal. In some embodiments, the diffusible signal is a vapor or a gas. In some embodiments, the diffusible signal is vapor phase $H_2O_2$. In some embodiments, the diffusible signal is a small molecule. In some embodiments, the small molecule is in a gas phase or a liquid phase. In some embodiments, the small molecule is selected from the group consisting of redox reactants, quorum sensing molecules, and cytokines. In some embodiments, the diffusible signal is produced internally by individual cells. In some embodiments, the diffusible signal is generated from a photosensitizer, mediated by external energy source. In some embodiments, the diffusible signal is introduced systematically across a population of cells. In some embodiments, the coordinated cellular behavior comprises natural phenotypes, synthetic phenotypes, and combinations thereof. In some embodiments, the phenotype of the coordinated cellular behavior is modulated by light signals. In some embodiments, the lines of spatial communication are directed by light cues. In some embodiments, the methods comprise coordinating cellular behavior of a cell selected from the group consisting of a microbial cell, a bacterial cell, a yeast cell, a mammalian cell, an insect cell, a photosynthetic cell, and a plant cell. In some embodiments, the cellular behavior is coordinated between cells in one or multiple devices. In some embodiments, the cells are set in one or multiple devices within a biofilm, microfluidic (2D/3D), or bioreactor culture. In some embodiments, the two or more populations of cells are used to produce synthetic drugs, biologics, and/or advanced biofuels. In some embodiments, the two or more populations of cells integrate a signal from a set of input stimuli. In some embodiments, the integrated signal is used as a diagnostic. In some embodiments, the integrated signal is a diagnostic indicator of a clinical pathology or environmental safety. In some embodiments, the two or more populations of cells direct stem cell differentiation.

With respect to practicing the various methods, in some embodiments, the biosensor is a continuous monitoring system. In some embodiments, the cells are housed in microscopic chambers. In some embodiments, the cells are in a fresh, frozen or dehydrated form. In some embodiments, the microscopic chambers are implantable in a human. In some embodiments, the microscopic chambers have ports for infusing nutrient media and test compounds or solutions. In some embodiments, the cells are in a fresh, frozen or dehydrated form. In some embodiments, the microscopic chambers are implantable in a human. In some embodiments, cameras and/or microscopes and/or computers are used to monitor reporting. In some embodiments, wireless transmitters are used to monitor reporting. In some embodiments, the cells are selected from the group consisting of a microbial cell, a bacterial cell, a yeast cell, a mammalian cell, an insect cell, a photosynthetic cell, and a plant cell.

DEFINITIONS

The term "response element" refers to sequences of DNA that are able to bind specific transcription factors or analytes and regulate transcription of genes.

The term "analyte" refers to any compound of agent of interest for detection. As appropriate, the analyte can be an element, a nucleic acid, a protein, a carbohydrate, a lipid or a small organic compound. The analyte can be organic or inorganic.

The terms "identical" or percent "identity," and variants thereof in the context of two or more polynucleotide sequences, refer to two or more sequences or subsequences that are the same. Sequences are "substantially identical" if they have a specified percentage of nucleic acid residues or nucleotides that are the same (e.g., at least 60% identity, optionally at least 65%, 70%, 75%, 80%, 85%, 91%, 92%, 93%, 94%, 95%, 96%, 97%, 98%, or 99% identity over a specified region (or the whole reference sequence when not specified)), when compared to a reference sequence (e.g., SEQ ID NOs: 1-6) and aligned for maximum correspondence over a comparison window, or designated region as measured using one of the following sequence comparison algorithms or by manual alignment and visual inspection. The present invention provides polynucleotides improved for expression in host cells that are substantially identical to the polynucleotides of described herein. Optionally, the identity exists over a region that is at least about 50 nucleic acid bases or residues in length, or more preferably over a region that is 100, 200, 300, 400, 500, 600, 800, 1000, 1500, 2000, 2500, 3000, or more, nucleic acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)). Examples of an algorithm that is suitable for determining percent sequence identity and sequence similarity include the BLAST suite using default parameters, available on the internet at blast.ncbi.nlm.nih.gov/, and known to those of skill in the art.

The term "substantial identity" of polynucleotide sequences means that a polynucleotide comprises a sequence that has at least 80% sequence identity, e.g., at least about 85%, 90%, 91%, 92%, 93%, 94%, 95%, 96%, 97%, 98%, 99%, or higher, compared to a reference sequence (e.g., SEQ ID NOs: 1-6), using sequence alignment/comparison algorithms set to standard parameters. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes means sequence identity of at least 80% sequence identity, e.g., at least about 85%, 90%, 91%, 92%, 93%, 94%, 95%, 96%, 97%, 98%, 99%, or higher, using sequence alignment/comparison algorithms set to standard parameters. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asp artic acid-glutamic acid, and asparagine-glutamine. Determination of "substantial identity" can be focused over defined subsequences, such as known structural domains.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 1 molar at pH 7 and the temperature is at least about 60° C.

An "expression cassette" refers to a nucleic acid construct, which when introduced into a host cell, results in transcription and/or translation of a RNA or polypeptide, respectively.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as a nucleic acid encoding an antigen, wherein the expression control sequence directs transcription of the nucleic acid corresponding to the second sequence. The promoters used in the present expression cassettes are active in the host cells, but need not originate from that organism. It is understood that limited modifications can be made without destroying the biological function of a regulatory element and that such limited modifications can result in regulatory elements that have substantially equivalent or enhanced function as compared to a wild type regulatory element. These modifications can be deliberate, as through site-directed mutagenesis, or can be accidental such as through mutation in hosts harboring the regulatory element. All such modified nucleotide sequences are included in the definition of a regulatory element as long as the ability to confer expression in the host cell is substantially retained.

DETAILED DESCRIPTION

1. Introduction

Although there has been considerable progress in the development of engineering principles for synthetic biology, a substantial challenge is the construction of robust circuits in a noisy cellular environment. Such an environment leads to considerable intercellular variability in circuit behavior, which can hinder functionality at the colony level. Here, we engineered the synchronization of thousands of oscillating colony 'biopixels' over centimeter-length scales through the use of synergistic intercellular coupling involving quorum sensing within a colony and gas-phase redox signalling between colonies. We used this platform to construct a liquid crystal display (LCD)-like macroscopic clock that can be used to sense an analyte of interest (e.g., biomolecules, small organic and/or inorganic compounds, heavy metals, e.g., arsenic (arsenite), cadmium, mercury, lead) via modulation of the oscillatory period. Given the repertoire of sensing capabilities of bacteria such as Escherichia coli, the ability to coordinate their behavior over large length scales sets the stage for the construction of low cost genetic biosensors that are capable of detecting an analyte of interest (e.g., heavy metals and pathogens) in the field.

Figure 11:
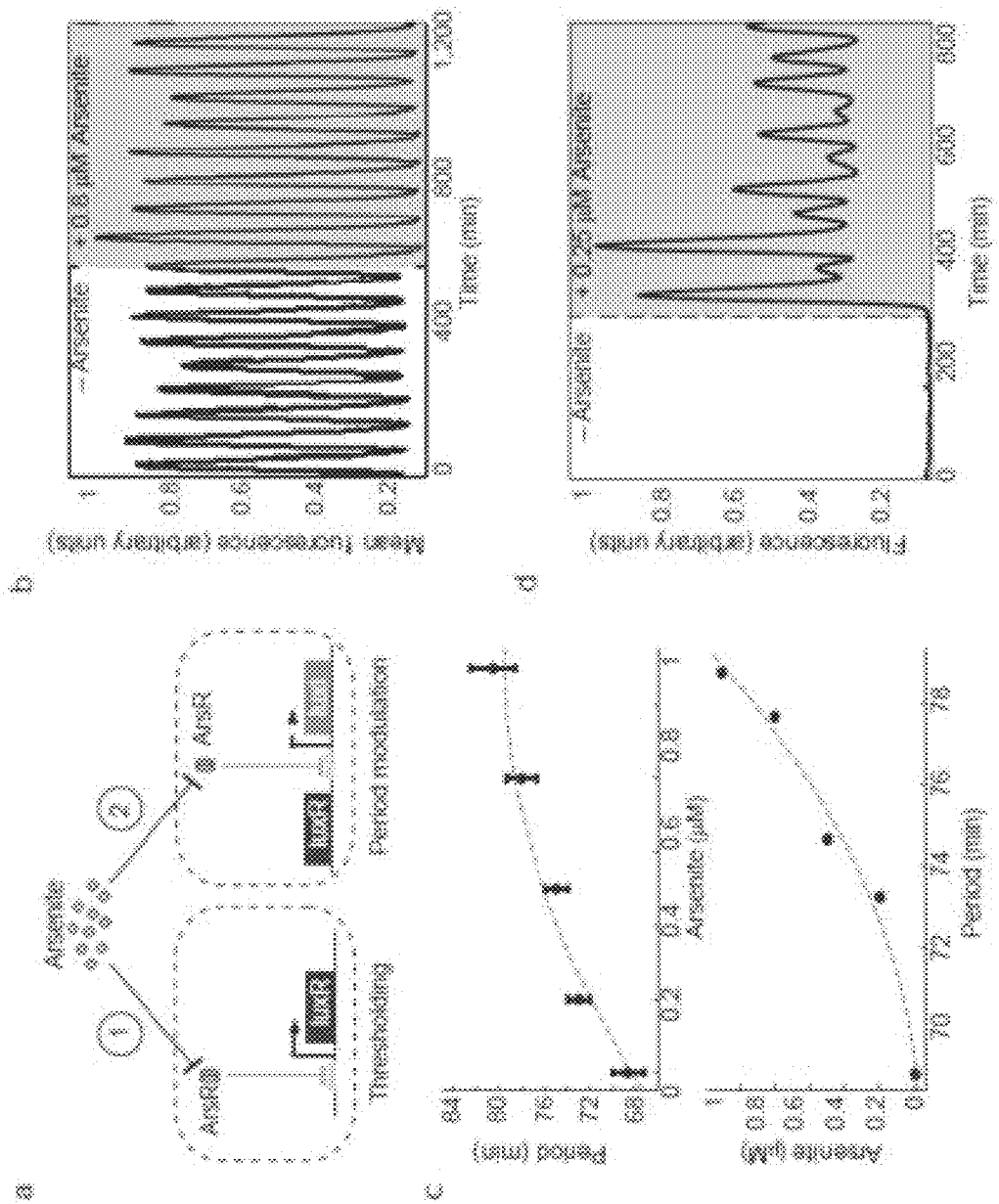
FIGS. 11A-D illustrate a frequency-modulated genetic biosensor. a, Network diagrams depicting two constructed sensing modules. In thresholding (1), the luxR gene is removed from the oscillator network and supplemented by a new copy driven by an arsenite-responsive promoter. In period modulation (2), a supplementary luxI gene tagged for increased degradation is driven by the arsenic-responsive promoter, which affects the period of oscillation. b, A sample period modulation sensor output following a step increase of 0.8 mM arsenite. Oscillatory period increases from 69 min to 79 min. c, Top, period versus arsenite concentration for the sensor array. Error bars indicate 6 1 standard deviation averaged over 500 biopixel trajectories. Dotted line represents model-predicted curve. Bottom, sensor calibration curve generated from experimental data. Points indicate the maximum arsenite level with 95% certainty for a given measured period as determined statistically from experimental data. d, Thresholder output following a step increase of 0.25 mM arsenite. A marked shift from rest to oscillatory behavior is observed within 20 min after the addition of arsenite.
Figure 12:
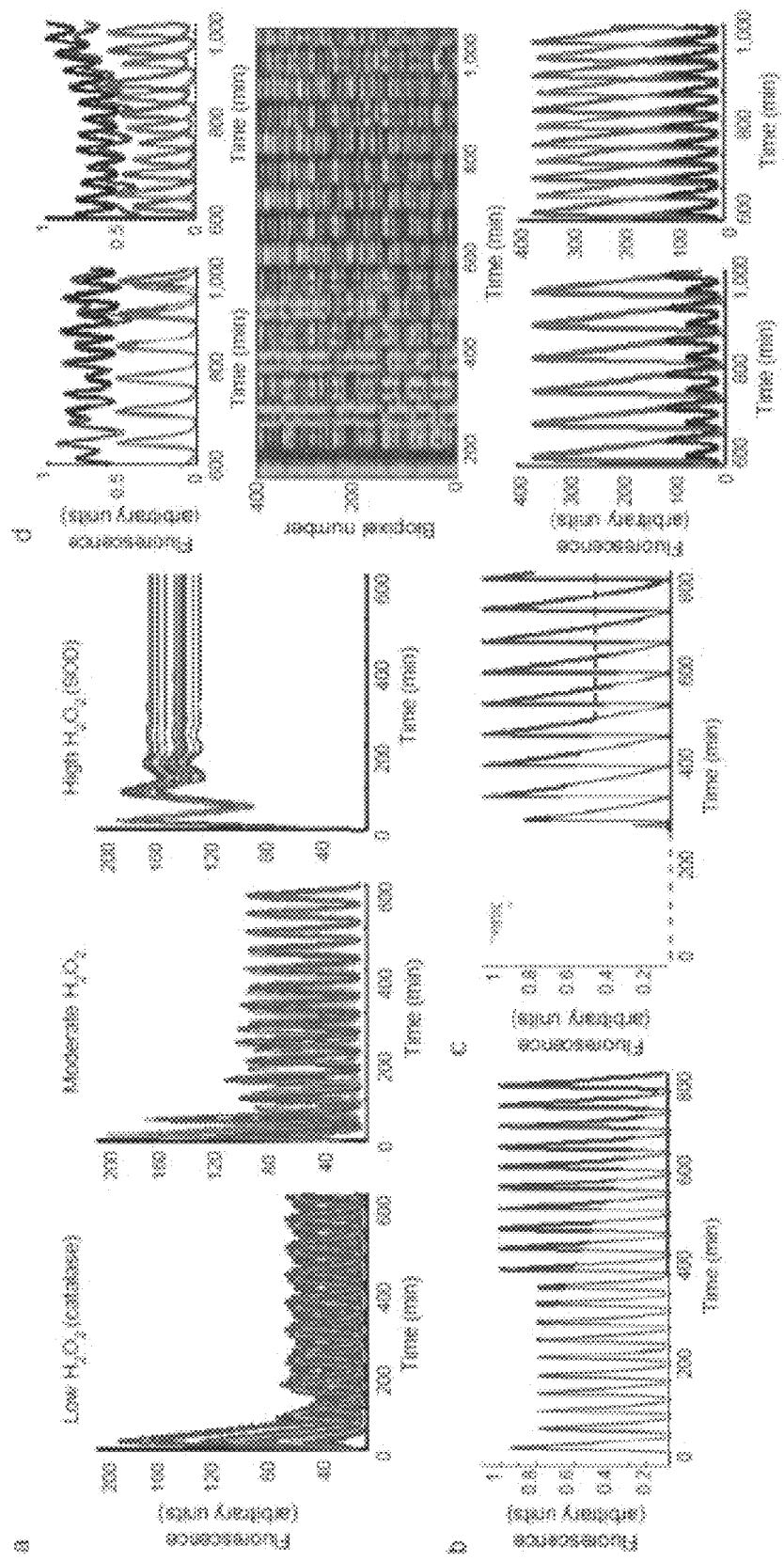
FIGS. 12A-D illustrate computational modelling of radical synchronization and biosensing. a, Time series of a population of biopixels producing varying amounts of $H_2O_2$ vapor. Synchronization occurs only for moderate levels whereas high levels lock ON and low levels oscillate asynchronously. b, A typical time series for our period modulation sensor undergoing a step increase of arsenite. Oscillations increase in both amplitude and period. c, A typical time series output for the thresholding sensor. Oscillations arise after the addition of arsenite. d, Experimental and computational output depicting complex dynamic behaviors between neighboring traps. Top, 1:2 resonance and antiphase synchronization observed when trap size (left, black/blue 5.95 mm depth and red/magenta 5.85 mm depth) and separation distance (right, same colors) are modified experimentally. Middle, scaled-up array experimental data for increased trap separation experiments demonstrating antiphase synchronization. Bottom, computational model trajectories depicting 1:2 resonance and anti-phase synchronization when trap size (same colors as experimental data) and separation distance are changed.

Our model of the frequency-modulated biosensor is based on a previously described model for the quorum-sensing synchronized oscillator (Danino, et al., Nature (2010) 463: 326-330). In addition to the reactions reflected in that model, we include the arsenite-induced production and degradation of LuxI and/or LuxR. From the biochemical reactions, we derived a set of delay differential equations to be used as our model. These delayed reactions mimic the complex cascade of processes (transcription, translation, maturation, etc.) leading to formation of functional proteins. As expected, our model predicts oscillations that change frequency when changes in arsenite occur (FIGS. 11c and 12b). The amplitude and period of the oscillations both depend on the concentrations of the toxin. We then modified the model to describe the LuxR-based detection system. Our model predicts a marked transition from rest to oscillations upon addition of arsenite, consistent with experimental observations (FIG. 12c).

Figure 16:
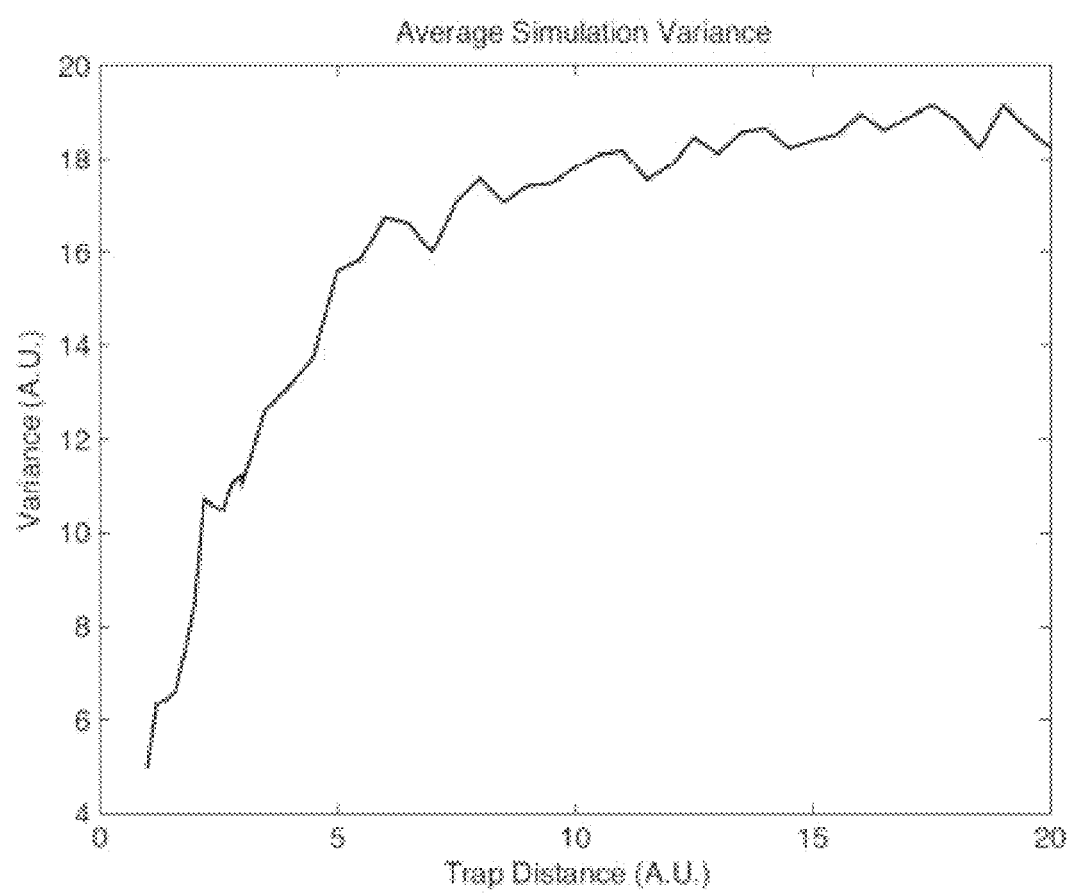
FIG. 16 illustrates computational results depicting biopixel synchronicity as a function of trap separation distance. As biopixels are moved farther apart, the entropy increases due to decreased effective migration of $H_2O_2$ between colonies.
Figure 17:
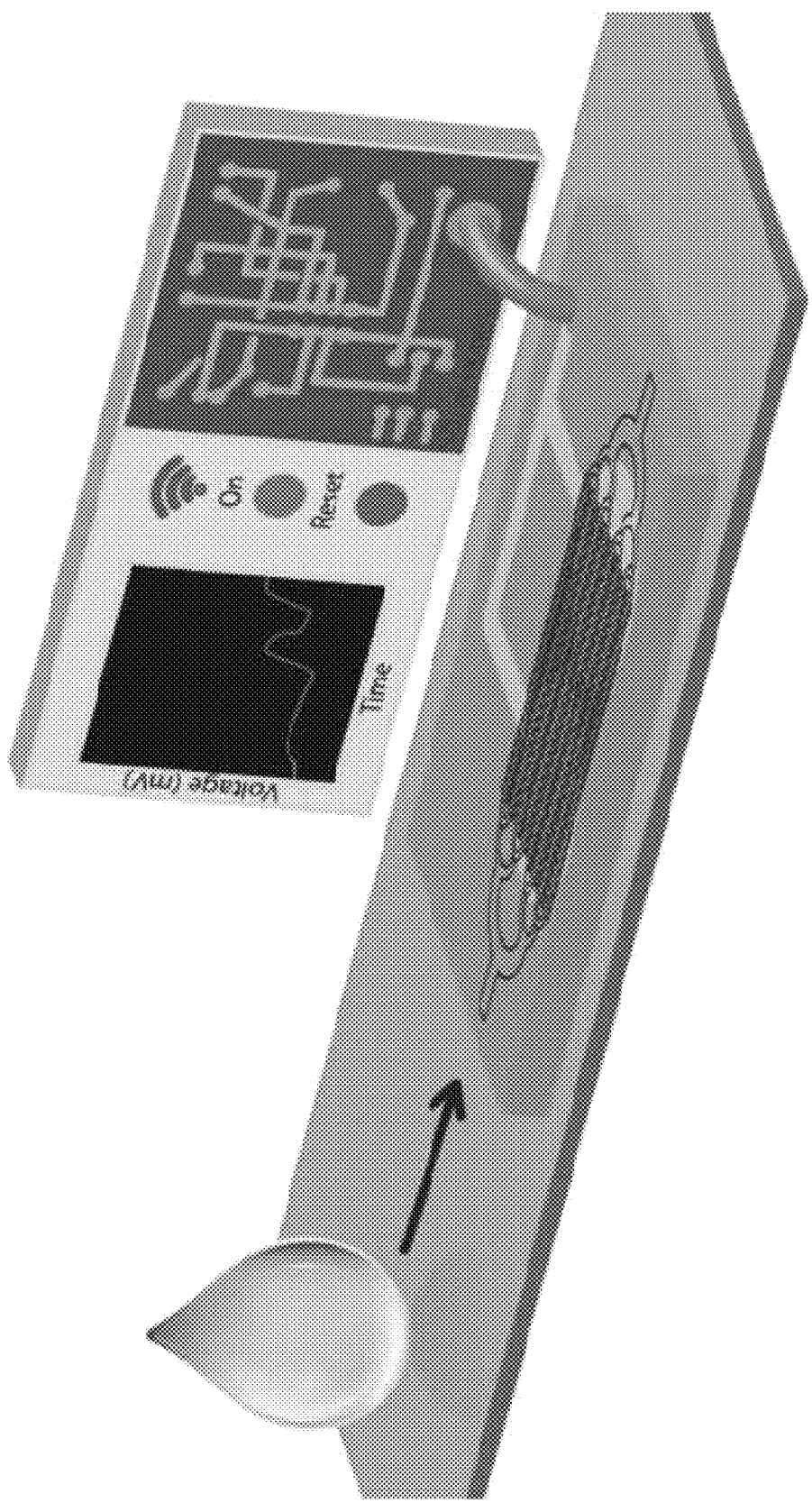
FIG. 17 illustrates a biosensor on a microscope slide connected to an output detection device.

The multi-scale nature of communication in our array allows us to treat colony and array-level dynamics separately; in the latter, arsenite affects the quorum-sensing machinery of a colony, producing changes to oscillatory period that propagate between biopixels in the array. To describe quantitatively the mechanisms driving synchronization at the array level, we treat each colony as a single oscillator that acts according to degrade-and-fire kinetics (Mather, et al., *Phys. Rev. Lett.* (2009) 102:068105). We also include the production of $H_2O_2$ and its interaction with neighboring colonies by two-dimensional diffusion. Using this model we identified three regimes that correlate well with experimental observations (FIG. 12a). When the effective production of $H_2O_2$ is low, as with catalase, we observe unsynchronized oscillations owing to constant, mild repression of the lux promoter via ArcAB (FIG. 12a, left). In contrast, when $H_2O_2$ production is very high, neighboring colonies rapidly fire in succession and remain on because of the permanent activation of the lux promoter, consistent with the SOD experiment (FIG. 12a, right). Finally, at intermediate $H_2O_2$, we observe globally synchronized oscillations (FIG. 12a, middle). As colonies are moved further apart, synchronicity breaks owing to slowed migration of $H_2O_2$ (FIG. 16).

The present oscillating biosensors can coordinate more cells faster and over greater length scales than quorum sensing. Cell-cell communication solely by quorum sensing cannot coordinate isolated colonies. Quorum sensing is slower and operates on shorter distances than the present methods and biosensors. The present oscillating biosensors can coordinate between isolated colonies by gas-phase communication. Whereas quorum sensing coordinates cells locally, redox signaling, described herein, coordinates over long distances between colonies. These properties allow one to precisely and synergistically synchronize the behavior of millions of cells.

Advantages of biosensors include specicity, low cost, ease of use, and portability. However, currently available field kits for arsenic cannot accurately measure concentrations at low enough concentrations, and they are also prone to false negative results (Rahman, et al., *Environ. Sci. Technol*, (2002) 36(24), 5385-5394). Conventional methods for heavy metal detection, on the other hand, are precise but suffer from the disadvantages of high cost and lack of portability.

Most existing biosensors rely on direct induction; that is, a reporter is directly produced in response to a toxin of interest, in a graded fashion proportional to concentration. A significant limitation of this approach is that induction curves require precise calibration to ensure proper correlation between input and output. In order to avoid false positives and accurately measure absolute concentration, calibration is required, making it difficult to obtain consistent results from day-to-day or even sample-to-sample. Any sensor that will be ultimately used in a field-ready system must be robust to variations in experimental technique and environmental circumstances. A related problem involves the control of the microbial population size. The ability to regulate and maintain a particular size of cell colony is important not only for calibration purposed but also for safety.

Our approach benefits from the use of a periodic output, with frequency correlated with input concentration. The use of a blinking frequency avoids the calibration problem. Another advantage is the use of regulated killing to maintain a constant population size, which will allow for extended usage and reliability. Finally, the ability to expand our technology to two or more specific inputs is a major advantage over existing solutions. Furthermore, the frequency modulated biosensor design is adaptable, specific, and sensitive, and computational techniques allow for the precise deduction of the input concentrations base on the components of the output signal. For these reasons, the frequency modulated biosensors described herein offer significant improvements over existing technologies.

2. Cells

The biosensors comprise colonies of cells capable of expressing the proteins encoded in the expression cassettes described herein, non-fluid (e.g., vapor phase) communication and producing oscillating output signals. In varying embodiments of the biosensors, the colonies of cells are substantially genetically identical, e.g., are of the same species and/or of the same strain. In varying embodiments, the colonies of host cells are microbial cells, bacterial cells, yeast cells, mammalian cells, insect cells, photosynthetic cells, or plant cells. In some embodiments, the colonies of cells are bacterial cells, e.g., *E. coli* cells.

3. Expression Cassettes

The synchronized oscillator design is based on elements of the quorum sensing machineries in *Vibrio fisheri* and *Bacillus Thurigensis*. We placed the luxI gene (from *V. fischeri*), aiiA gene (from *B. Thurigensis*) and a fluorescent protein gene (e.g., yemGFP) under the control of three identical copies of the luxI promoter. The LuxI synthase enzymatically produces an acyl-homoserine lactone (AHL), which is a small molecule that can diffuse across the cell membrane and mediates intercellular coupling. It binds intracellularly to the constitutively produced LuxR, and the LuxR-AHL complex is a transcriptional activator for the luxI promoter (Waters and Bassler, *Annu Rev Cell Dev Biol*. (2005) 21:319-46). AiiA negatively regulates the promoter by catalyzing the degradation of AHL (Liu et al., *Biochemistry*, (2008) 47(29):7706-7714).

Most quorum sensing systems require a critical cell density for generation of coordinated behavior (Reading and Sperandio, *FEMS microbiology letters*, (2006) 254(1):1-11). We modified the local cell density of the synchronized oscillator cells (denoted TDQS1) through the use of microfluidic devices (Cookson et al., *Mol. Syst. Biol.*, (2006) 1, msb4100032-E1-6) of differing geometries. The device used for monitoring the bulk oscillations comprises a main nutrient-delivery channel that feeds a rectangular trapping chamber. Once seeded, a monolayer of *E. coli* cells grow in the chamber and are eventually pushed into the channel where they then flow to the waste port. The biosensor devices described herein allow for a constant supply of nutrients or inducers and the maintenance of an exponentially growing colony of cells for more than four days. We found that chamber sizes of $100\times(80\text{-}100)$ $\mu m^2$ are useful for monitoring the intercellular oscillator, because such chamber sizes allowed for sufficient nutrient distribution and increased cell and AHL densities. In the context of the design parameters, the flow rate can be modulated in order to change the local concentration of AHL.

After an initial transient period, the synchronized oscillator cells exhibit stable synchronized oscillations which are easily discernible at the colony level. The dynamics of the oscillations can be understood as follows. Since AHL is swept away by the fluid flow and is degraded by AiiA internally, a small colony of individual cells cannot produce enough inducer to activate expression from the luxI promoter. However, once the population reaches a critical density, there is a "burst" of transcription of the luxI promoters, resulting in increased levels of LuxI, AiiA, and GFP. As AiiA accumulates, it begins to degrade AHL, and after a sufficient time, the promoters return to their inactivated state. The production of AiiA is then attenuated, which permits another round of AHL accumulation and another burst of the promoters.

The colonies of cells in the biosensors comprise multiple expression cassettes, e.g., contained on one or multiple plasmids, or incorporated into the host cells's genome that allow for the production of an oscillating output signal in the presence of an analyte of interest above above a threshold or detection level. The expression cassettes expressed by the colonies of host cells in the biosensors will vary depending on whether one or multiple analytes are being detected, and whether signal output is turned on or changes in the presence of detectable analyte or analyte concentrations above the threshold concentration.

In varying embodiments, one or more of the expression cassettes comprise one or more arcA binding sites positioned within about 150 bp, e.g., within about 140 bp, 130 bp, 120 bp, 115 bp, 110 bp, 100 bp, 95 bp, 90 bp, 85 bp, 80 bp, 75 bp, 70 bp, 65 bp, 60 bp, 55 bp, 50 bp, 45 bp, 40 bp, 35 bp, 30 bp, 25 bp, 20 bp, 15 bp, 10 bp, or 5 bp of a target gene or abutted to a target gene, e.g., a LuxR gene, a LuxI gene, and/or a nucleic acid encoding a protein that produces free radicals or oxygen reactive species (e.g., a fluorescent protein, e.g., GFP, YFP, CFP, rs-GFP, miniSOG). In varying embodiments, the one or more ArcA or ArcAB binding sites are positioned upstream or 5' and within about 150 bp, e.g., within about 140 bp, 130 bp, 120 bp, 115 bp, 110 bp, 100 bp, 95 bp, 90 bp, 85 bp, 80 bp, 75 bp, 70 bp, 65 bp, 60 bp, 55 bp, 50 bp, 45 bp, 40 bp, 35 bp, 30 bp, 25 bp, 20 bp, 15 bp, 10 bp, or 5 bp of the target gene or abutted to the target gene An arcA site binds arcA, which is released by arcB in the presence of oxidative conditions ($H_2O_2$). As used herein, an arcA binding site is about 15-20 bp in length, e.g., about 15 bp, 16 bp, 17 bp, 18 bp, 19 bp or 20 bp in length, and comprises a nucleic acid sequence having substantial sequence identity, e.g., at least 90%, 91%, 92%, 93%, 94%, 95%, 96%, 97%, 98%, 99% or 100% sequence identity, to the nucleic acid sequence CAATTACTTAACATAAGC (SEQ ID NO:9).

Generally, with respect to different embodiments and designs of the biosensors, the expression cassettes are on one or multiple plasmids, e.g., 1, 2, 3, 4, or more plasmids. In varying embodiments of the threshold biosensors, the expression cassettes are incorporated into the genome of the host cells.

In varying embodiments of the biosensors, the response element promoter is selected from the group consisting of an arsenite response element (pArsR), a cadmium response element (yodA/cadA/cadR), a copper response element (copA/cueR), a mercury response element (merR), a cobalt response element, a lead response element, a zinc response element, a cyanide response element (CNO), a microcystin response element (mlrABCD), and an organophosphorus (OP) neurotoxin response element. For example, in varying embodiments, the arsenite response element (pArsR) or cadmium response element used in the illustrative examples can be replaced with another response element known in the art for detecting an analyte of interest, including the above listed response elements for detecting heavy metals and toxins. Response elements for detecting hormones and vitamins are also known in the art.

In varying embodiments, of the threshold sensor, the nucleic acid encoding a protein that produces free radicals or oxygen reactive species (e.g., $H_2O_2$) encodes a fluorescent protein. Fluorescent proteins and their coding sequences are known in the art. Illustrative fluorescent proteins include, e.g., a green fluorescent protein, a yellow fluorescent protein, a cyan fluorescent protein, a red-shifted green fluorescent protein (rs-GFP), and miniSOG.

Threshold Biosensors

In one embodiment, the colonies of cells comprise expression cassettes designed to produce a threshold biosensor. Under this design, synchronized oscillating output signals are produced in the presence of analyte above a threshold concentration or above a concentration detected by the response element. In a particular embodiment, colonies of cells in a threshold biosensor comprise the following expression cassettes:

i) a LuxR gene under the control of a response element promoter;

ii) an aiiA gene under the control of a luxI promoter;

iii) an acyl-homoserine lactone (AHL) synthase LuxI gene under the control of the luxI promoter; and iv) a nucleic acid encoding a protein that produces free radicals or oxygen reactive species (e.g., $H_2O_2$) under the control of the luxI promoter, wherein the colonies of cells comprise a threshold sensor that produces an oscillating signal in the presence of concentrations of an analyte above a threshold concentration, wherein the analyte binds to the response element promoter.

In varying embodiments of the threshold biosensors, the colonies of cells comprise a set of expression cassettes comprising:

i) a LuxR gene under the control of an arsenite response element (pArsR);

ii) an aiiA gene under the control of a luxI promoter;

iii) an acyl-homoserine lactone (AHL) synthase LuxI gene under the control of the luxI promoter; and iv) a nucleic acid encoding a protein that produces free radicals or oxygen reactive species under the control of the luxI promoter, wherein the biosensor detects arsenic.

In varying embodiments of the threshold biosensors, the colonies of cells comprise a set of expression cassettes comprising:

i) a LuxR gene under the control of a cadmium response element (yodA/cadA/cadR);

ii) an aiiA gene under the control of a luxI promoter;

iii) an acyl-homoserine lactone (AHL) synthase LuxI gene under the control of the luxI promoter; and iv) a nucleic acid encoding a protein that produces free radicals or oxygen reactive species under the control of the luxI promoter, wherein the biosensor detects cadmium.

In varying embodiments of the threshold biosensors, the colonies of cells comprise a set of expression cassettes comprising:

i) a LuxR gene under the control of an arsenite response element (pArsR);

ii) a LuxR gene under the control of a cadmium response element (yodA/cadA/cadR);

iii) an aiiA gene under the control of a luxI promoter;

iv) an acyl-homoserine lactone (AHL) synthase LuxI gene under the control of the luxI promoter; and v) a nucleic acid encoding a protein that produces free radicals or oxygen reactive species under the control of the luxI promoter, wherein the biosensor detects cadmium and arsenic.

In varying embodiments of the threshold biosensors, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 27-756 of SEQ ID NO:1, a second expression cassette comprising at least 90% sequence identity, e.g., at least 91%, 92%, 93%, 94%, 95%, 96%, 97%, 98%, 99% or 100% sequence identity, to nucleic acid residues 901-1744 of SEQ ID NO:1, a third expression cassette comprising at least 90% sequence identity, e.g., at least 91%, 92%, 93%, 94%, 95%, 96%, 97%, 98%, 99% or 100% sequence identity, to nucleic acid residues 10-913 of SEQ ID NO:2, and a fourth expression cassette comprising at least 90% sequence identity, e.g., at least 91%, 92%, 93%, 94%, 95%, 96%, 97%, 98%, 99% or 100% sequence identity, to nucleic acid residues 7-1366 of SEQ ID NO:3, wherein the biosensor detects arsenic.

In varying embodiments of the threshold biosensors, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:1, a second plasmid comprising at least 90% sequence identity, e.g., at least 91%, 92%, 93%, 94%, 95%, 96%, 97%, 98%, 99% or 100% sequence identity, to SEQ ID NO:2, and a third plasmid comprising at least 90% sequence identity, e.g., at least 91%, 92%, 93%, 94%, 95%, 96%, 97%, 98%, 99% or 100% sequence identity, to SEQ ID NO:3, wherein the biosensor detect arsenic.

In varying embodiments of the threshold biosensors, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 27-756 of SEQ ID NO:1, a second expression cassette comprising at least 90% sequence identity, e.g., at least 91%, 92%, 93%, 94%, 95%, 96%, 97%, 98%, 99% or 100% sequence identity, to nucleic acid residues 901-1744 of SEQ ID NO:1, a third expression cassette comprising at least 90% sequence identity, e.g., at least 91%, 92%, 93%, 94%, 95%, 96%, 97%, 98%, 99% or 100% sequence identity, to nucleic acid residues 10-913 of SEQ ID NO:2, and a fourth expression cassette comprising at least 90% sequence identity, e.g., at least 91%, 92%, 93%, 94%, 95%, 96%, 97%, 98%, 99% or 100% sequence identity, to nucleic acid residues 7-788 of SEQ ID NO:7, wherein the biosensor detects cadmium.

In varying embodiments of the threshold biosensors, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:1, a second plasmid comprising at least 90% sequence identity, e.g., at least 91%, 92%, 93%, 94%, 95%, 96%, 97%, 98%, 99% or 100% sequence identity, to SEQ ID NO:2, and a third plasmid comprising at least 90% sequence identity, e.g., at least 91%, 92%, 93%, 94%, 95%, 96%, 97%, 98%, 99% or 100% sequence identity, to SEQ ID NO:7, wherein the biosensor detects cadmium.

In varying embodiments of the threshold biosensors, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 27-756 of SEQ ID NO:1, a second expression cassette comprising at least 90% sequence identity, e.g., at least 91%, 92%, 93%, 94%, 95%, 96%, 97%, 98%, 99% or 100% sequence identity, to nucleic acid residues 901-1744 of SEQ ID NO:1, a third expression cassette comprising at least 90% sequence identity, e.g., at least 91%, 92%, 93%, 94%, 95%, 96%, 97%, 98%, 99% or 100% sequence identity, to nucleic acid residues 10-913 of SEQ ID NO:2, and a fourth expression cassette comprising at least 90% sequence identity, e.g., at least 91%, 92%, 93%, 94%, 95%, 96%, 97%, 98%, 99% or 100% sequence identity, to nucleic acid residues 7-790 of SEQ ID NO:8, wherein the biosensor detects cadmium, zinc and mercury.

In varying embodiments of the threshold biosensors, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:1, a second plasmid comprising at least 90% sequence identity, e.g., at least 91%, 92%, 93%, 94%, 95%, 96%, 97%, 98%, 99% or 100% sequence identity, to SEQ ID NO:2, and a third plasmid comprising at least 90% sequence identity, e.g., at least 91%, 92%, 93%, 94%, 95%, 96%, 97%, 98%, 99% or 100% sequence identity, to SEQ ID NO:8, wherein the biosensor detects cadmium, zinc and mercury.

In varying embodiments of the threshold biosensors, the colonies of cells comprise a first expression cassette comprising at least 90% sequence identity to nucleic acid residues 27-756 of SEQ ID NO:1, a second expression cassette comprising at least 90% sequence identity to nucleic acid residues 901-1744 of SEQ ID NO:1, a third expression cassette comprising at least 90% sequence identity to nucleic acid residues 10 913 of SEQ ID NO:2, a fourth expression cassette comprising at least 90% sequence identity to nucleic acid residues 7-1366 of SEQ ID NO:3, and a fifth expression cassette comprising at least 90% sequence identity to nucleic acid residues 7-788 of SEQ ID NO:7, wherein the biosensor detects arsenic and cadmium.

In varying embodiments of the threshold biosensors, the colonies of cells comprise a first plasmid comprising at least 90% sequence identity to SEQ ID NO:1, a second plasmid comprising at least 90% sequence identity to SEQ ID NO:2, a third plasmid comprising at least 90% sequence identity to SEQ ID NO:3, and a fourth plasmid comprising at least 90% sequence identity to SEQ ID NO:7, wherein the biosensor detects arsenic and cadmium.

In varying embodiments of the threshold biosensors, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 27-756 of SEQ ID NO:1, a second expression cassette comprising at least 90% sequence identity, e.g., at least 91%, 92%, 93%, 94%, 95%, 96%, 97%, 98%, 99% or 100% sequence identity, to nucleic acid residues 901-1744 of SEQ ID NO:1, a third expression cassette comprising at least 90% sequence identity, e.g., at least 91%, 92%, 93%, 94%, 95%, 96%, 97%, 98%, 99% or 100% sequence identity, to nucleic acid residues 10-913 of SEQ ID NO:2, a fourth expression cassette comprising at least 90% sequence identity, e.g., at least 91%, 92%, 93%, 94%, 95%, 96%, 97%, 98%, 99% or 100% sequence identity, to nucleic acid residues 7-1366 of SEQ ID NO:3, and a fifth expression cassette comprising at least 90% sequence identity, e.g., at least 91%, 92%, 93%, 94%, 95%, 96%, 97%, 98%, 99% or 100% sequence identity, to nucleic acid residues 7-790 of SEQ ID NO:8, wherein the biosensor detects arsenic, cadmium, zinc and mercury.

In varying embodiments of the threshold biosensors, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:1, a second plasmid comprising at least 90% sequence identity, e.g., at least 91%, 92%, 93%, 94%, 95%, 96%, 97%, 98%, 99% or 100% sequence identity, to SEQ ID NO:2, a third plasmid comprising at least 90% sequence identity, e.g., at least 91%, 92%, 93%, 94%, 95%, 96%, 97%, 98%, 99% or 100% sequence identity, to SEQ ID NO:3, and a fourth plasmid comprising at least 90% sequence identity, e.g., at least 91%, 92%, 93%, 94%, 95%, 96%, 97%, 98%, 99% or 100% sequence identity, to SEQ ID NO:8, wherein the biosensor detects arsenic, cadmium, zinc and mercury.

Period Modulation Biosensors

In one embodiment, the colonies of cells comprise expression cassettes designed to produce a period modulation biosensor. Under this design, changed synchronized oscillating output signals (e.g., increased amplitude and period) are produced in the presence of analyte above a threshold concentration or above a concentration detected by the response element. In a particular embodiment, colonies of cells in a period modulation biosensor comprise the following expression cassettes:

i) an acyl-homoserine lactone (AHL) synthase LuxI gene under the control of a response element promoter;

ii) a LuxR gene under the control of a luxR promoter and an aiiA gene under the control of a luxI promoter;

iii) a LuxR gene under the control of a luxR promoter and a nucleic acid encoding a protein that produces free radicals or oxygen reactive species (e.g., $H_2O_2$) under the control of a luxI promoter; and iv) a LuxR gene under the control of a luxR promoter and a LuxI gene under the control of a luxI promoter, wherein the colonies of cells comprise a period modulation sensor that produces a changed oscillating signal in the presence of concentrations of an analyte above a threshold concentration, wherein the analyte binds to the response element promoter. In varying embodiments, the changed oscillating signal comprises increased oscillatory amplitude and period.

In varying embodiments of the period modulation biosensor, the cells comprise a set of expression cassettes comprising:

i) an acyl-homoserine lactone (AHL) synthase LuxI gene under the control of an arsenite response element (pArsR);

ii) a LuxR gene under the control of a luxR promoter and an aiiA gene under the control of a luxI promoter;

iii) a LuxR gene under the control of a luxR promoter and a nucleic acid encoding a protein that produces free radicals or oxygen reactive species under the control of a luxI promoter; and iv) a LuxR gene under the control of a luxR promoter and a LuxI gene under the control of a luxI promoter, wherein the biosensor detects arsenic.

In varying embodiments of the period modulation biosensor, the cells comprise a set of expression cassettes comprising:

i) an acyl-homoserine lactone (AHL) synthase LuxI gene under the control of a cadmium response element (yodA/cadA/cadR);

ii) a LuxR gene under the control of a luxR promoter and an aiiA gene under the control of a luxI promoter;

iii) a LuxR gene under the control of a luxR promoter and a nucleic acid encoding a protein that produces free radicals or oxygen reactive species under the control of a luxI promoter; and iv) a LuxR gene under the control of a luxR promoter and a LuxI gene under the control of a luxI promoter, wherein the biosensor detects cadmium.

In varying embodiments of the period modulation biosensor, the cells comprise a set of expression cassettes comprising:

i) an acyl-homoserine lactone (AHL) synthase LuxI gene under the control of an arsenite response element (pArsR);

ii) an acyl-homoserine lactone (AHL) synthase LuxI gene under the control of a cadmium response element (yodA/cadA/cadR);

iii) a LuxR gene under the control of a luxR promoter and an aiiA gene under the control of a luxI promoter;

iv) a LuxR gene under the control of a luxR promoter and a nucleic acid encoding a protein that produces free radicals or oxygen reactive species under the control of a luxI promoter; and v) a LuxR gene under the control of a luxR promoter and a LuxI gene under the control of a luxI promoter, wherein the biosensor detects arsenic and cadmium.

In some embodiments of the period modulation biosensor, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 7-1795 of SEQ ID NO:4, a second expression cassette comprising at least 90% sequence identity, e.g., at least 91%, 92%, 93%, 94%, 95%, 96%, 97%, 98%, 99% or 100% sequence identity, to nucleic acid residues 1895-3488 of SEQ ID NO:4, a third expression cassette comprising at least 90% sequence identity, e.g., at least 91%, 92%, 93%, 94%, 95%, 96%, 97%, 98%, 99% or 100% sequence identity, to nucleic acid residues 10-1771 of SEQ ID NO:5, and a fourth expression cassette comprising at least 90% sequence identity, e.g., at least 91%, 92%, 93%, 94%, 95%, 96%, 97%, 98%, 99% or 100% sequence identity, to nucleic acid residues 1-1203 of SEQ ID NO:6.

In some embodiments of the period modulation biosensor, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:4, a second plasmid comprising at least 90% sequence identity, e.g., at least 91%, 92%, 93%, 94%, 95%, 96%, 97%, 98%, 99% or 100% sequence identity, to SEQ ID NO:5, and a third plasmid comprising at least 90% sequence identity, e.g., at least 91%, 92%, 93%, 94%, 95%, 96%, 97%, 98%, 99% or 100% sequence identity, to SEQ ID NO:6.

In some embodiments of the period modulation biosensor, the colonies of cells further comprise an expression cassette comprising at least 90% sequence identity, e.g., at least 91%, 92%, 93%, 94%, 95%, 96%, 97%, 98%, 99% or 100% sequence identity, to nucleic acid residues 1-641 of SEQ ID NO:10, wherein the biosensor further detects arsenic and cadmium.

In some embodiments of the period modulation biosensor, the colonies of cells further comprise comprising an expression cassette comprising at least 90% sequence identity, e.g., at least 91%, 92%, 93%, 94%, 95%, 96%, 97%, 98%, 99% or 100% sequence identity, to nucleic acid residues 1-643 of SEQ ID NO:11, wherein the biosensor further detects arsenic, cadmium, zinc and mercury.

In some embodiments of the period modulation biosensor, the colonies of cells further comprise a plasmid comprising at least 90% sequence identity, e.g., at least 91%, 92%, 93%, 94%, 95%, 96%, 97%, 98%, 99% or 100% sequence identity, to SEQ ID NO:10, wherein the biosensor further detects arsenic and cadmium.

In some embodiments of the period modulation biosensor, the colonies of cells further comprise a plasmid comprising at least 90% sequence identity, e.g., at least 91%, 92%, 93%, 94%, 95%, 96%, 97%, 98%, 99% or 100% sequence identity, to SEQ ID NO:11, wherein the biosensor further detects arsenic, cadmium, zinc and mercury.

In some embodiments of the period modulation biosensor, the colonies of cells comprise a first expression cassette comprising at least 90% sequence identity, e.g., at least 91%, 92%, 93%, 94%, 95%, 96%, 97%, 98%, 99% or 100% sequence identity, to nucleic acid residues 7-1795 of SEQ ID NO:4, a second expression cassette comprising at least 90% sequence identity, e.g., at least 91%, 92%, 93%, 94%, 95%, 96%, 97%, 98%, 99% or 100% sequence identity, to nucleic acid residues 1895-3488 of SEQ ID NO:4, a third expression cassette comprising at least 90% sequence identity, e.g., at least 91%, 92%, 93%, 94%, 95%, 96%, 97%, 98%, 99% or 100% sequence identity, to nucleic acid residues 10-1771 of SEQ ID NO:5, and a fourth expression cassette comprising at least 90% sequence identity, e.g., at least 91%, 92%, 93%, 94%, 95%, 96%, 97%, 98%, 99% or 100% sequence identity, to nucleic acid residues 1-641 of SEQ ID NO:10 or at least 90%, 91%, 92%, 93%, 94%, 95%, 96%, 97%, 98%, 99% or 100% sequence identity, to nucleic acid residues 1-643 of SEQ ID NO:11, wherein the biosensor detects cadmium.

In some embodiments of the period modulation biosensor, the colonies of cells comprise a first plasmid comprising at least 90% sequence identity, e.g., at least 91%, 92%, 93%, 94%, 95%, 96%, 97%, 98%, 99% or 100% sequence identity, to SEQ ID NO:4, a second plasmid comprising at least 90% sequence identity, e.g., at least 91%, 92%, 93%, 94%, 95%, 96%, 97%, 98%, 99% or 100% sequence identity, to SEQ ID NO:5, and a third plasmid comprising at least 90% sequence identity, e.g., at least 91%, 92%, 93%, 94%, 95%, 96%, 97%, 98%, 99% or 100% sequence identity, to SEQ ID NO:10 or at least 91%, 92%, 93%, 94%, 95%, 96%, 97%, 98%, 99% or 100% sequence identity, to SEQ ID NO:11.

The expression cassettes can also include termination sequences appropriate to the host cells. The expression cassettes can be inserted into a vector (e.g., a plasmid, a viral vector) for expression in an appropriate host cell. Alternatively, the expression cassettes can be incorporated into the genome of the host cells. When incorporated into plasmids vectors, sequences for replication, copy number and selection (e.g., antibiotic resistance genes) can be included. Components of plasmid expression vectors are known in the art and plasmid expression vectors for a variety of host cells, including bacterial cells, yeast cells, algae cells, plant cells, mammalian cells, and insect cells, are commercially available. In varying embodiments the expression cassettes are incorporated into a plasmid vector for expression in bacterial cells, e.g., *E. coli* cells. The biosensor circuits created by different assemblies and configurations of the expression cassettes can be readily configured according to the analyte intended to be detected. One or multiple plasmids comprising a set of expression cassettes that create a biological circuit with frequency modulated output can be readily designed and assemble to a desired purpose, e.g., using the modular plasmid system described in Lutz and Bujard (Nucleic Acids Res., (1997) 25(6), 1203-10).

4. Sensors and Response Elements

As appropriate, known response elements and response element promoters can be used in the biosensors to detect an analyte of interest. As described herein, the arsR promoter of *E. coli* fused to a reporter gene can be used to detect arsenic (Stocker, et al., Environmental Science & Technology, (2003) 37(20):4743-4750). For detection of mercury, the *E. coli* merR gene can be employed and a truncated version of the merT gene fused to a reporter (Lyngberg, et al., *J Ind Microbiol Biotechnol*, (1999) 23(1):668-676). For detection of cadmium, the pSLzntR/pDNPzntA—reporter system can be used (Ivask, et al., *BMC Biotech* (2009) 9:41).

Another class of potentially dangerous chemicals are organophosphorus (OP) neurotoxins, a group which includes both common pesticides and nerve agents such as VX and sarin (Mulchandani and Rajesh., *Appl Biochem Biotechnol*, (2011) 165(2):687-699; Rainina, et al., *Biosens Bioelectron*, (1996) 11(10):991-1000). Due to their wide distribution throughout the world as industrial and agricultural chemicals, they have long been viewed as potential weapons by terrorist groups [Gleick. *Water Policy*, (2006) 8(6):481-503; Hickman, Technical report, Air University Press Maxwell AFB, AL 36112-6615, 1999]. An *E. coli* strain expressing the organophosphorus hydrolase (OPH) gene of *Flavobacterium* sp. ATCC 27551, e.g., as described in [Rainina, et al., *Biosens Bioelectron*, (1996) 11(10):991-1000], can be used. This enzyme hydrolyzes a large group of OP compounds including sarin, VX and pesticides such as paraoxon [Rainina, et al., supra]. RNA-seq can be employed to find genes induced upon OP hydrolysis to generate signaling inputs for the classifier.

A number of toxins arise from cyanobacteria blooms which are becoming more common across the globe. Cyanobacteria of various genera, especially Microcystis, can produce cyclic heptapeptide toxins known as microcystins [States, et al., *Journal American Water Works Association*, (2003) 95(4):103-115]. These toxins promote tumors and can cause death by liver haemorrhage and respiratory arrest [Codd, *Ecological Engineering*, (2000) 16(1):51-60, 2000; Pouria, et al., *Lancet*, (1998) 352(9121):21-26]. To detect microcystins, the mlrABCD genes of *Sphingomonas* sp. can be expressed, which metabolize microcystin [Bourne, et al., *Environ Toxicol*, (2001) 16(6):523-534]. The recombinant cells can be exposed to microcystin and output genes identified using the RNA-seq methodology described herein. Similarly, in order to detect the presence of cyanide, the cyanide oxygenase gene (CNO) of the bacterium *Pseudomonas fluorescens* NCIMB 11764 can be expressed (e.g., in *E. coli*), and genes differentially expressed in response to cyanide exposure can be detected.

Novel genetic outputs responding to toxin exposure can be readily discovered, e.g., using RNA-seq technology. In varying embodiments, *E. coli* cells can be exposed to a toxin of interest and the expression profiles of induced genes to control cultures can be compared. Total RNA is extracted from the cell cultures and enrich for mRNA (van Vliet, *FEMS Microbiol Lett*, (2010) 302(1):1-7). Random hexamer primers can be used to produce cDNA. cDNA can be sequenced using any method known in the art, e.g., an Illumina MySeq machine and the data set can be analyzed using any appropriate available analytical software, e.g., the EDENA program [Croucher and Thomson., *Curr Opin Microbiol*, (2010) 13(5):619-624). Genes differentially expressed in response to toxin exposure are determined and used as signals for the classifier. Since the whole transcriptome is being scanned with this technique multiple potential outputs for each toxin can be identified, facilitating the selectivity of the sensor. RNA-seq technology can be combined with known response promoters to detect heavy metals.

Any analyte which *E. coli* responds to can be detected using the presently designed biosensors (e.g., by switching the response element promoter). In more complicated cases where a single promoter may not exist, suites of promoters can be identified that make up a vector-based "promoter signature" using next-gen sequencing. Such analytes include without limitation heavy metals, bacterially metabolizable compounds, and other compounds, depending on the response. Pathogenic bacteria can also be readily detected since they use quorum-sensing as well, by switching the quorum-sensing response element in the presently described circuits.

Arsenic Biosensors

Biosensors offer a convenient, rapid, specific and sensitive means of monitoring analytes and of reporting the presence of specific toxins, generally producing a signal which proportional to concentration (Morris, *Cell Biochemistry and Biophysics*, (2010) 56(1), 19-37). Several whole-cell bacterial biosensors for arsenic have been described in the literature (Tauriainen, et al., *Applied and Environmental*

*Microbiology*, (1997) 63(11):4456; Scott, et al., *Anal. Chem*, (1997) 69(1), 16-20; Ramanathan, et al., *Anal. Chem*, (1997) 69(16), 3380-3384.), which typically employ nonpathogenic laboratory strains of *E. coli*, the natural resistance mechanism of *E. coli* against arsenite and arsenate, and reporter proteins (Stocker, et al., Environ. Sci. Technol, (2003) 37(20):4743-4750).

These biosensors typically employ the natural resistance mechanism of bacteria against arsenic, encoded by the ars operon (Kaur and Rosen, *Plasmid*, (1992) 27(1):29-40). In the absence of arsenite, the ArsR repressor binds to its operator/promotor site within the ars operon and prevents further expression of itself and the downstream genes (Rosen, *Journal Of Basic And Clinical Physiology And Pharmacology*, (1995) 6(3-4):251). When arsenite enters the cell, it interacts with ArsR, causing a conformational change, dissociation of the ArsR protein from its operator, and expression of the ars genes. Therefore, one approach is to perform arsenite measurements using genetically engineered bacterial cells, which produce a fluorescent protein under control of the ArsR regulatable promoter.

The first large-scale environmental validation of a microbial reporter-based test to measure arsenic concentrations in natural water resources was developed in 2005 (Trang, et al., *Environmental Science & Technology*, (2005) 39(19), 7625-7630). In this study, a bioluminescence-producing arsenic-inducible strain was shown to perform far better than most chemical field test kits in detecting arsenic at low concentrations. Realizing the importance of a closed, single-use incubation and detection system, another group designed a microfluidic arsenic biochip containing immobilized *E. coli* biosensor bacteria that express GFP when exposed to arsenite ions (Theytaz, et al., *Procedia Chemistry*, (2009) 1(1): 1003-1006).

Taking a slightly different approach, a group in Edinburgh devised a biosensor that senses arsenic in drinking water and produces a pH change as the output (Aleksic, et al., *Synthetic Biology*, IET, (2007) 1(1.2):87-90). This system employs the same arsenate-responsive promoter of *E. coli*, but uses urease to increase pH in the absence of arsenate and β-galactosidase (LacZ) to decrease pH in the presence of arsenate. However, while the group was able to generate pH changes for some levels of arsenate, they ran into problems with dynamic range, repeatability, and response time.

Heavy Metal Biosensors

While heavy metals are toxic in concentrations above a given threshold to microorganisms, some bacteria can adapt to their presence by using precisely regulated, genetically encoded resistance mechanisms. The resistance to certain toxic metals, including cadmium, works by employing an energy-dependent pump in the cell membrane to exclude the molecules (Nucifora, et al., *Proc Natl Acad Sci USA*, (1989) 86(10):3544; Zhang, et al., *Current Microbiology*, (2008) 56(3), 236-239). Some bacteria have natural metal resistance operons, such as the cadmium resistance system, CadA, of *Pseudomonas putida*, which is regulated by cadR (Lee, et al., *Applied and Environmental Microbiology*, (2001) 67(4): 1437). The precise regulation of these genes has been used to engineer sensor bacteria, in which the regulatory element controls the expression of a reporter gene.

In one study, an *E. coli* strain was engineered to express red-shifted green fluorescent protein (rs-GFP) under control of CadC, the regulatory protein of the cad operon in *Staphylococcus aureus* (Shetty, et al., *Analytical And Bioanalytical Chemistry*, (2003) 376(1):11-17). The reporter protein was produced proportionally to the amount of cadmium and lead used to induce the bacteria, and the bacterial sensing systems were found to respond to cadmium, lead, and zinc ions but had no significant response to other metals. A similar system was constructed by another group, which used the regulation unit from the CadA system to control the expression of firefly luciferase. The response to extracellular heavy metals was studied in several bacteria, and specificity was generally an issue (Tauriainen et al., *Biosensors and Bioelectronics*, (1998) 13(9):931-938).

Most recently, synthetic biology was employed to create a whole-cell cadmium sensor using a toggle gene circuit (Wu, et al., *Biotechnology Progress*, (2009) 25(3)). A cadmium-inducible promoter was used to produce GFP in response to addition of cadmium to the medium, and this approach presented improvements in sensitivity and specificity over other existing biosensor strains. However, the inherent limitation of providing an "on-off" reading greatly limited the range of detection.

The biosensors described herein can be used for the development of a genetic classifier integrated with a frequency modulated (FM) output circuit. A classifier is a system that uses multiple inputs to successfully discriminate between at least two possible outcomes; analyte levels that are above or below a predetermined threshold level (e.g. dangerous vs. acceptable levels of toxins). One feature of a classifier is the ability to train based on presented examples. In designs described herein, during training and operation, the levels of chemical inducers that shift the dynamic range and the output threshold of the classifier can be continuously computed and altered within the microfluidic device in an iterative feedback fashion.

The synthetic classifier can be tightly integrated with the synthetic gene oscillator as a frequency-modulated output element [Danino, et al., *Nature*, (2010) 463(7279):326-330; Prindle, et al., *Nature*, (2011) 481(7379):39-44, both of which are hereby incorporated herein by reference in their entirety for all purposes]. Using a threshold biosensor design, the system can be trained so that the biopixels will produce periodic pulses of $H_2O_2$ for the levels of toxins above a pre-defined threshold and remain silent below it. To adjust the threshold level the concentrations of chemical inducers that directly affect the input oscillator sensitivity to toxin-reporting proteins can be shifted. Algorithms developed in machine learning [Bishop. Pattern Recognition and Machine Learning, Information Science and Statistics. Springer, 1st ed. 2006. con. 2nd printing edition, October 2007; Vapnik. The nature of statistical learning theory. Springer-Verlag New York, Inc., New York, N.Y., USA, 1995; and Muller, et al., IEEE transactions on neural networks, (2001) 12(2):181-201] to perform training and optimization tasks in a continuous fashion during training and actual operation can be used. In a multi-trap microfluidic design, spatially varying concentrations of chemical inducers across a field of biopixels can be used. Collecting multi-channel readouts from biopixels subjected to different inducer concentrations allows improved learning and classification efficiency.

5. Devices

The devices generally comprise cell colonies capable of synchronized communication (e.g., via gas phase) within a microfluidic array. The colonies or populations of cells within the biosensors allow for synchronization of 2.5 million or more cells, e.g., 3, 3.5, 4, 4.5 or 5 million cells, across a distance of at least 5 mm, e.g., 5.5 mm, 6.0 mm, 6.5 mm, 7.0 mm, 7.5 mm, or longer. Provided herein are microfluidic-based biosensors which have the capability to detect analytes of interest, including, e.g., sub-lethal quantities of heavy metals (e.g., mercury, arsenic, cadmium, zinc, lead and others listed herein), organophosphate based nerve agents and pesticides, cyanobacterial toxins (e.g., microcystin and cyanide). The biosensor device can be readily designed and configured to detect other analytes of interest, e.g., using next generation sequencing technologies. In particular embodiments, *E. coli* can be used as the cellular platform. While *E. coli* is not generally found in unpolluted natural waters, the design of the present microfluidic devices ensures that the *E. coli* cell colonies are capable of robust sensing in these environments. Specifically, the mass transfer from the influent sample stream to the cell chambers is substantially completely or solely due to diffusion, preventing these cells from contacting viruses, bacteria and protozoa that are responsible for eliminating *E. coli* in natural waters. Furthermore the device described herein can be designed to be contained in a small, temperature controlled enclosure, preventing exposure to damaging UV radiation.

In varying embodiments, the sensor design can incorporate miniaturized redox electrodes patterned directly on-chip in the biopixel array. The resulting "bacto-electronic" sensor converts environmental stimuli to electrical current via a programmable biological intermediate. Electronic detection of $H_2O_2$ has previously been performed in microfluidic devices [Yan, et al., *Biomicrofluidics*, (2011) 5(3):032008; Ikariyama, et al., *Journal of Electroanalytical Chemistry and Interfacial Electrochemistry*, (1988) 251(2):267-274; Ino, et al., *Biosensors and Bioelectronics*, (2010) 25(7): 1723-1728], usually with an enzyme catalyst such as horseradish peroxidase (HRP), to detect concentrations as low as 1 μM $H_2O_2$. The composition of the working electrode can comprise designs including micropatterned gold [Yan, et al., supra], platinum black [Ikariyama, et al., supra], or indium-tin-oxide coated with conductive polymer [Lei, et al., *Analytica Chimica Acta*, (2006) 568(1):200-210]. Platinum [Jones. Applications of hydrogen peroxide and derivatives, Volume 2 of Rsc Clean Technology Monographs. *Royal Society of Chemistry*, 1999] and palladium electrodes are electrocatalytic, meaning HRP is not needed; however, oxide formation decreases electrode performance over time [Gilroy and Conway, *Canadian Journal of Chemistry*, (1968) 46(6):875-890, 1968].

Evaporative deposition and etching can be employed to deposit platinum black electrodes on a silicon substrate. This process employs similar equipment to the photolithography method used in constructing a variety of microfluidic devices, and can be performed simultaneously. $H_2O_2$ in bulk solution (over 1 mL sample volume) can be detected using an off-the-shelf oxidation-reduction potential (ORP) probe system. $H_2O_2$ was detected at concentrations as low as 100 nM, which is improved over a previously described bacterial $H_2O_2$ output in excess of 1 mM with the spxB gene [Pericone, et al., *Journal of Bacteriology*, (2003) 185(23):6815-6825]. In varying embodiments, the microfluidic arrays fit on a chip the size of a standard microscope slide or smaller.

EXAMPLES

The following examples are offered to illustrate, but not to limit the claimed invention.

Example 1

A Sensing Array of Radically Coupled Genetic 'Biopixels'

Synergistic Synchronization

Figure 1:
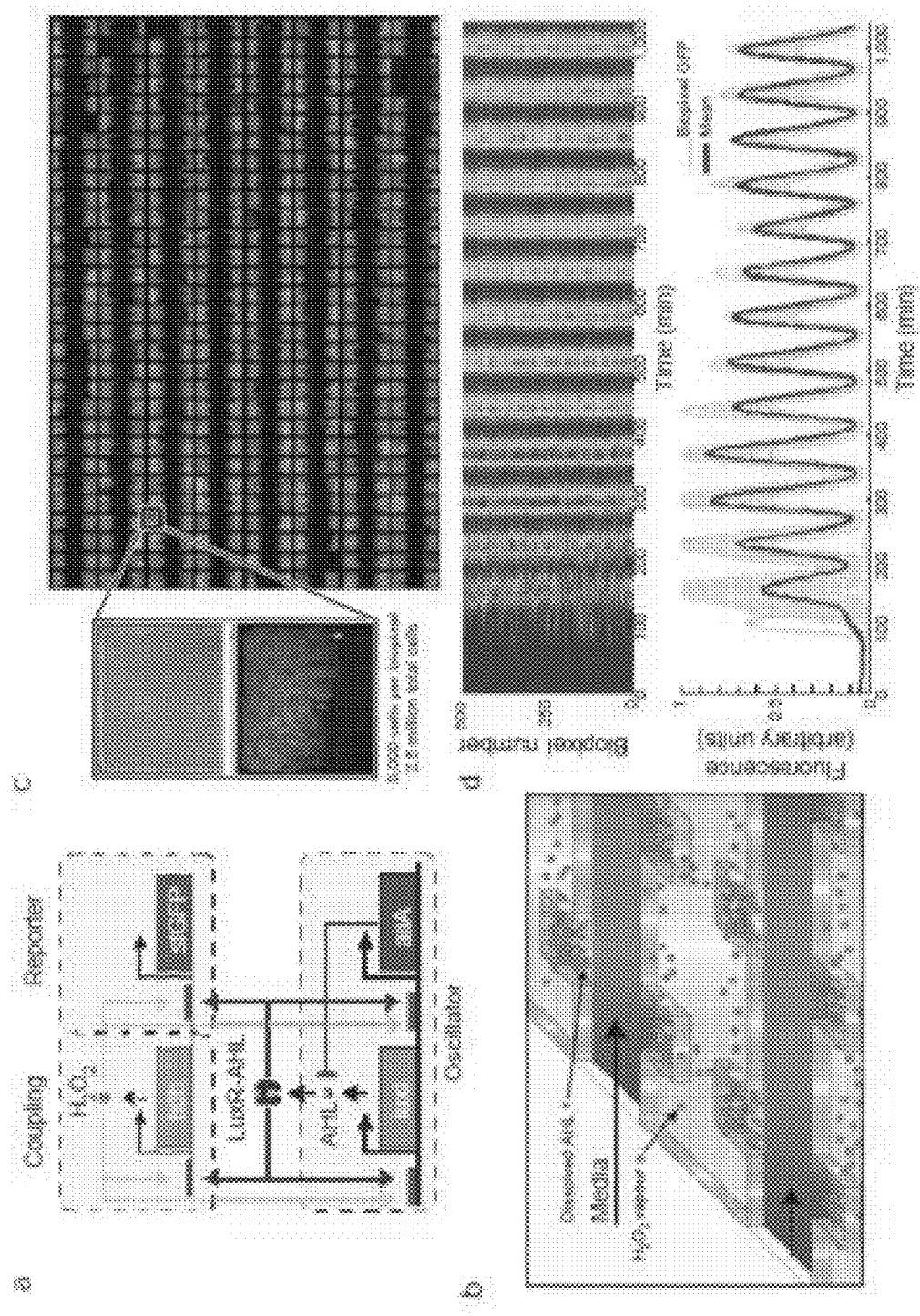
FIGS. 1A-D illustrate a sensing array of radically coupled genetic biopixels. a, Network diagram. The luxI promoter drives expression of luxI, aiiA, ndh and sfGFP (superfolder variant of GFP) in four identical transcription modules. The quorum-sensing genes luxI and aiiA generate synchronized oscillations within a colony via AHL. The ndh gene codes for NDH-2, an enzyme that generates $H_2O_2$ vapor, which is an additional activator of the luxI promoter. $H_2O_2$ is capable of migrating between colonies and synchronizing them. b, Conceptual design of the sensing array. AHL diffuses within colonies while $H_2O_2$ migrates between adjacent colonies through the PDMS. Arsenite-containing media is passed in through the parallel feeding channels. c, Fluorescent image of an array of 500 E. coli biopixels containing about 2.5 million cells. Inset, bright-field and fluorescent images display a biopixel of 5,000 cells. d, Heat map and trajectories depicting time-lapse output of 500 individual biopixels undergoing rapid synchronization. Sampling time is 2 min.
Figure 2A:
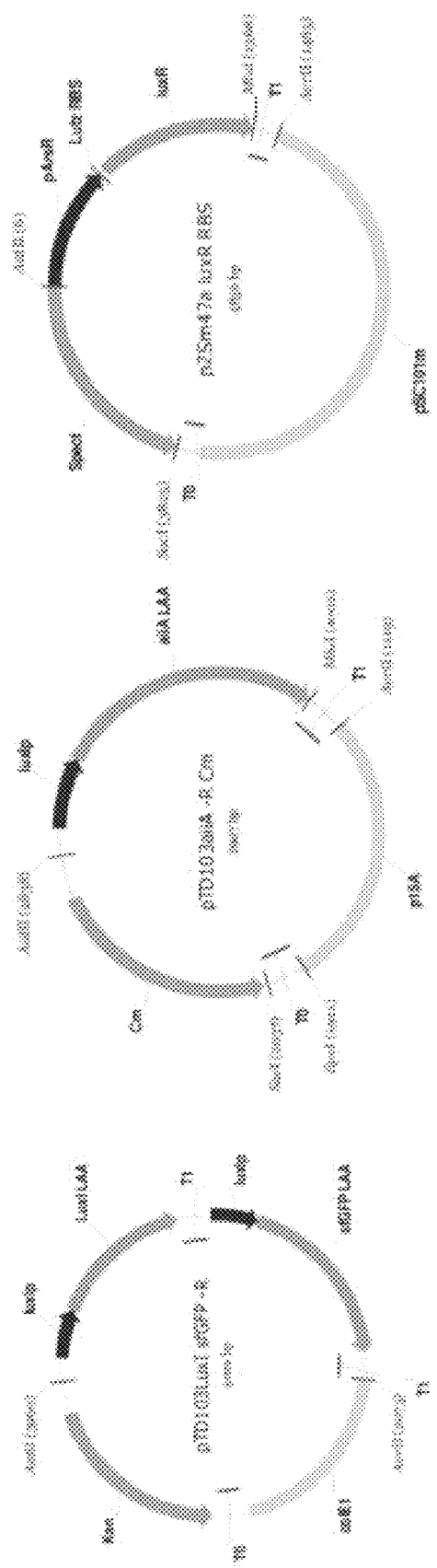
FIG. 2A-C illustrate the plasmids used to create biosensor circuits with frequency modulated output. Top row is the thresholding sensor: 2 oscillator plasmids with luxR genes removed and a plasmid containing pArs::luxR. Middle row is the period modulator: 2 oscillator plasmids and a plasmid containing pArs::luxI-laa. Bottom row contains 2 plasmids used to study $H_2O_2$ production and synchronization: pLux:: ndh and pLux::sodA. NDH-2 synchronization strain is the oscillator plasmids with pZSm45 ndhII.
Figure 2B:
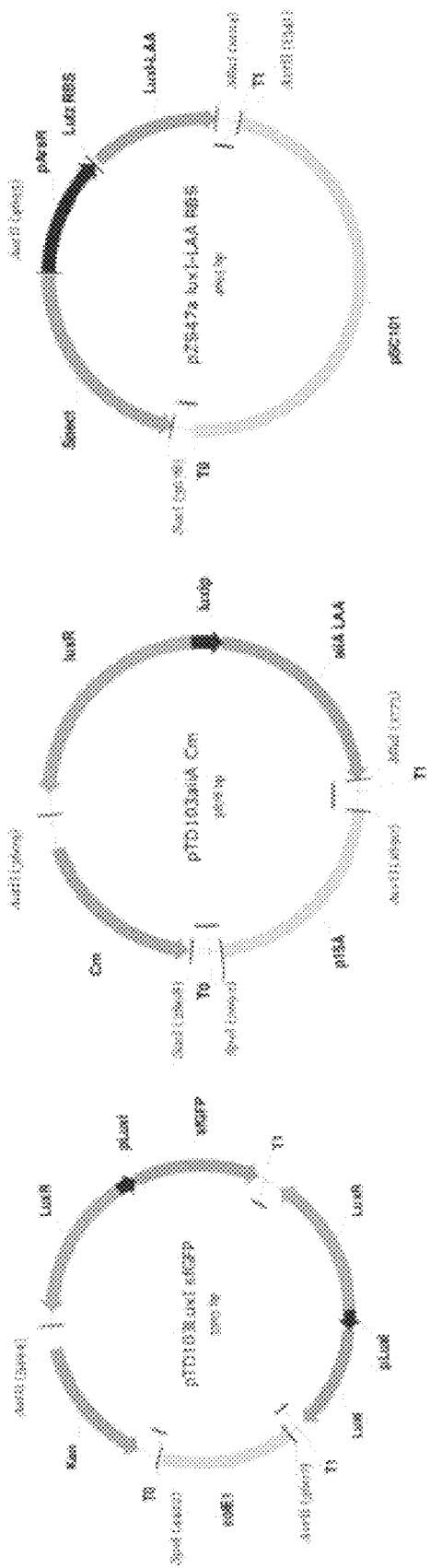
Figure 2C:
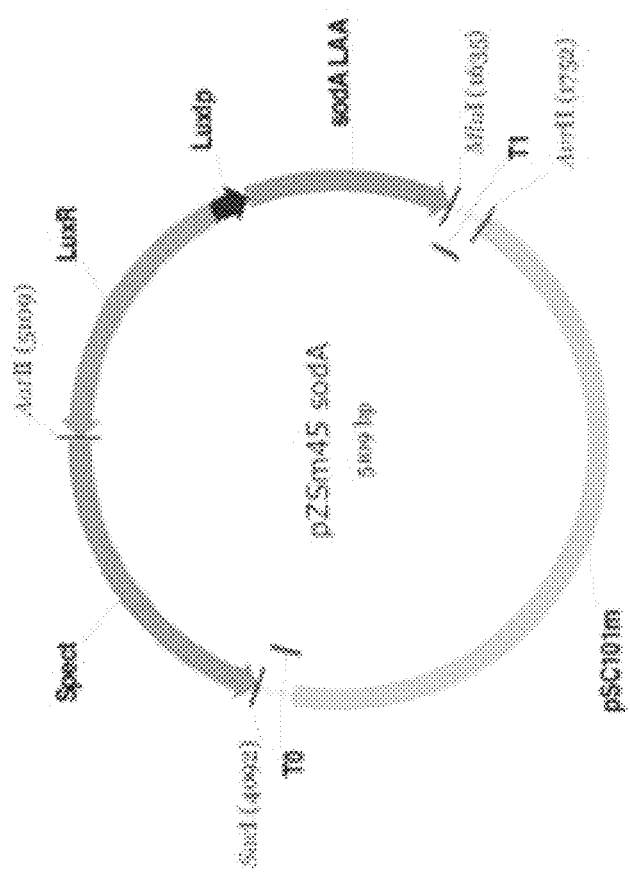
Figure 2C:
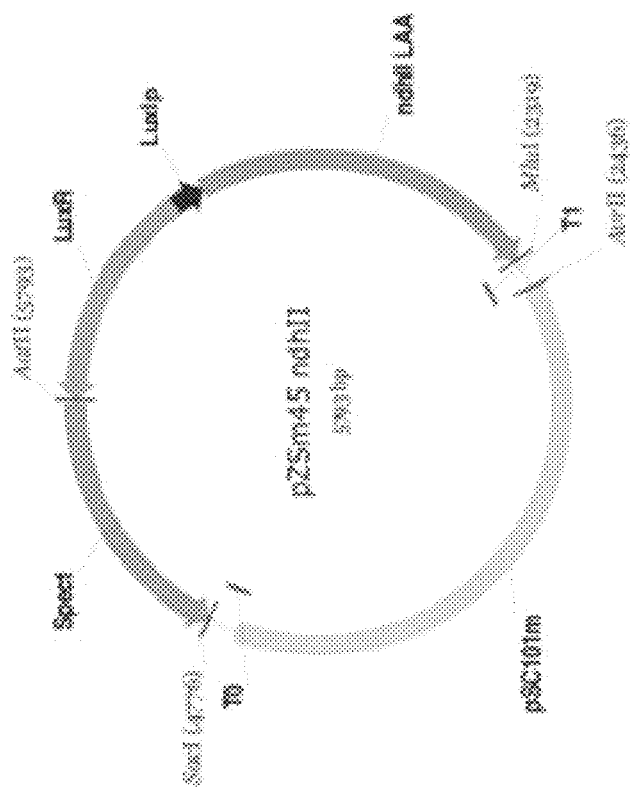
Figure 3:
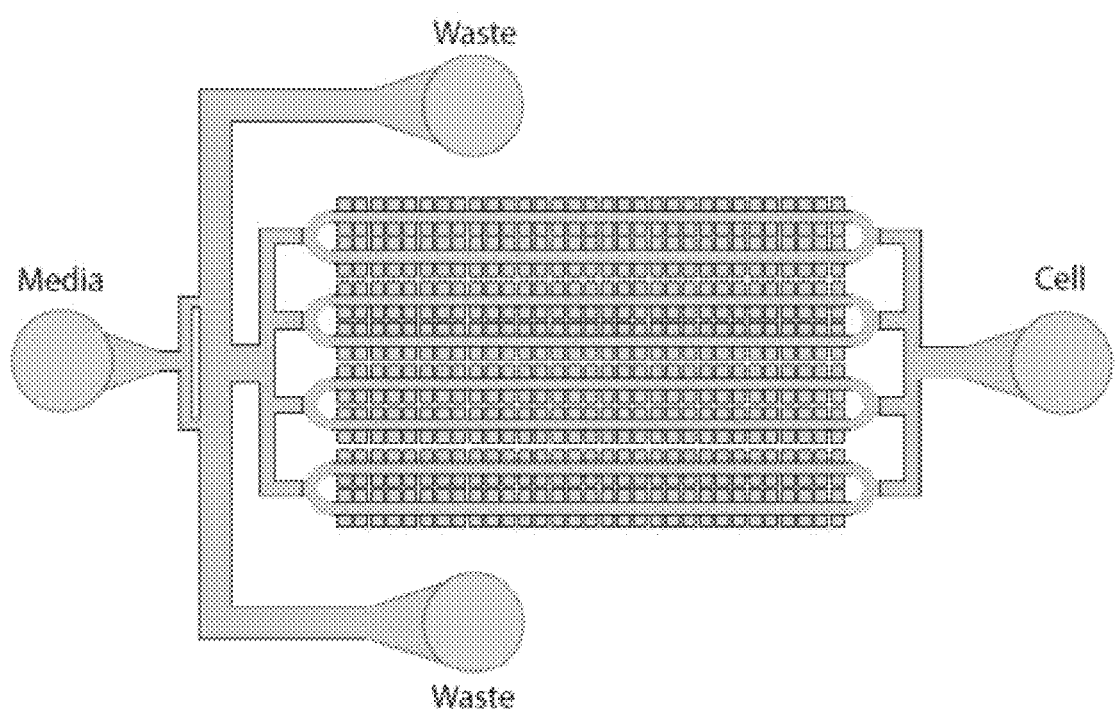
FIG. 3A-B illustrate a microfluidic device used for this study. A. Media containing variable analyte (e.g., arsenite) concentration is fed through the cell port, flowing past the biopixel array into the cell and waste ports. During loading, pressure is increased at the cell port and decreased at the waste ports to reverse the flow, allowing cells to pass by the trapping regions. Other microfluidic devices used have the same layout with trap number, separation, and size varied. B. An illustrative trapping chamber populated with cell colonies and showing the fluid flow path.
Figure 3:
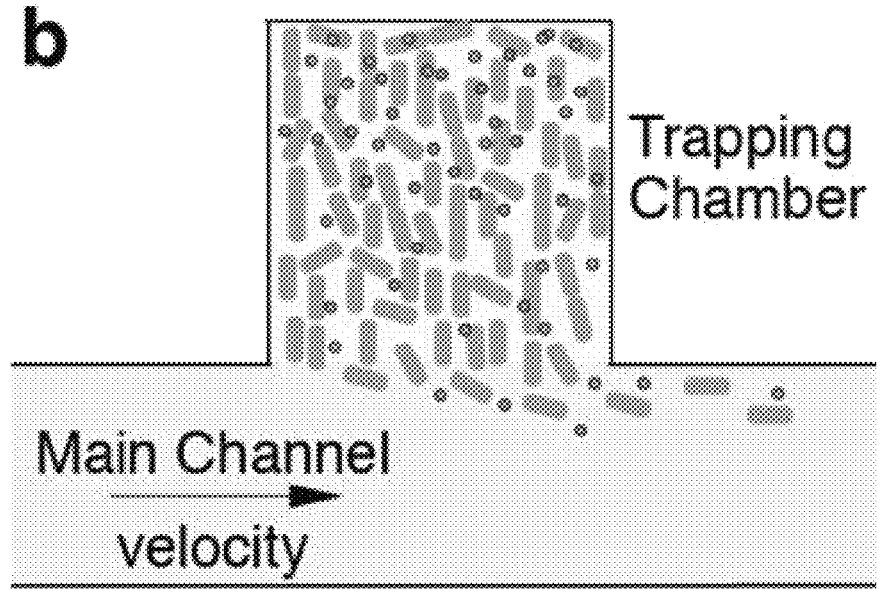

To develop a frequency-modulated biosensor, we designed a gene network capable of synchronizing genetic oscillations across multiple scales (FIG. 1*a* and FIG. 2). We constructed an LCD-like microfluidic (Ferry, et al., *Methods Enzymol*. (2011) 497:295) array that allows many separate colonies of sensing bacteria to grow and communicate rapidly by gas exchange (FIG. 1*b*, *c* and FIG. 3). As previous work (Danino, et al., *Nature* (2010) 463:326-330) has demonstrated that coupling through quorum sensing leads to incoherent oscillations at the millimeter scale, this mode of cellular communication is too slow for the generation of macroscopic synchronized oscillations. However, the slower quorum sensing can be used to synchronize small local colonies, provided there is a second level of design that involves faster communication for coordination between the colonies. Therefore, rather than attempting to engineer a sensor from a single large-colony oscillator, we wired together thousands of small oscillating colonies, or 'biopixels', in a microfluidic array. Coupling between biopixels involves redox signalling by hydrogen peroxide ($H_2O_2$) and the native redox sensing machineries of *E. coli*. The two coupling mechanisms act synergistically in the sense that the stronger, yet short-range, quorum sensing is necessary to coherently synchronize the weaker, yet long-range, redox signalling. Using this method we demonstrate synchronization of approximately 2.5 million cells across a distance of 5 mm, over 1,000 times the length of an individual cell (FIG. 1*c*, *d*). This degree of synchronization yields extremely consistent oscillations, with a temporal accuracy of about 2 min compared to 5-10 min for a single oscillator (Danino, et al., *Nature* (2010) 463:326-330) (FIG. 1*d*).

Figure 4:
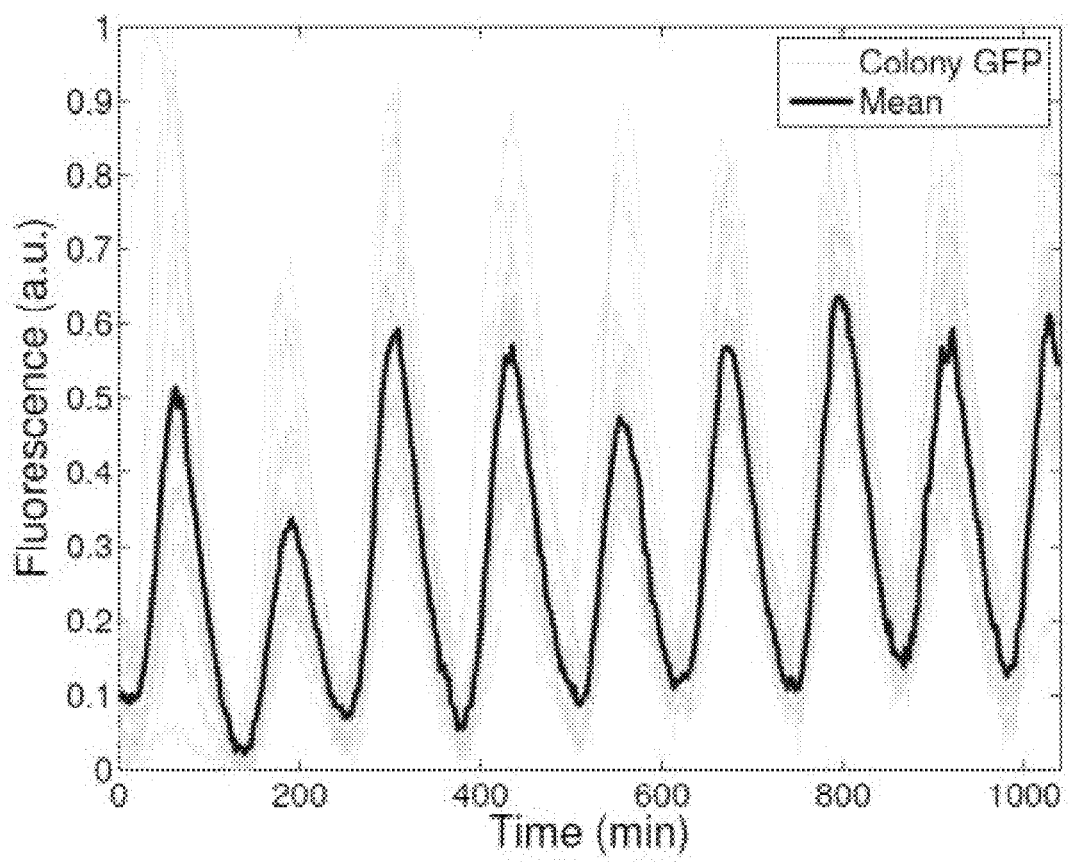
FIG. 4 illustrates biopixels with NDH-2 engineered synchronization observed at ultra-low fluorescence (4×, 20 ms exposure, 3% power) using an EMCCD camera to ensure no fluorescence interaction. Synchronized oscillations are maintained across the array for the length of the experiment (14 hours).

The global synchronization mechanism is comprised of two modes of communication that work on different scales. The quorum-sensing machinery (LuxI, AiiA) uses an acyl-homoserine lactone (AHL) to mediate intracolony synchronization. In our device, the degree to which neighboring colonies are able to influence each other via AHL diffusion is negligible owing to the high media channel flow rates. Instead, we engineered the cells to communicate via gas exchange by placing a copy of the gene coding for NADH dehydrogenase II (ndh) under the control of an additional lux promoter. NDH-2 is a membrane-bound respiratory enzyme that produces low levels of $H_2O_2$ and superoxide ($O_2^-$) (Messner, et al., *J. Biol. Chem.* (1999) 274:10119-10128). As $H_2O_2$ vapor is able to pass through the 25-mm oxygen-permeable polydimethylsiloxane (PDMS) walls that separate adjacent colonies, periodic production of NDH-2 yields periodic exchange of $H_2O_2$ between biopixels. When $H_2O_2$ enters the cell, it transiently changes its redox state, interacting with our synthetic circuit through the native aerobic response control systems, including ArcAB, which has a binding site in the lux promoter region (Bose, et al., *Mol. Microbiol.* (2007) 65, 538-553; Georgellis, et al., *Science* (2001) 292:2314-2316). Under normal conditions, ArcAB is partially active so lux is partially repressed. In contrast, oxidizing conditions triggered by $H_2O_2$ inactivate ArcAB, relieving this repression. Each oscillatory burst promotes firing in neighboring colonies by relieving repression on the lux promoter. This constitutes an additional positive feedback that rapidly synchronizes the population (FIG. 4).

Figure 5:
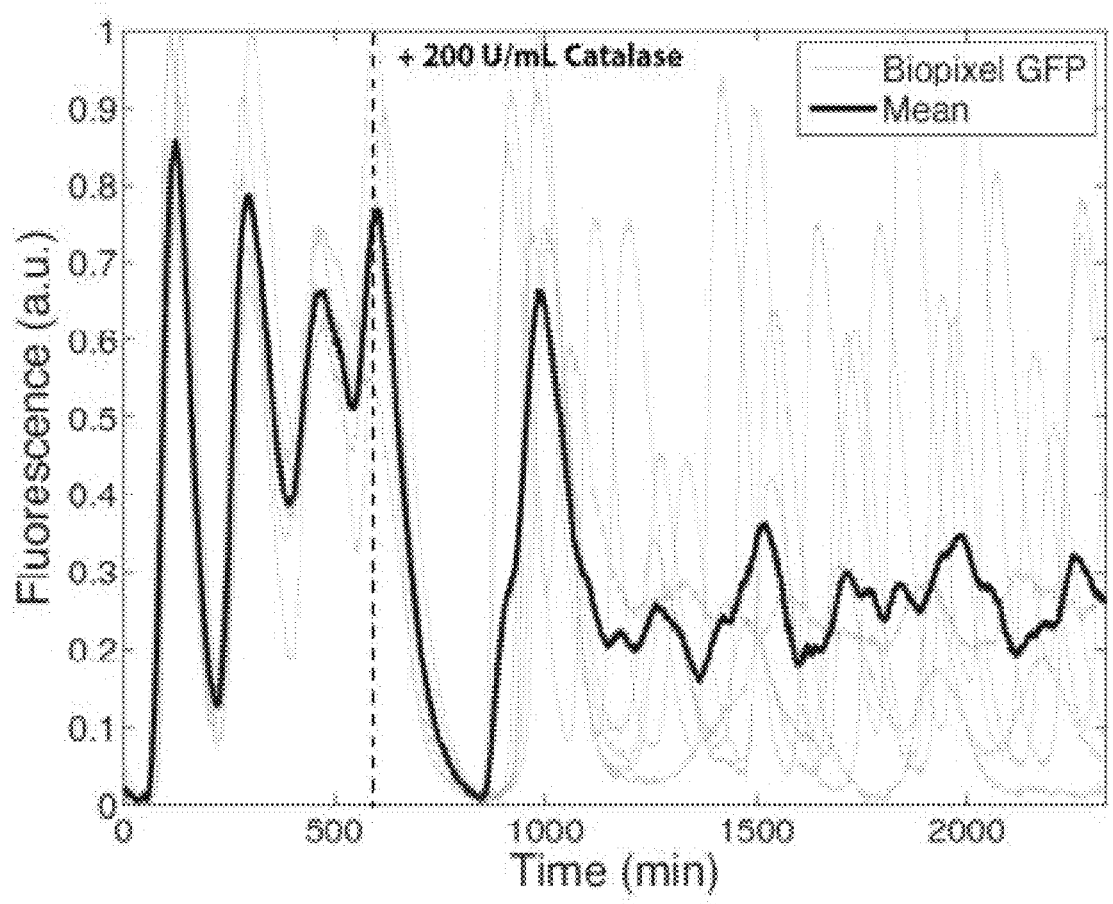
FIG. 5 illustrates that catalase degrades external $H_2O_2$ and prevents communication between colonies. When a synchronized population of biopixels was exposed to a step increase of 200 U/ml catalase, synchronization was broken and biopixels continued to oscillate individually. Since catalase cannot cross the cell membrane, this shows that synchronization between colonies depends on $H_2O_2$ but oscillations with a colony do not.
Figure 6:
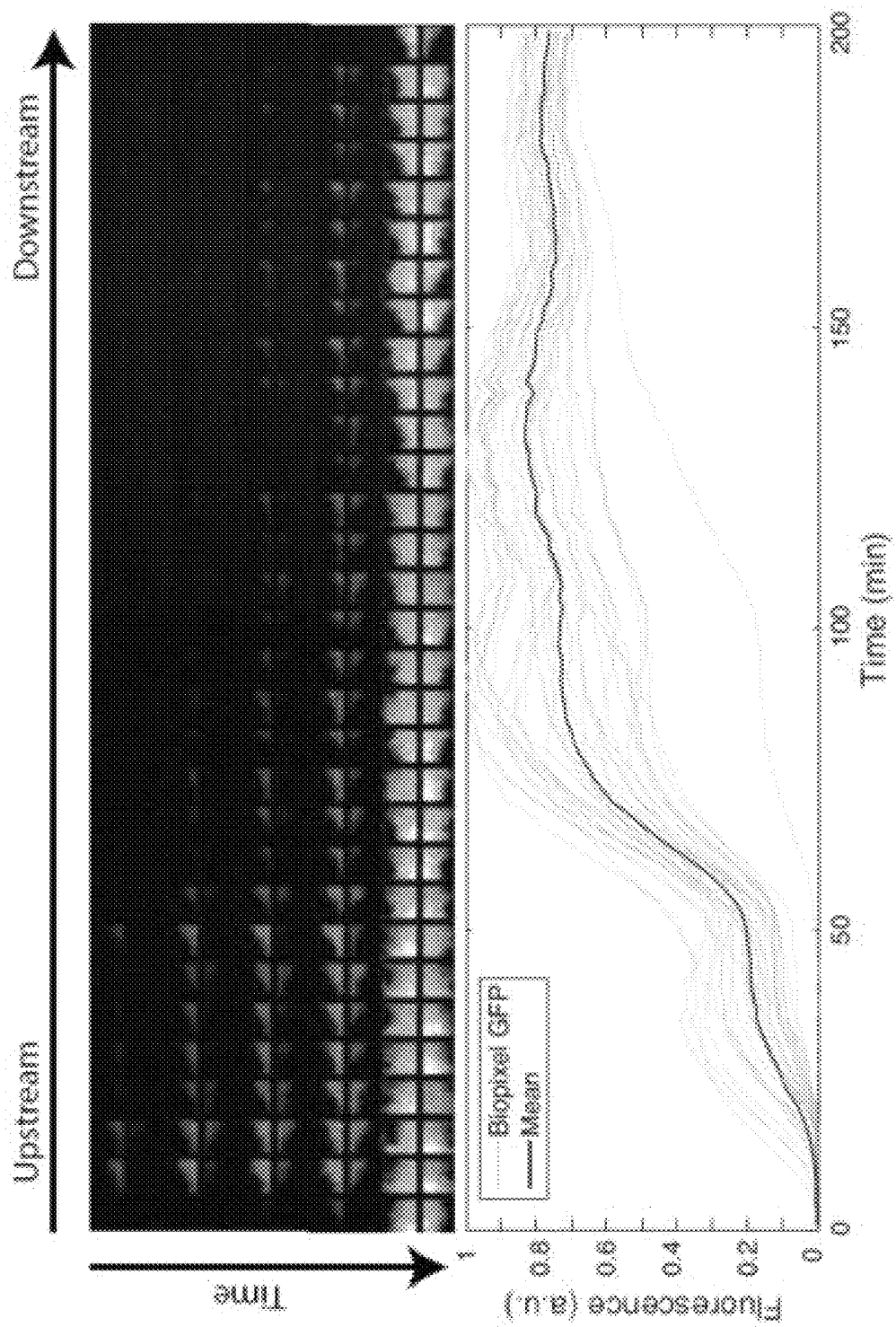
FIG. 6 illustrates that SodA produces $H_2O_2$ internal to the cell, permanently switching the cellular redox state (oxidizing) thereby activating lux-controlled genes. Biopixels rapidly fire and lock on in a spatial wave, far earlier than is typical for colonies of this size. The propagation of ON biopixels suggests that colonies are capable of activating those nearby via migrating $H_2O_2$ species.
Figure 7:
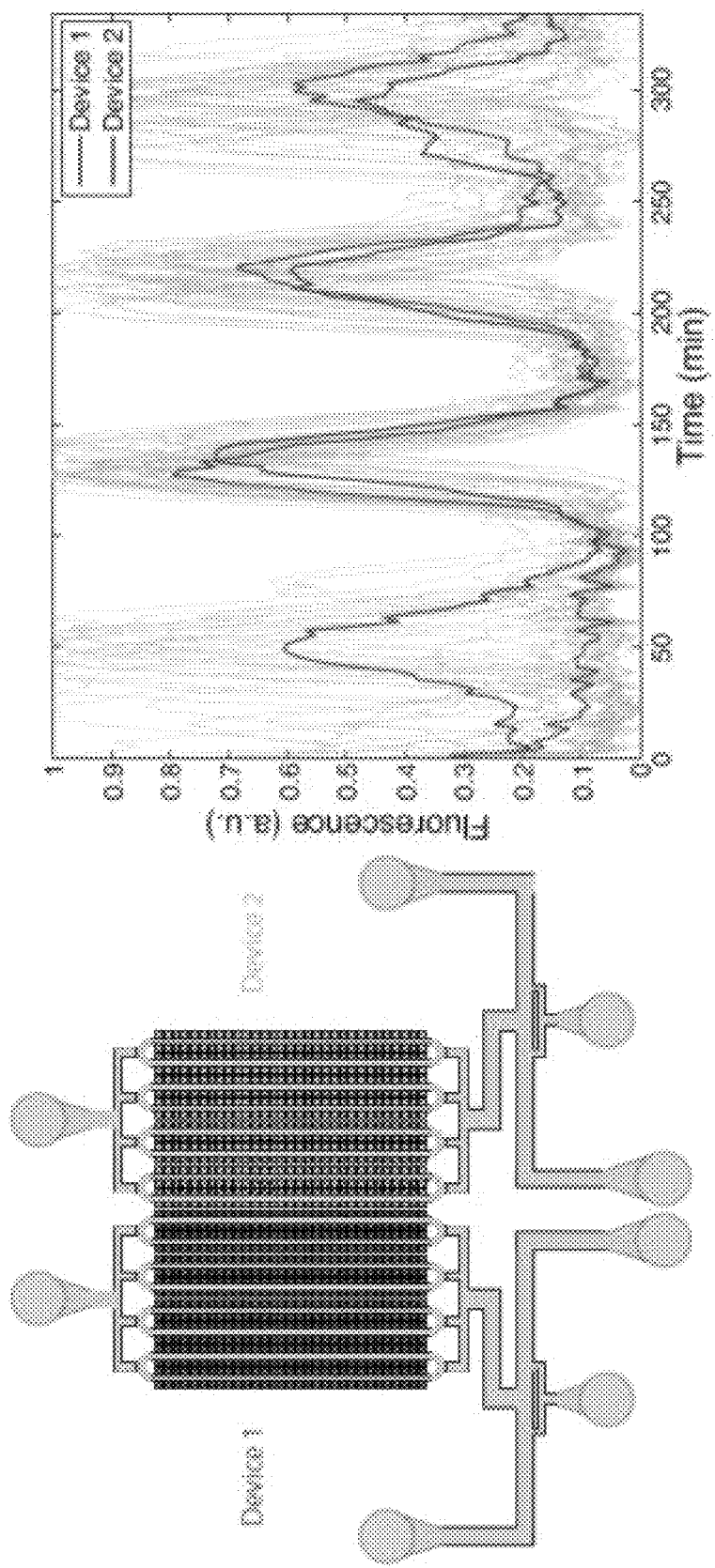
FIG. 7 illustrates that synchronized oscillations occur across 2 fluidically isolated devices held in close proximity. In this experiment, the devices were started at different times yet become synchronized. Since these devices share no common fluid sources or sinks, this confirms that synchronization is mediated by vapor species.

We investigated the effects of catalase and superoxide dismutase (SOD) to probe the nature of $H_2O_2$ communication. When a population of synchronized colonies was exposed to a step increase of 200 U/ml catalase, an enzyme that rapidly degrades extracellular $H_2O_2$ (Seaver, et al., *J. Bacteriol.* (2001) 183:7182-7189), synchronization was broken and colonies continued to oscillate individually (FIG. 5). As the cell membrane is impermeable to catalase asynchronous colony oscillations confirm that communication between colonies depends on external $H_2O_2$ whereas oscillations within a colony do not. Conversely, when we enhanced the rate of superoxide conversion to $H_2O_2$ by expressing soda (Fridovich, et al., *Science* (1978) 201:875-880 (1978); McCord, et al., *J. Biol. Chem.* (1969) 244:6049-6055) from an additional lux promoter, colonies quickly fired in a spatial wave and failed to oscillate further despite no changes to growth rate or cell viability (FIG. 6). Because $H_2O_2$ is produced internal to the cell, this confirms that $H_2O_2$ is capable of escaping the cell and activating lux-regulated genes in neighboring colonies via diffusion. The apparent higher output of $H_2O_2$ by SOD as compared to NDH-2 is probably due to its very high catalytic efficiency (Berg, et al., Biochemistry (W.H. Freeman, 2006). Lastly, we observed synchronization between arrays of traps even when they were fluidically isolated but held in close proximity (FIG. 7). These devices share no common fluid sources or channels, making communication by dissolved molecules like AHL impossible. Taken together, these results confirm that gaseous $H_2O_2$ is the mode of communication between oscillating colonies.

Figure 8:
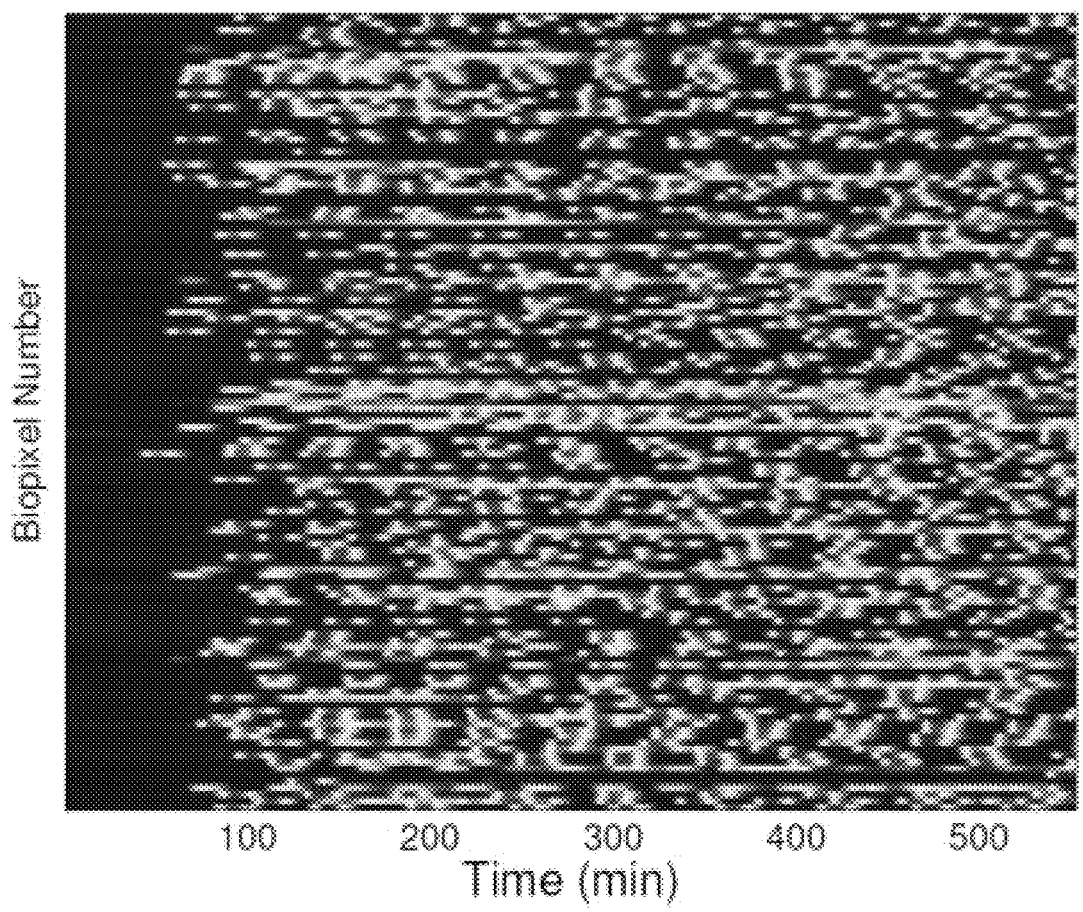
FIG. 8 illustrates a heatmap of trajectories extracted from low fluorescence intensity control when NDH-2 plasmid is not present. Biopixels oscillate individually but fail to synchronize.

On the basis of our understanding of the mechanism for global synchronization, we expected that we could simplify the circuitry by eliminating ndh and achieve the same effect with intermittent bursts of high-intensity blue light. In this design, the GFP molecule acts as a photosensitizer, releasing free radicals upon exposure that produce reactive oxygen species (ROS) including $H_2O_2$ (Remington, et al., *Curr. Opin. Struct. Biol.* (2006) 16:714-721). At the peak of oscillation, considerable vapor-phase $H_2O_2$ is produced by exposing GFP-containing cells to fluorescent light. Conversely, at the trough of oscillation, cells contain almost no GFP, and therefore produce very little $H_2O_2$ upon fluorescing. Bursts of light thus generate bursts of $H_2O_2$ vapor whose concentration depends on the oscillating GFP level, just as periodic production of NDH-2 did previously. Indeed, this strategy was similarly able to synchronize our sensor array (FIG. 1d). Numerous controls were performed to ensure that synchronized oscillations did not occur at low fluorescence intensities (FIG. 8).

Figure 9:
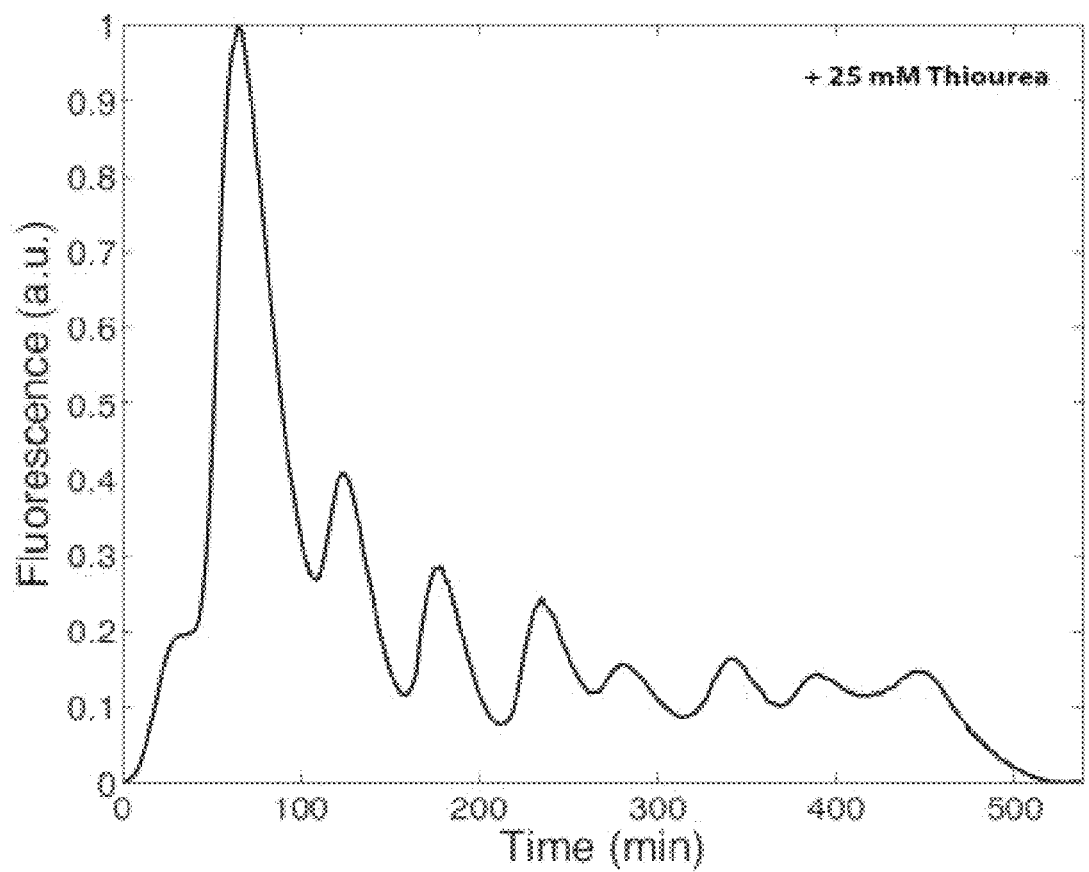
FIG. 9 illustrates that the introduction of thiourea, a potent radical quencher, produces decaying synchronized oscillations across a population of biopixels. Because radical species are precursors for $H_2O_2$, eliminating them lowers the production of $H_2O_2$ and therefore dampens the oscillations. Colonies are still able to synchronize because, while thiourea eliminates radicals within cells, it does not prevent $H_2O_2$ from diffusing between cells.
Figure 10:
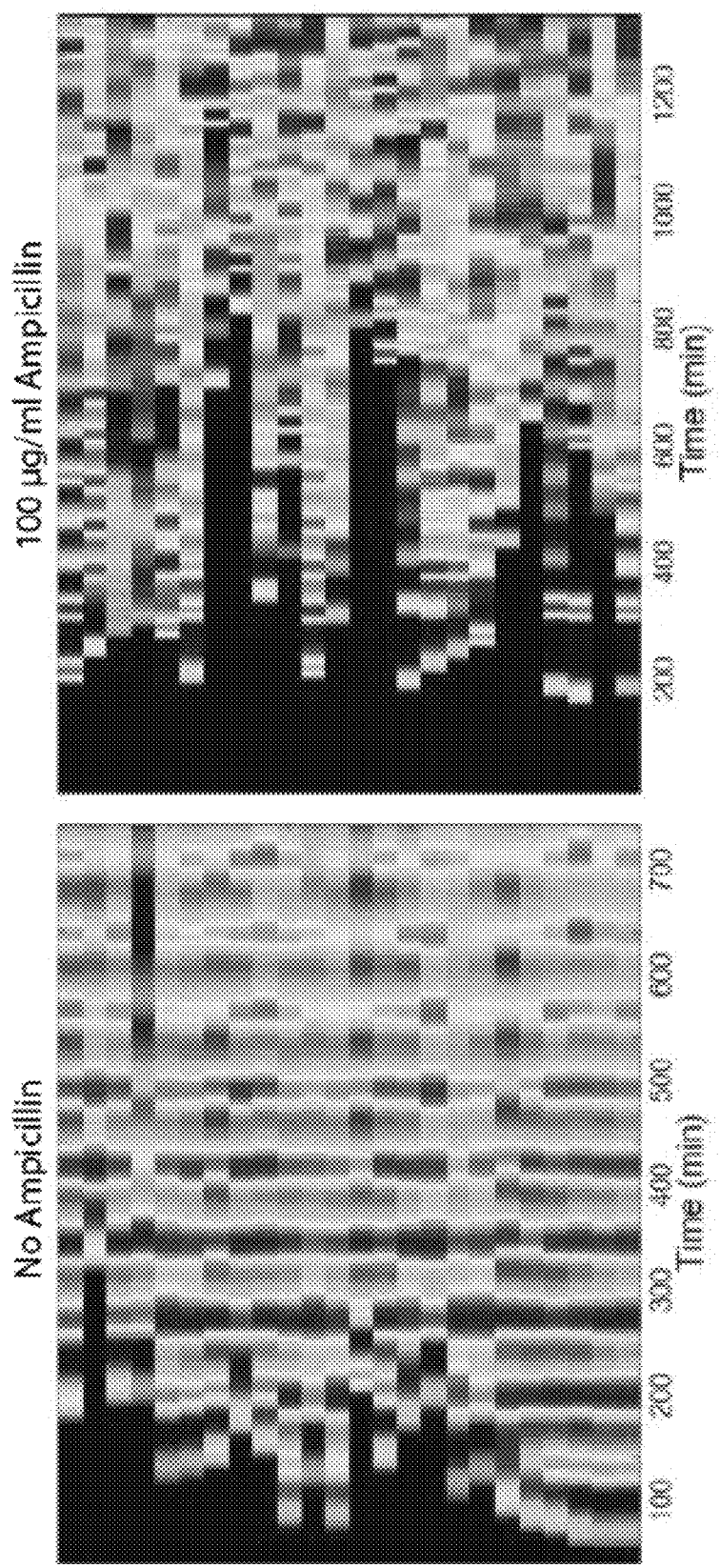
FIG. 10 illustrates that synchronization is prevented when 100 µg/ml Ampicillin is used in the media. The constructs, strains, and experimental conditions are otherwise identical.

To probe this mode of synchronization, we investigated the effects of thiourea and the antibiotics ampicillin and kanamycin. When a synchronized population of colonies was exposed to 35 mM thiourea, a potent radical quencher (Kelner, et al., *J. Biol. Chem.* (1990) 265:1306-1311; Touati, et al., *J. Bacteriol.* (1995) 177:2305-2314), we observed sharply decaying synchronized oscillations whereas growth rate and cell viability were unaffected (FIG. 9). This suggests that without radical species, oscillations cannot be produced. Next, we ran a series of experiments switching the antibiotic resistance genes on our plasmids. We noted that radical-producing antibiotics (Kohanski, et al., *Mol. Cell* (2010) 37:311-320), particularly ampicillin, significantly reduced the degree of synchronization, showing that an excess of radical species also hinders communication (FIG. 10). As our final constructs included a plasmid with kanamycin resistance, which was also found to produce some radicals, we used full (50 µg/ml) selection when growing up the cells but very low (5 µg/ml) selection during the experimental run. Persistence of oscillations, sequencing, and subsequent growth in full selection following the run confirmed the presence of all three plasmids despite this low experimental selection. Catalase and SOD results were identical to those with NDH-2 synchronization. These results show that fluorescence-mediated synchronization involves the production of radical species after fluorescence exposure and communication via $H_2O_2$.

Sensing Array of Biopixels

With a platform for generating consistent and readily detectable oscillations, we sought to use the circuit to engineer an arsenic-sensing macroscopic biosensor. We rewired the network to include an extra copy of the positive-feedback element, the AHL synthase LuxI, under the control of a native arsenite-responsive promoter that is repressed by ArsR in the absence of arsenite (FIG. 11a, right). When arsenite is not present in the media, supplementary luxI is not transcribed and the circuit functions normally, generating baseline oscillations. However, the addition of trace amounts of arsenite relieves this repression and allows supplementary luxI to be transcribed, increasing the oscillatory amplitude and period. Tuning the level of LuxI by varying arsenite concentration results in clear changes to the oscillatory period (FIG. 11b). To determine the range of detection, we swept arsenite concentrations from 0-1 mM and measured the oscillatory period (FIG. 11c, top). Using statistical methods, we generated a sensor calibration curve (FIG. 11c, bottom) that depicts the maximum possible arsenite concentration present (about 5.95%) for a given measured period. This curve is an illustration of how data generated by our array can be used to measure arsenite concentrations in an unknown sample using our device. Our system was able to reliably quantify arsenite levels as low as 0.2 mM, below the 0.5 mM World Health Organization-recommended level for developing nations (Nordstrom, *Science* (2002) 296:2143).

As an alternative sensing strategy, we rewired the network to include a copy of the luxR gene controlled by an arsenite-responsive promoter while removing it from the rest of the circuit (FIG. 11a, left). Because the LuxR-AHL complex must be present to activate the lux promoter (Waters, et al., *Annu. Rev. Cell Dev. Biol.* (2005) 21:319-346), cells produce no LuxR when the media is free of arsenite, generating no fluorescence or oscillations. The addition of arsenite stimulates the production of LuxR, restoring circuit function and producing clear, synchronized oscillations (FIG. 11d). This ON/OFF detection system has a threshold of 0.25 mM, a detection limit that can be adjusted by changing the copy number, ribosome binding site (RBS) strength, or promoter strength of the sensing plasmid.

Figure 13:
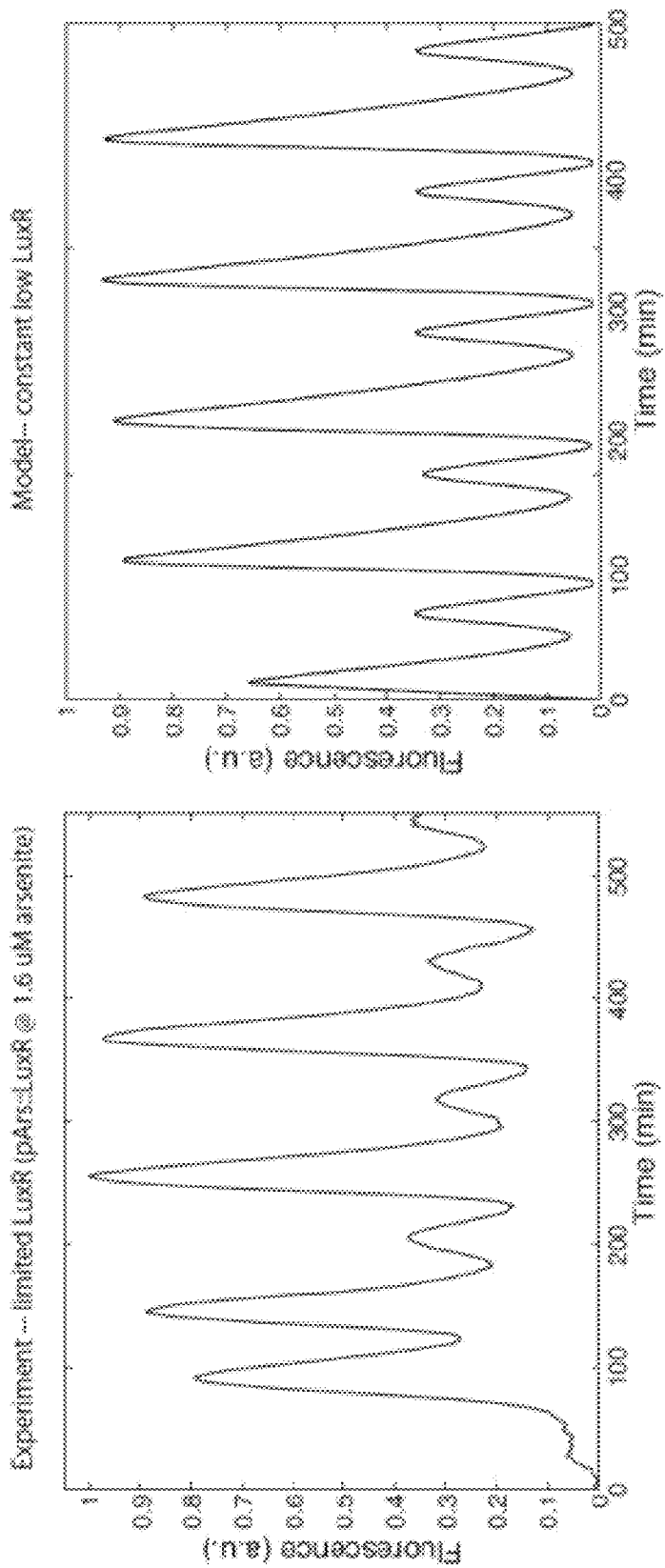
FIG. 13 illustrates oscillations of alternating large and small amplitude when LuxR is limited in experiments and simulations. The alternating oscillations vanish when LuxR is restored to its normal level in the model. Experimentally, we were unable to build a system in which LuxR is tunable between big/small and normal amplitude regimes. This is probably due to the small dynamic range of arsenite promoter-driven output of LuxR compared to the level produced by 3 constitutively expressed copies in the original circuit.

The sensing array is also capable of producing complex behaviors arising from the dynamic interaction of cellular colonies. By making modifications to the size, number and arrangement of biopixels in the device, we are able to markedly alter the output waveforms. For example, when we constructed a device in which trap separation distance is increased (45 mm versus 25 mm), we observed local anti-phase synchronization between neighboring colonies (FIG. 12d, top right). To explore this phenomenon on a larger scale, we constructed a device that contains an array of 416 traps constructed according to the specifications above. In these experiments, we observe initial global synchronization that gradually falls into local anti-phase synchronization across the array (FIG. 12d, middle). Phase alignment is maintained over at least 48 h, with patches of synchronization typically 3-6 colonies in size. Alternatively, by changing dimensions such that the array contains traps of two slightly different sizes, we observe a 1:2 resonance synchronization where larger traps pulse at double the frequency of smaller traps while maintaining synchronization (FIG. 12d, top left). Lastly, when LuxR is limited, as in the thresholding scheme, we observe synchronized oscillations of alternating large and small peaks in both experiment and model (FIG. 13). Our computational model captures these effects (FIG. 12d, bottom, and FIGS. 14 and 13) and indicates that further array manipulation will yield new, richer dynamics that could not be produced directly by changing circuit structure.

Figure 15:
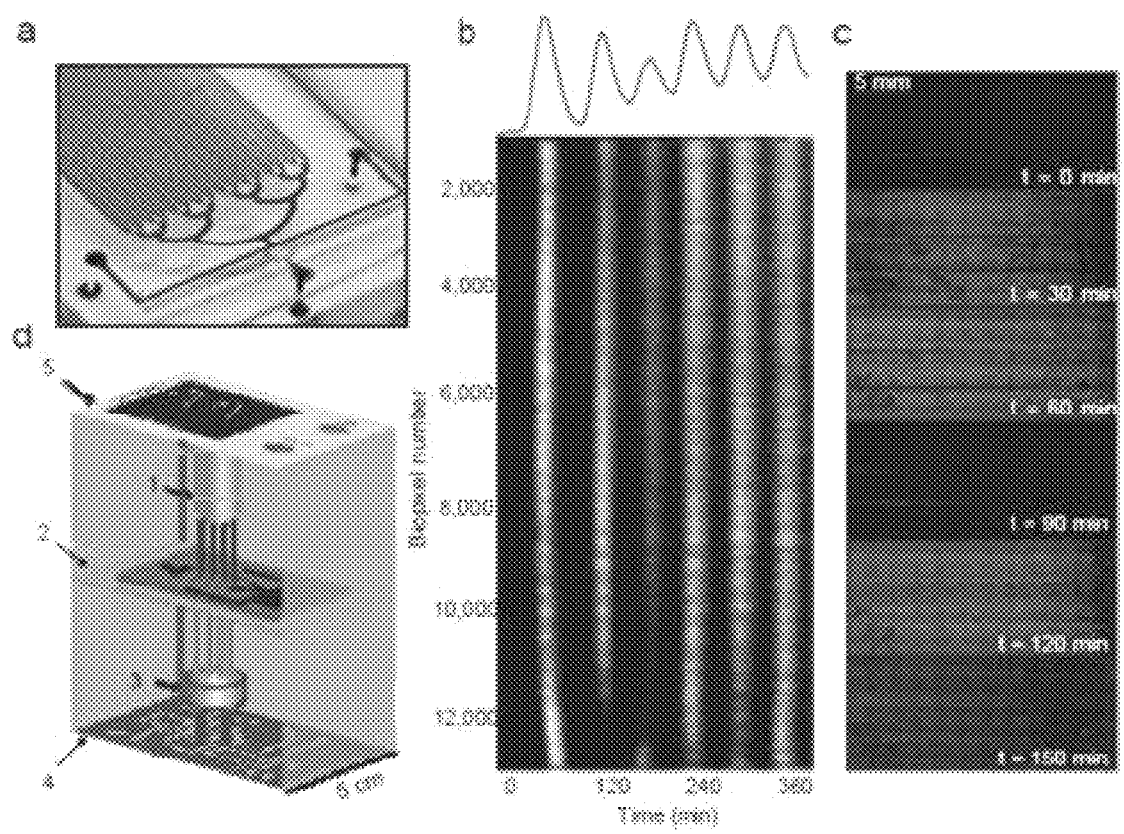
FIGS. 15A-D illustrate radical synchronization on a macroscopic scale. a, The scaled-up array is 24 mm×12 mm and houses over 12,000 biopixels that contain approximately 50 million total cells when filled. b, Global synchronization is maintained across the array. Heat map of individual trajectories of all 12,224 oscillating biopixels. c, Image series depicting global synchronization and oscillation for the macroscopic array. Each image is produced by stitching 72 fields of view imaged at 34 magnification. d, Schematic diagram illustrating our design for a handheld device using the sensing array. An LED (1) excites the array (2) and emitted light is collected by a photodetector (3), analysed by an onboard processor (4), and displayed graphically (5).

Although our sensor array is capable of performing a variety of complex functions in the laboratory, adapting this technology to a real-world device eliminates the expensive and bulky microscopy equipment. However, measuring genetic oscillations in the absence of any magnification or powerful illumination requires an even further increased signal. Using this mechanism of global synchronization, we were able to scale up to a 24 mm by 12 mm array that houses over 12,000 communicating biopixels (FIG. 15a). Synchronization is maintained across the entire array, a distance over 5,000 times the length of an individual cell, using an inexpensive light emitting diode (LED; FIG. 15b, c). The signal strength generated by the large number of cells in the array (about 50 million) allows adapting the device to function as a handheld sensor. In our design (FIG. 15d), the sensor continuously reads the oscillatory frequency using off-the-shelf electronic components costing less than 50 dollars.

There have been many examples of bacteria-based biosensors (van der Meer, et al., Nature Rev. Microbiol. (2010) 8:511-522 (2010); Daunert, et al., Chem. Rev. (2000) 100: 2705-2738; Leveau, et al., Curr. Opin. Microbiol. (2002) 5:259-265), usually involving an optical reporter driven by a toxin-responsive promoter. Because optical intensity readings are sensitive to imaging conditions like beam power and exposure time, measurements must typically be normalized and calibrated. Measuring the period of oscillation allows us to avoid these issues because peak-to-peak time does not depend on individual peak intensity. Also, oscillations produced at the colony level effectively decouple the signal from the growth state of individual cells, which can also affect fluorescence intensity. By using a dynamic readout that depends on communication between biopixels, we scan and tune potential output signals by changing device parameters rather than redesigning the underlying circuit. For example, a new sensing scheme could be designed in which oscillations synchronize with the addition of some toxin and shift to anti-phase or resonant synchronization when critical toxin levels are present.

Scaling up Synthetic Biology

By nesting two modes of communication we are able to expand the scale over which individual cells are coordinated and increase the complexity of their interaction. Indeed, there are many familiar examples of hierarchical systems. Airline routes are often designed such that small airports are connected locally to larger hubs that are connected internationally. It would neither be feasible nor desirable to connect every airport together. Similarly, individual cells communicate locally by one method, generating impulses large enough to enable colonies to communicate globally by another. Nesting communication mechanisms in this way allows us to better scale up synthetic circuits of different types, such as switches and logic gates.

Methods Summary

Strains and Plasmids.

The plasmids were constructed using a PCR-based cloning strategy (Quan, et al., PLoS ONE (2009) 4:e6441) in which the origin of replication, antibiotic resistance, and circuit genes were assembled in different combinations. The ndh and sodA genes were amplified directly from the native E. coli genome by PCR. Various arsenite-responsive promoters were tested, including a recently reported synthetic version (Stocker, et al., Environ. Sci. Technol. (2003) 37:4743-4750), but the final design uses the native E. coli version. Promoter output was tuned by changing the RBS sequence and quantified using flow cytometry. All circuit components except luxR were tagged by PCR with a carboxy-terminal ssrA tag (AANDENYALAA) (SEQ ID NO: 12) (Keiler, et al, Science (1996) 271:990-993) for fast degradation.

Microfluidics and Microscopy.

Image acquisition was performed on a Nikon Eclipse TI epifluorescent inverted microscope outfitted with fluorescence filter cubes optimized for GFP imaging and a phase-contrast-based autofocus algorithm. Images were acquired using an Andor Clara cooled CCD camera or Andor DU-897 EMCCD camera, both controlled by Nikon Elements software. Images were acquired every 2 min in phase contrast and fluorescence. The cells were imaged inside a microfluidic device with an upstream switch, with the ability to mix or switch between two different media sources. A custom application written in LabVIEW (National Instruments) controlled linear actuators, to which two reservoirs of arsenite-containing and pure medium were attached. Using this algorithm, arsenite concentration was dynamically varied to probe sensor output.

Plasmid Construction.

The oscillator plasmids were constructed by modifying the constructs used in a previous study (Danino, et al., Nature (2010) 463, 326-330). The antibiotic resistance genes of pTD103AiiA was switched to chloramphenicol. The reporter protein on pTD103LuxI/GFP was switched to a recently reported superfolding green fluorescent protein, sfGFP (Pedelacq, et al., Nature Biotechnology (2006) 24, 79-88). The ndh and sodA genes were amplified directly from the native E. coli genome by PCR. Promoter output was tuned by changing the RBS sequence and quantified using flow cytometry. We initially constructed the sensing plasmid with a published synthetic background-reduced version that contains additional ArsR operator sites (Stocker, J. et al. Environ. Sci. Technol (2003) 37, 4743-4750) but failed to produce enough LuxR. To increase LuxR output, we reverted to the native promoter sequence, switched the RBS to that of pZ plasmids, and increased the copy number by a factor of 5 by switching to a mutated SC101 origin of replication. All circuit components except LuxR were tagged by PCR with a carboxy-terminal ssrA tag (AANDE-NYALAA) (SEQ ID NO: 12) (Keiler, et al., Science (1996) 271, 990) for fast degradation. Modular pieces (resistance genes, promoters, origins, and ORFs) were assembled using a PCR-based cloning scheme named CPEC (Quan, J. and Tian, J., PloS one (2009) 4, e6441).

Data Analysis.

Fluorescence data was obtained by importing fluorescent images into ImageJ and subtracting cell signal from background signal. Oscillatory period was taken to be the average of peak-to-peak and trough-to-trough distance, calculated using a MATLAB script. The data represented in FIGS. 1d and 11b-d were collected by stitching 4 images taken at 4× magnification. The mean trajectory in FIG. 1d was found by averaging 373 individual biopixel trajectories, of which 20 are shown. Biopixel trajectories were extracted from image series using a MATLAB script, where a bright field image of the corresponding array was used to generate a mask. The data shown in FIG. 11c was measured over 4 separate experiments using 10-30 oscillatory periods per data point. Sensor calibration curve (FIG. 11c, bottom) was generated using a series of 2-population ttests comparing the experimental datasets to randomly generated new sample sets. The mean of generated sets was decremented until the ttest failed with $\alpha=95\%$, indicating the lowest period that could be associated with that arsenite concentration. We repeated this process for each arsenite level and fit the points with a quadratic since we expected it to take the inverse shape of the period vs. arsenite measurements.

Microscopy and Microfluidics.

We used a microscopy system similar to our recent studies (Danino, et al., Nature (2010) 463, 326-330), with the addition of a highsensitivity Andor DU-897 EMCCD camera. Fluorescent images were taken at 4× every 30 seconds using the EMCCD camera (20 ms exposure, 97% attenuation) or 2 minutes (2 s exposure, 90% attenuation) using a standard CCD camera to prevent photobleaching or phototoxicity.

In each device, E. coli cells are loaded from the cell port while keeping the media port at sufficiently higher pressure than the waste port below to prevent contamination (FIG. 10). Cells were loaded into the cell traps by manually applying pressure pulses to the lines to induce a momentary flow change. The flow was then reversed and allowed for cells to receive fresh media with 0.075% Tween which prevented cells from adhering to the main channels and waste ports. To measure fluid flow rate before each experiment, we measured the streak length of fluorescent beads (1.0 µm) upon 100 ms exposure to fluorescent light. We averaged at least 1,000 data points for each.

We constructed several microfluidic devices over the course of the study. The trap dimensions were 100 µm×85 µm×1.65 µm high, which we previously found to be useful for oscillator function, except when size was varied to study dynamic interactions. Spacing between traps was 25 µm, except in devices designed to study the effects of increasing separation distance between traps. For sensor array devices, we constructed 500 and 12,000 trap arrays as well as a tandem device which holds two 150 trap arrays in close proximity (25 µm) without sharing fluid sources or sinks.

Modeling.

To model the dynamics of the quorum-sensing oscillator, we used our previously described model for intracellular concentrations of LuxI (I), AiiA (A), internal AHL ($H_i$), and external AHL ($H_e$) (Danino, et al., Nature (2010) 463, 326-330), $$\frac{\partial A}{\partial t} = C_A[1-(d/d_0)^4]G(\alpha,\tau) - \frac{\gamma_A A}{1+f(A+I)} \quad (1)$$

$$\frac{\partial A}{\partial t} = C_I[1-(d/d_0)^4]G(\alpha,\tau) - \frac{\gamma_I A}{1+f(A+I)} \quad (2)$$

$$\frac{\partial H_i}{\partial t} = \frac{bI}{1+kI} - \frac{\gamma_H A H_i}{1+gA} + D(H_e - H_i) \quad (3)$$

$$\frac{\partial H_e}{\partial t} = \frac{d}{1-d} + D(H_e - H_i) - \mu H_e + D_1 \frac{\partial^2 H_e}{\partial x^2} \quad (4)$$

In the original model, the concentration of the constitutively produced LuxR protein R was assumed constant. In the ON/OFF threshold arsenic biosensor circuit, LuxR production is induced by arsenic, which we model by the equation $$\dot{R} = \frac{\alpha_c A}{(A_0+A)} - \gamma_R R \quad (5)$$

in which the LuxR expression from the arsenic promoter follows a standard saturating function of the arsenic concentration A. Accordingly, we modified the Hill function for Lux promoter to include the explicit dependence on R:

$$G(\alpha,\tau) = \frac{\delta + \alpha(R_\tau H_\tau)^2}{1+k_1(R_\tau H_\tau)^2} \quad (6)$$

For modeling the period-modulating sensor, we modified the equation for LuxI (2) to include additional production from the arsenic promoter, $$\dot{I} = C_I[1-(d/d_0)^4]G(\alpha,\tau) + \frac{\alpha_c A}{(A_0+A)} - \frac{\gamma_I I}{(1+f(A+I))} \quad (7)$$

The following additional parameters were used for the biosensor simulations: $\alpha_c=50$, $A_0=2$, $\gamma_R=0.1$.

Arsenic levels were swept across the dynamic range of the arsenic promoter to produce the curve in FIG. 11c. The period for each arsenic level was calculated from the peak-to-peak average of 15 oscillatory periods.

To model the spatial synchronization of oscillating colonies across a microfluidic array, we generalized a simplified "degrade-and-fire" model (Mather, et al., Physical Review Letters (2009) 102, 068105). The delay-differential equation $$\dot{X}_{i,j} = \frac{\alpha(1+\nu P_{i,j,\tau_2})}{\left(1+\frac{X_{i,j,\tau_1}}{C_0}\right)^2} - \frac{\gamma X_{i,j}}{k+X_{i,j}} \quad (8)$$

describes oscillations of individual biopixel (i,j) as a combined effect of production and delayed autorepression (first term in the r.h.s.) of the colon-averaged LuxI concentration $X_{i,j}$ and its enzymatic degradation by ClpXP (second term). Unlike (6), the first (production) term is Eq. 8 describes both delayed auto-repression of LuxI and its delayed activation by $H_2O_2$ proportional to its local concentration $P_{i,j}$. Subscripts $r_1$ and $r_2$ indicate the delayed concentrations, $X_{i,j,r_1}(t)=X_{i,j}(t-r_1)$ and $P_{i,j,r_2}(t)=P_{i,j}(t-r_2)$. The dynamics of $P_{i,j}$ is described by the equation $$\dot{P}_{i,j} = \mu + \alpha_p X_{i,j} - \gamma_p P_{i,j} + S(P_{i,j}) \quad (9)$$

where the first three terms describe the basal and induced production and degradation of $H_2O_2$. The last term models the spatial coupling of neighboring biopixels via the $H_2O_2$ exchange. For a square N×N array of traps, we used for the following discrete diffusion form of the spatial operator, $$\hat{S}(p_{i,j}) = D\Delta^{-2}[P_{i-1,j} + P_{i+1,j} + P_{i,j-1} + P_{i,j+} - 4P_{i,j}] \quad (10)$$

Each colony is affected by the $H_2O_2$ produced in for neighboring colonies, two in each dimension of the array, separated by the equal distance $\Delta$. We used the boundary condition $P_{i,j}=0$ for the edge of the array i,j=0, N+1. This represents the infinite external sink of $H_2O_2$ diffusing out of the microfluidic chip. The diffusion operator above can be generalized if the row spacing differs from the column spacing, or for other spatial arrangements of colonies within the biosensor.

We introduced variability among different traps by randomizing oscillator parameters for individual traps in each simulation. Specifically, LuxI (X) activation and degradation parameters (p={α,γ}) of each of the oscillators in the array were varied around their normal value ($p_0$) as $p=p_0+\delta$ where $\delta$ is a random number uniformly distributed between −0.25 and 0.25. We used the following dimensionless parameters for most of our simulations $\alpha_0=8.25$, $\gamma_0=5.75$, $v=1$, $r_2=10$, $r_2=20$, $C_0=6$, $k=10$, $\mu=20$, $\alpha_p 1$, $\gamma_P=10$, $D=7$, $\Delta=1$.

For the characterization of various regimes of array synchronization, 16 colonies were modeled in the 4×4 array. Scaling up the simulation with larger numbers of colonies produced equivalent results. Overproduction of $H_2O_2$ by expressing sodA was captured by increasing $\alpha_p$ 20-fold. This is consistent with expression from a pSC101m plasmid with a copy number of 20-30. Depletion of external $H_2O_2$ by catalase was modeled by increasing $H_2O_2$ degradation ($\gamma_p$) and decreasing $H_2O_2$ diffusion, D. In FIG. 3 we show the variance of the concentrations $X_{i,j}$ within the array averaged over time and parameter variations. This plot demonstrates that the synchronicity among the biopixels decreases with increase of spacing among them, and for $\Delta > 5$ is completely lost.

Increasing the trap spacing $\Delta$ 2-fold while simultaneously decreasing k 4-fold allowed us to reproduce the more complex waveforms observed experimentally in our arrays. Note that changing k models the change of the trap depth. As the size of the trap decreases, the flow of media is able to more rapidly sweep away AHL and increase the effective degradation for the colony. Simulating smaller and more sparse trap sizes recovered antiphase behavior for neighboring biopixels (FIG. 16). We also simulated the arrays with traps of two different sizes in different rows and recovered the experimental 2:1 biopixel resonance or 2:1+ antiphase behavior depending on the trap spacing (FIG. 12d, bottom).

Figure 14:
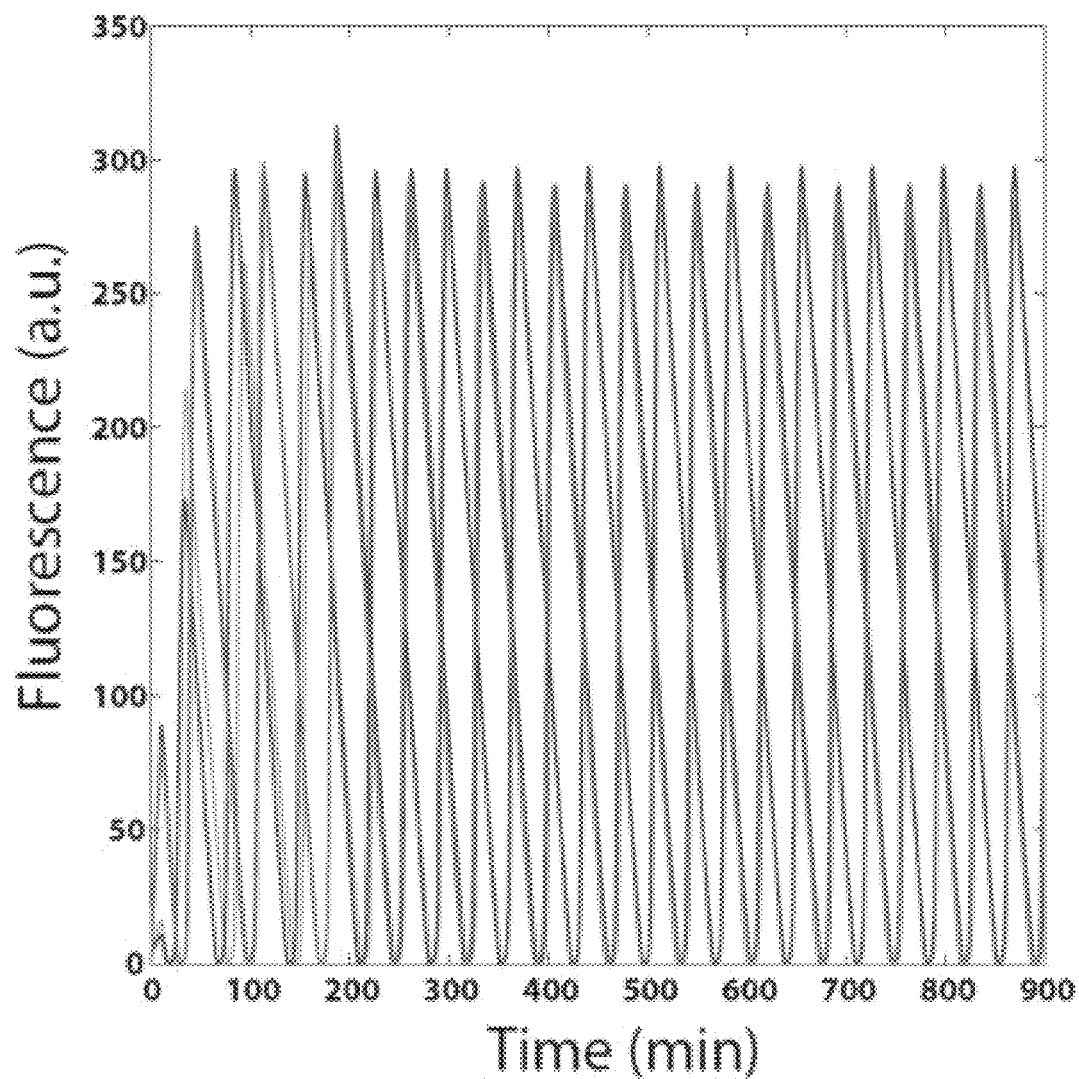
FIG. 14 illustrates antiphase behavior of 4 neighboring biopixels having equal trap sizes and spacing Δ=3.

The model was also able to capture the alternating large and small amplitude oscillations observed in the ON/OFF biosensor (FIG. 14). This behavior was seen when $C_0$ was increased 2-fold, capturing the decreased level of LuxR in ON/OFF experiments where it was the limiting factor for oscillations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A frequency-modulated biosensor, comprising a microfluidic array comprising two or more separate colonies of sensing cells which communicate by gas exchange, wherein the colonies of sensing cells output synchronized oscillating signals.

2. A kit comprising the biosensor of claim 1.

3. A method of detecting and/or measuring the levels of an analyte, comprising contacting a test sample suspected of comprising the analyte with the cells of the biosensor of claim 1, and measuring an oscillating signal output from the cells of the biosensor, thereby measuring the levels of the analyte.

4. A set of expression cassettes comprising:
   i) a LuxR gene under the control of a response element;
   ii) an aiiA gene under the control of a luxI promoter;
   iii) an acyl-homoserine lactone (AHL) synthase LuxI gene under the control of the luxI promoter; and
   iv) a nucleic acid encoding a protein that produces free radicals or oxygen reactive species under the control of the luxI promoter, wherein the set of expression cassettes comprises a thresholding sensor that produces an oscillating signal in a colony of cells in the presence of concentrations of an analyte above a threshold concentration, wherein the analyte binds to the response element.

5. The set of expression cassettes of claim 4, wherein the set of expression cassettes comprises a first expression cassette comprising at least 90% sequence identity to nucleic acid residues 27-756 of SEQ ID NO:1, a second expression cassette comprising at least 90% sequence identity to nucleic acid residues 901-1744 of SEQ ID NO:1, a third expression cassette comprising at least 90% sequence identity to nucleic acid residues 10-913 of SEQ ID NO:2, and a fourth expression cassette comprising at least 90% sequence identity to nucleic acid residues 7-1366 of SEQ ID NO:3.

6. The set of expression cassettes of claim 4, wherein the set of expression cassettes comprises a first expression cassette comprising at least 90% sequence identity to nucleic acid residues 27-756 of SEQ ID NO:1, a second expression cassette comprising at least 90% sequence identity to nucleic acid residues 901-1744 of SEQ ID NO:1, a third expression cassette comprising at least 90% sequence identity to nucleic acid residues 10-913 of SEQ ID NO:2, and a fourth expression cassette comprising at least 90% sequence identity to nucleic acid residues 7-788 of SEQ ID NO:7 or at least 90% sequence identity to nucleic acid residues 7-790 of SEQ ID NO:8.

7. A set of expression cassettes comprising:
   i) an acyl-homoserine lactone (AHL) synthase LuxI gene under the control of a response element;
   ii) a LuxR gene under the control of a luxR promoter and an aiiA gene under the control of a luxI promoter;
   iii) a LuxR gene under the control of a luxR promoter and a nucleic acid encoding a protein that produces free radicals or oxygen reactive species under the control of a luxI promoter; and
   iv) a LuxR gene under the control of a luxR promoter and a LuxI gene under the control of a luxI promoter, wherein the set of expression cassettes comprise a period modulation sensor that produces a changed oscillating signal in a population of cells in the presence of concentrations of an analyte above a threshold concentration, wherein the analyte binds to the response element.

8. The set of expression cassettes of claim 7, wherein the changed oscillating signal comprises increased oscillatory amplitude and period.

9. The set of expression cassettes of claim 7, wherein the set of expression cassettes comprises a first expression cassette comprising at least 90% sequence identity to nucleic acid residues 7-1795 of SEQ ID NO:4, a second expression cassette comprising at least 90% sequence identity to nucleic acid residues 1895-3488 of SEQ ID NO:4, a third expression cassette comprising at least 90% sequence identity to nucleic acid residues 10-1771 of SEQ ID NO:5, and a fourth expression cassette comprising at least 90% sequence identity to nucleic acid residues 1-1203 of SEQ ID NO:6.

10. The set of expression cassettes of claim 9, wherein the set of expression cassettes further comprises an expression cassette comprising at least 90% sequence identity to nucleic acid residues 1-641 of SEQ ID NO:10 or at least 90% sequence identity to nucleic acid residues 1-643 of SEQ ID NO:11.

11. The set of expression cassettes of claim 7, wherein the set of expression cassettes comprises a first expression cassette comprising at least 90% sequence identity to nucleic acid residues 7-1795 of SEQ ID NO:4, a second expression cassette comprising at least 90% sequence identity to nucleic acid residues 1895-3488 of SEQ ID NO:4, a third expression cassette comprising at least 90% sequence identity to nucleic acid residues 10-1771 of SEQ ID NO:5, and a fourth expression cassette comprising at least 90% sequence identity to nucleic acid residues 1-641 of SEQ ID NO:10 or at least 90% sequence identity to nucleic acid residues 1-643 of SEQ ID NO:11.

12. The set of expression cassettes of claim 11, wherein one or more of the expression cassettes comprise an arcA binding sequence within 150 bp of the LuxR gene, the LuxI gene and/or the nucleic acid encoding a protein that produces free radicals or oxygen reactive species.

13. The set of expression cassettes of claim 4, wherein the response element is selected from the group consisting of an arsenite response element (pArsR), a cadmium response element (yodA/cadA/cadR), a copper response element (copA/cueR), a mercury response element (merR), a cobalt response element, a lead response element, a zinc response element, a cyanide response element (CNO), a microcystin response element (mlrABCD), and an organophosphorus (OP) neurotoxin response element.

14. The set of expression cassettes of claim 4, wherein the nucleic acid encoding a protein that produces free radicals or oxygen reactive species encodes a fluorescent protein.

15. The set of expression cassettes of claim 14, wherein the protein that produces free radicals or oxygen reactive species is selected from the group consisting of a green fluorescent protein, a yellow fluorescent protein, a cyan fluorescent protein, a red-shifted green fluorescent protein (rs-GFP), and miniSOG.

16. One or more plasmids comprising the set of expression cassettes of claim 4.

17. A cell comprising the set of expression cassettes of claim 4.

18. The cell of claim 17, wherein the cell is an *E. coli* cell.

19. Two or more colonies of cells comprising the set of expression cassettes of claim 4, wherein the colonies of cells communicate with each other via gas or vapor phase and produce synchronized oscillating output signals.

20. A microfluidic array comprising the cell of claim 17.

21. A biosensor comprising the cell of claim 17.

22. The set of expression cassettes of claim 4, wherein the set of expression cassettes comprises:
   i) a LuxR gene under the control of an arsenite response element (pArsR);
   ii) an aiiA gene under the control of a luxI promoter;
   iii) an acyl-homoserine lactone (AHL) synthase LuxI gene under the control of the luxI promoter; and
   iv) a nucleic acid encoding a protein that produces free radicals or oxygen reactive species under the control of the luxI promoter.

23. The set of expression cassettes of claim 4, wherein the set of expression cassettes comprises:
   i) a LuxR gene under the control of a cadmium response element (yodA/cadA/cadR);
   ii) an aiiA gene under the control of a luxI promoter;
   iii) an acyl-homoserine lactone (AHL) synthase LuxI gene under the control of the luxI promoter; and
   iv) a nucleic acid encoding a protein that produces free radicals or oxygen reactive species under the control of the luxI promoter.

24. The set of expression cassettes of claim 4, wherein the set of expression cassettes comprises:
   i) a LuxR gene under the control of an arsenite response element (pArsR);
   ii) a LuxR gene under the control of a cadmium response element (yodA/cadA/cadR);
   iii) an aiiA gene under the control of a luxI promoter;
   iv) an acyl-homoserine lactone (AHL) synthase LuxI gene under the control of the luxI promoter; and
   v) a nucleic acid encoding a protein that produces free radicals or oxygen reactive species under the control of the luxI promoter.

25. The biosensor of claim 1, wherein the colonies of sensing cells are selected from the group consisting of microbial cells, bacterial cells, yeast cells, mammalian cells, insect cells, photosynthetic cells, and plant cells.

26. The biosensor of claim 1, wherein thousands of oscillating cell colonies are operatively coupled in the microfluidic array.

27. The biosensor of claim 1, wherein the degree to which neighboring colonies influence each other via fluid diffusion is negligible.

28. The biosensor of claim 1, wherein the colonies of sensing cells output synchronized oscillating signals of approximately 2.5 million cells across a distance of about 5 mm.

29. The biosensor of claim 1, wherein the colonies of sensing cells are comprised in two or more microfluidic arrays that share no common fluid sources or channels.

30. The biosensor of claim 1, wherein the microfluidic array comprises oxygen-permeable polydimethylsiloxane (PDMS) walls.

31. The biosensor of claim 1, wherein the colonies of sensing cells are bacterial cells and the operative or intercellular coupling or communication of the cell colonies comprises redox signaling by hydrogen peroxide ($H_2O_2$).

32. The biosensor of claim 1, wherein the bacterial cells are *E. coli* cells.

33. The biosensor of claim 1, wherein the cells comprise a copy of a gene coding for NADH dehydrogenase II (ndh) under the control of a luxI promoter.

34. The biosensor of claim 1, wherein the cells comprise a copy of the gene coding for green fluorescent protein (GFP) under the control of a luxI promoter.

35. The biosensor of claim 1, wherein the cells comprise a copy of acyl-homoserine lactone (AHL) synthase LuxI, under the control of a native arsenite-responsive promoter that is repressed by ArsR in the absence of arsenite.

36. The biosensor of claim 1, wherein the cells comprise a luxR gene or an acyl-homoserine lactone (AHL) synthase LuxI gene controlled by response element selected from the group consisting of an arsenite response element (pArsR), a cadmium response element (yodA/cadA/cadR), a copper response element (copA/cueR), a mercury response element (merR), a cobalt response element, a lead response element, a zinc response element, a cyanide response element (CNO), a microcystin response element (mlrABCD), and an organophosphorus (OP) neurotoxin response element.

37. The biosensor of claim 1, wherein the colonies of cells comprise a set of expression cassettes comprising:
   i) a LuxR gene under the control of a response element;
   ii) an aiiA gene under the control of a luxI promoter;
   iii) an acyl-homoserine lactone (AHL) synthase LuxI gene under the control of the luxI promoter; and
   iv) a nucleic acid encoding a protein that produces free radicals or oxygen reactive species under the control of the luxI promoter, wherein the colonies of cells comprise a thresholding sensor that produces an oscillating signal in the presence of concentrations of an analyte above a threshold concentration, wherein the analyte binds to the response element.

38. The method of claim 3, wherein the analyte is a small molecule.

39. The method of claim 38, wherein the small molecule is a small inorganic molecule.

40. The method of claim 3, wherein the analyte is selected from the group consisting of arsenic, cadmium, copper, mercury, cobalt, lead, zinc, cyanide, a cyanobacterial microcystin, and an organophosphorus (OP) neurotoxin.

41. The method of claim 3, wherein a presence of the oscillating signal output indicates the detection of the analyte.

42. The method of claim 3, wherein increased frequency and amplitude of the oscillating signal output indicates the detection of the analyte.

43. The method of claim 3, wherein the test sample is blood, water or air.

44. The method of claim 38, wherein the small molecule is a small organic molecule.

45. The method of claim 3, wherein the analyte is a peptide, a carbohydrate or a nucleic acid.

* * * * *

SEQUENCE LISTING

<160> NUMBER OF SEQ ID NOS: 12

<210> SEQ ID NO 1
<211> LENGTH: 3849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ctcgagagtc tataccgatg acgacgacta ttgtatcgct gggaatacaa ttacttaaca      60
taagcacctg taggatcgta caggtttacg caagaaaatg gtttgttata gtcgaatgaa     120
ttcattaaag aggagaaagg taccatgact ataatgataa aaaaatcgga tttttggca     180 attccatcgg aggagtataa aggtattcta agtcttcgtt atcaagtgtt taagcaaaga     240
cttgagtggg acttagttgt agaaaataac cttgaatcag atgagtatga taactcaaat     300
gcagaatata tttatgcttg tgatgatact gaaaatgtaa gtggatgctg gcgtttatta     360
cctacaacag gtgattatat gctgaaaagt gtttttcctg aattgcttgg tcaacagagt     420
gctcccaaag atcctaatat agtcgaatta agtcgttttg ctgtaggtaa aaatagctca     480
aagataaata actctgctag tgaaattaca atgaaactat ttgaagctat atataaacac     540
gctgttagtc aaggtattac agaatatgta acagtaacat caacagcaat agagcgattt     600
ttaaagcgta ttaaagttcc ttgtcatcgt attggagaca aagaaattca tgtattaggt     660
gatactaaat cggttgtatt gtctatgcct attaatgaac agtttaaaaa agcagtctta     720
aatgcagcga acgacgaaaa ttacgccctt gcagcgtaaa cgcgtgctag aggcatcaaa     780
taaaacgaaa ggctcagtcg aaagactggg cctttcgttt tatctgttgt ttgtcggtga     840
acgctctcct gagtaggaca aatccgccgc cctagaagac tgtcgctaca gatagttcac     900
actattgtat cgctgggaat acaattactt aacataagca cctgtaggat cgtacaggtt     960
tacgcaagaa aatggtttgt tatagtcgaa tgaattcatt aaagaggaga aaggtaccat    1020
gagcaaagga gaagaacttt tcactggagt tgtcccaatt cttgttgaat tagatggtga    1080
tgttaatggg cacaaatttt ctgtccgtgg agagggtgaa ggtgatgcta caaacggaaa    1140
```

```
actcacccctt aaatttattt gcactactgg aaaactacct gttccgtggc caacacttgt    1200
cactactctg acctatggtg ttcaatgctt ttcccgttat ccggatcaca tgaaacggca    1260 tgacttttc aagagtgcca tgcccgaagg ttatgtacag gaacgcacta tatctttcaa    1320
agatgacggg acctacaaga cgcgtgctga agtcaagttt gaaggtgata cccttgttaa    1380
tcgtatcgag ttaaagggta ttgattttaa agaagatgga acattcttg  gacacaaact    1440 cgagtacaac tttaactcac acaatgtata catcacggca gacaaacaaa gaatggaat    1500 caaagctaac ttcaaaattc gccacaacgt tgaagatggt tccgttcaac tagcagacca    1560
ttatcaacaa atactccaa ttggcgatgg ccctgtcctt ttaccagaca accattacct    1620
gtcgacacaa tctgtccttt cgaaagatcc caacgaaaag cgtgaccaca tggtccttct    1680
tgagtttgta actgctgctg ggattacaca tggcatggat gagctctaca aaactagtgc    1740
agcgaacgac gaaaattacg cccttgcagc gtgaacgcgt gctagaggca tcaaataaaa    1800
cgaaaggctc agtcgaaaga ctgggccttt cgttttatct gttgtttgtc ggtgaacgct    1860
ctcctgagta ggacaaatcc gccgccctag acctaggggcg ttcggctgcg gcgagcggta    1920
tcagctcact caaaggcggt aatacggtta tccacagaat caggggataa cgcaggaaag    1980
aacatgtgag caaaaggcca gcaaaaggcc aggaaccgta aaaaggccgc gttgctggcg    2040 ttttttccata ggctccgccc ccctgacgag catcacaaaa atcgacgctc aagtcagagg    2100
tggcgaaacc cgacaggact ataaagatac caggcgtttc cccctggaag ctccctcgtg    2160
cgctctcctg ttccgaccct gccgcttacc ggatacctgt ccgcctttct cccttcggga    2220
agcgtggcgc tttctcatag ctcacgctgt aggtatctca gttcggtgta ggtcgttcgc    2280
tccaagctgg gctgtgtgca cgaaccccc  gttcagcccg accgctgcgc cttatccggt    2340
aactatcgtc ttgagtccaa cccggtaaga cacgacttat cgccactggc agcagccact    2400
ggtaacagga ttagcagagc gaggtatgta ggcggtgcta cagagttctt gaagtggtgg    2460
cctaactacg gctacactag aaggacagta tttggtatct gcgctctgct gaagccagtt    2520
accttcggaa aaagagttgg tagctcttga tccggcaaac aaaccaccgc tggtagcggt    2580
ggtttttttg tttgcaagca gcagattacg cgcagaaaaa aaggatctca agaagatcct    2640
ttgatctttt ctacggggtc tgacgctcag tggaacgaaa actcacgtta agggattttg    2700
gtcatgacta gtgcttggat tctcaccaat aaaaaacgcc cggcggcaac cgagcgttct    2760
gaacaaatcc agatggagtt ctgaggtcat tactggatct atcaacagga gtccaagcga    2820
gctctcgaac cccagagtcc cgctcagaag aactcgtcaa gaaggcgata gaaggcgatg    2880
cgctgcgaat cgggagcggc gataccgtaa agcacgagga agcggtcagc ccattcgccg    2940
ccaagctctt cagcaatatc acgggtagcc aacgctatgt cctgatagcg gtccgccaca    3000
cccagccggc cacagtcgat gaatccagaa aagcggccat tttccaccat gatattcggc    3060
aagcaggcat cgccatgggt cacgacgaga tcctcgccgt cgggcatgcg cgccttgagc    3120
ctggcgaaca gttcggctgg cgcgagcccc tgatgctctt cgtccagatc atcctgatcg    3180
acaagaccgg cttccatccg agtacgtgct cgctcgatgc gatgtttcgc ttggtggtcg    3240
aatgggcagg tagccggatc aagcgtatgc agccgccgca ttgcatcagc catgatggat    3300
actttctcgg caggagcaag gtgagatgac aggagatcct gccccggcac ttcgcccaat    3360
agcagccagt cccttcccgc ttcagtgaca acgtcgagca cagctgcgca aggaacgccc    3420
gtcgtggcca gccacgatag ccgcgctgcc tcgtcctgca gttcattcag gcaccggac    3480 aggtcggtct tgacaaaaag aaccgggcgc ccctgcgctg acagccggaa cacggcggca    3540
```

| | |
|---|---|
| tcagagcagc cgattgtctg ttgtgcccag tcatagccga atagcctctc cacccaagcg | 3600 |
| gccggagaac ctgcgtgcaa tccatcttgt tcaatcatgc gaaacgatcc tcatcctgtc | 3660 |
| tcttgatcag atcttgatcc cctgcgccat cagatccttg gcggcaagaa agccatccag | 3720 |
| tttactttgc agggcttccc aaccttacca gagggcgccc cagctggcaa ttccgacgtc | 3780 |
| taagaaacca ttattatcat gacattaacc tataaaaata ggcgtatcac gaggcccttt | 3840 |
| cgtcttcac | 3849 |

<210> SEQ ID NO 2
<211> LENGTH: 3047
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2

| | |
|---|---|
| ctcgagttaa ctattgtatc gctgggaata caattactta acataagcac ctgtaggatc | 60 |
| gtacaggttt acgcaagaaa atggtttgtt atagtcgaat gaattcatta agaggagaa | 120 |
| aggtaccatg acagtaaaga aactttattt catcccagcg ggtcgttgca tgttggatca | 180 |
| ttcgtctgtt aacagtgcgt taacaccggg gaaactatta aacttgccgg tgtggtgtta | 240 |
| tcttttggag acggaagaag gtcctatttt agtagacaca ggtatgccag aaagtgcagt | 300 |
| taataatgaa gggcttttta acggtacatt tgttgaagga cagatcttac cgaaaatgac | 360 |
| tgaagaagat agaatcgtga atatattaaa gcgtgtaggg tatgagccgg acgacctttt | 420 |
| atatattatt agttctcact tacattttga tcatgcagga ggaaacggtg ctttacaaaa | 480 |
| tacaccaatt attgtgcagc gaacggaata tgaggcagca cttcatagag aagaatatat | 540 |
| gaaagaatgt atattaccgc atttgaacta caaaattatt gaaggggatt atgaagtggt | 600 |
| accaggtgtt caattattgt atacgccagg tcattctcca ggccatcagt cgctattcat | 660 |
| tgagacggag caatccggtt cagttttatt aacgattgat gcatcgtaca cgaaagagaa | 720 |
| ttttgaagat gaagtgccgt tcgcaggatt tgatccagaa ttagctttat cttcaattaa | 780 |
| acgtttaaaa gaagttgtga aaaagagaa accaattatt ttctttggtc atgatataga | 840 |
| gcaggaaaag agttgtagag tgttcccgga atatatagca gcgaacgacg aaaattacgc | 900 |
| ccttgcagcg taaacgcgtg ctagaggcat caaataaaac gaaaggctca gtcgaaagac | 960 |
| tgggcctttc gttttatctg ttgtttgtcg gtgaacgctc tcctgagtag acaaatccg | 1020 |
| ccgccctaga cctagggcgt tcggctgcgg cgagcggtat cagctcactc aaaggcggta | 1080 |
| atacggttat ccacagaatc agggataac gcaggaaaga acatgtgagc aaaaggccag | 1140 |
| caaaaggcca ggaaccgtaa aaaggccgcg ttgctggcgt ttttccatag gctccgcccc | 1200 |
| cctgacgagc atcacaaaaa tcgacgctca agtcagaggt ggcgaaaccc gacaggacta | 1260 |
| taaagatacc aggcgtttcc ccctggaagc tccctcgtgc gctctcctgt tccgaccctg | 1320 |
| ccgcttaccg gatacctgtc cgcctttctc ccttcgggaa gcgtggcgct ttctcatagc | 1380 |
| tcacgctgta ggtatctcag ttcggtgtag gtcgttcgct ccaagctggg ctgtgtgcac | 1440 |
| gaaccccccg ttcagcccga ccgctgcgcc ttatccggta actatcgtct tgagtccaac | 1500 |
| ccggtaagac acgacttatc gccactggca gcagccactg gtaacaggat tagcagagcg | 1560 |
| aggtatgtag gcggtgctac agagttcttg aagtggtggc ctaactacgg ctacactaga | 1620 |
| aggacagtat ttggtatctg cgctctgctg aagccagtta ccttcggaaa aagagttggt | 1680 |

```
agctcttgat ccggcaaaca aaccaccgct ggtagcggtg gttttttttgt ttgcaagcag    1740 cagattacgc gcagaaaaaa aggatctcaa gaagatcctt tgatcttttc tacggggtct    1800
gacgctcagt ggaacgaaaa ctcacgttaa gggattttgg tcatgactag tgcttggatt    1860
ctcaccaata aaaaacgccc ggcggcaacc gagcgttctg aacaaatcca gatggagttc    1920
tgaggtcatt actggatcta tcaacaggag tccaagcgag ctcgtaaact tggtctgaca    1980
gttaccaatg cttaatcagt gaggcaccta tctcagcgat ctgtctattt cgttcatcca    2040
tagttgcctg actccccgtc gtgtagataa ctacgatacg ggagggctta ccatctggcc    2100
ccagtgctgc aatgataccg cgagacccac gctcaccggc tccagattta tcagcaataa    2160
accagccagc cggaagggcc gagcgcagaa gtggtcctgc aactttatcc gcctccatcc    2220
agtctattaa ttgttgccgg gaagctagag taagtagttc gccagttaat agtttgcgca    2280
acgttgttgc cattgctaca ggcatcgtgg tgtcacgctc gtcgtttggt atggcttcat    2340
tcagctccgg ttcccaacga tcaaggcgag ttacatgatc ccccatgttg tgcaaaaaag    2400
cggttagctc cttcggtcct ccgatcgttg tcagaagtaa gttggccgca gtgttatcac    2460
tcatggttat ggcagcactg cataattctc ttactgtcat gccatccgta agatgctttt    2520
ctgtgactgg tgagtactca accaagtcat tctgagaata gtgtatgcgg cgaccgagtt    2580
gctcttgccc ggcgtcaata cgggataata ccgcgccaca tagcagaact ttaaaagtgc    2640
tcatcattgg aaaacgttct cggggcgaaa actctcaag gatcttaccg ctgttgagat    2700
ccagttcgat gtaacccact cgtgcaccca actgatcttc agcatctttt actttcacca    2760
gcgtttctgg gtgagcaaaa acaggaaggc aaaatgccgc aaaaaaggga ataagggcga    2820
cacggaaatg ttgaatactc atactcttcc tttttcaata ttattgaagc atttatcagg    2880
gttattgtct catgagcgga tacatatttg aatgtattta gaaaaataaa caaatagggg    2940
ttccgcgcac atttccccga aaagtgccac ctgacgtcta agaaaccatt attatcatga    3000
cattaaccta taaaaatagg cgtatcacga ggccctttcg tcttcac                  3047
```

<210> SEQ ID NO 3
<211> LENGTH: 4833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gacgtctttc caagttatct cacctacctt aaggtaatag tgtgattaat catatgcgtt     60
tttggttatg tgttgtttga cttaatatca gagccgagag atacttgttt tctacaaagg    120
agagggaaat gttgcaacta acaccacttc agttatttaa aaacctgtcc gatgaaaccc    180
gtttgggtat cgtgttgttg ctcagggaga tgggagagtt gtgcgtgtgt gatctttgca    240
tggcactgga tcaatcacag cccaaaatat cccgtcatct ggcgatgcta cgggaaagtg    300
gaatccttct ggatcgtaaa cagggaaaat gggttcacta ccgcttatca ccgcatattc    360
cttcatgggc tgcccagatt attgagcagg cctggttaag ccaacaggac gacgttcagg    420
tcatcgcacg caagctggct tcagttaact gctccggtag cagtaaggct gtctgcatct    480
aaaaaatttg cctgaacata tatgttttat caaatgcgag gtatttaaga tgaaaacgtt    540
aatggtattt gacccggcga tgtgttgcag caccggtatc actagagaat tcattaaaga    600
ggagaaaggt accatgaaaa acataaatgc cgacgacaca tacagaataa ttaataaaat    660
```

```
taaagcttgt agaagcaata atgatattaa tcaatgctta tctgatatga ctaaaatggt    720
acattgtgaa tattatttac tcgcgatcat ttatcctcat tctatggtta aatctgatat    780
ttcaattcta gataattacc ctaaaaaatg gaggcaatat tatgatgacg ctaatttaat    840
aaaatatgat cctatagtag attattctaa ctccaatcat tcaccaatta attggaatat    900
atttgaaaac aatgctgtaa ataaaaaatc tccaaatgta attaaagaag cgaaaacatc    960
aggtcttatc actgggttta gtttccctat tcatacggct aacaatggct tcggaatgct   1020
tagttttgca cattcagaaa aagacaacta tatagatagt ttatttttac atgcgtgtat   1080
gaacatacca ttaattgttc cttctctagt tgataattat cgaaaaataa atatagcaaa   1140
taataaatca aacaacgatt taaccaaaag agaaaaagaa tgtttagcgt gggcatgcga   1200
aggaaaaagc tcttgggata tttcaaaaat attaggctgc agtgagcgta ctgtcacttt   1260
ccatttaacc aatgcgcaaa tgaaactcaa tacaacaaac cgctgccaaa gtatttctaa   1320
agcaatttta acaggagcaa ttgattgccc atactttaaa aattaaacgc gtgctagagg   1380
catcaaataa aacgaaaggc tcagtcgaaa gactgggcct ttcgttttat ctgttgtttg   1440
tcggtgaacg ctctcctgag taggacaaat ccgccgccct agacctaggg tacgggtttt   1500
gctgcccgca aacgggctgt tctggtgttg ctagtttgtt atcagaatcg cagatccggc   1560
ttcaggtttg ccggctgaaa gcgctatttc ttccagaatt gccatgattt ttccccacg    1620
ggaggcgtca ctggctcccg tgttgtcggc agctttgatt cgataagcag catcgcctgt   1680
ttcaggctgt ctatgtgtga ctgttgagct gtaacaagtt gtctcaggtg ttcaatttca   1740
tgttctagtt gctttgtttt actggtttca cctgttctat taggtgttac atgctgttca   1800
tctgttacat tgtcgatctg ttcatggtga acagctttaa atgcaccaaa aactcgtaaa   1860
agctctgatg tatctatctt ttttacaccg ttttcatctg tgcatatgga cagttttccc   1920
tttgatatct aacggtgaac agttgttcta cttttgtttg ttagtcttga tgcttcactg   1980
atagatacaa gagccataag aacctcagat ccttccgtat ttagccagta tgttctctag   2040
tgtggttcgt tgttttttgcg tgagccatga gaacgaacca ttgagatcat gcttactttg   2100
catgtcactc aaaaattttg cctcaaaact ggtgagctga attttttgcag ttaaagcatc   2160
gtgtagtgtt tttcttagtc cgttacgtag gtaggaatct gatgtaatgg ttgttggtat   2220
tttgtcacca ttcattttta tctggttgtt ctcaagttcg gttacgagat ccatttgtct   2280
atctagttca acttggaaaa tcaacgtatc agtcgggcgg cctcgcttat caaccaccaa   2340
tttcatattg ctgtaagtgt ttaaatcttt acttattggt ttcaaaaccc attggttaag   2400
ccttttaaac tcatggtagt tattttcaag cattaacatg aacttaaatt catcaaggct   2460
aatctctata tttgccttgt gagttttctt ttgtgttagt tcttttaata accactcata   2520
aatcctcata gagtatttgt tttcaaaaga cttaacatgt tccagattat attttatgaa   2580
tttttttaac tggaaaagat aaggcaatat ctcttcacta aaaactaatt ctaatttttc   2640
gcttgagaac ttggcatagt ttgtccactg gaaaatctca aagcctttaa ccaaaggatt   2700
cctgatttcc acagttctcg tcatcagctc tctggttgct ttagctaata caccataagc   2760
attttcccta ctgatgttca tcatctgagc gtattggtta aagtgaacg ataccgtccg    2820
ttctttcctt gtagggtttt caatcgtggg gttgagtagt gccacacagc ataaaattag   2880
cttggtttca tgctccgtta agtcatagcg actaatcgct agttcatttg ctttgaaaac   2940
aactaattca gacatacatc tcaattggtc taggtgattt taatcactat accaattgag   3000
```

| | |
|---|---|
| atgggctagt caatgataat tactagtcct tttcccggga gatctgggta tctgtaaatt | 3060 |
| ctgctagacc tttgctggaa aacttgtaaa ttctgctaga ccctctgtaa attccgctag | 3120 |
| acctttgtgt gtttttttg tttatattca agtggttata atttatagaa taaagaaaga | 3180 |
| ataaaaaaag ataaaaagaa tagatcccag ccctgtgtat aactcactac tttagtcagt | 3240 |
| tccgcagtat tacaaaagga tgtcgcaaac gctgtttgct cctctacaaa acagaccta | 3300 |
| aaaccctaaa ggcttaagta gcaccctcgc aagctcgggc aaatcgctga atattccttt | 3360 |
| tgtctccgac catcaggcac ctgagtcgct gtctttttcg tgacattcag ttcgctgcgc | 3420 |
| tcacggctct ggcagtgaat gggggtaaat ggcactacag gcgccttta tggattcatg | 3480 |
| caaggaaact acccataata caagaaaagc ccgtcacggg cttctcaggg cgttttatgg | 3540 |
| cgggtctgct atgtggtgct atctgacttt ttgctgttca gcagttcctg ccctctgatt | 3600 |
| ttccagtctg accacttcgg attatcccgt gacaggtcat tcagactggc taatgcaccc | 3660 |
| agtaaggcag cggtatcatc aacaggctta cccgtcttac tgtccctagt gcttggattc | 3720 |
| tcaccaataa aaaacgcccg gcggcaaccg agcgttctga acaaatccag atggagttct | 3780 |
| gaggtcatta ctggatctat caacaggagt ccaagcgagc tcttatttgc cgactacctt | 3840 |
| ggtgatctcg cctttcacgt agtggacaaa ttcttccaac tgatctgcgc gcgaggccaa | 3900 |
| gcgatcttct tcttgtccaa gataagcctg tctagcttca agtatgacgg gctgatactg | 3960 |
| ggccggcagg cgctccattg cccagtcggc agcgacatcc ttcggcgcga ttttgccggt | 4020 |
| tactgcgctg taccaaatgc gggacaacgt aagcactaca tttcgctcat cgccagccca | 4080 |
| gtcgggcggc gagttccata gcgttaaggt ttcatttagc gcctcaaata gatcctgttc | 4140 |
| aggaaccgga tcaaagagtt cctccgccgc tggacctacc aaggcaacgc tatgttctct | 4200 |
| tgcttttgtc agcaagatag ccagatcaat gtcgatcgtg gctggctcga agatacctgc | 4260 |
| aagaatgtca ttgcgctgcc attctccaaa ttgcagttcg cgcttagctg gataacgcca | 4320 |
| cggaatgatg tcgtcgtgca caacaatggt gacttctaca gcgcggagaa tctcgctctc | 4380 |
| tccagggaa gccgaagttt ccaaaaggtc gttgatcaaa gctcgccgcg ttgtttcatc | 4440 |
| aagccttacg gtcaccgtaa ccagcaaatc aatatcactg tgtggcttca ggccgccatc | 4500 |
| cactgcggag ccgtacaaat gtacggccag caacgtcggt tcgagatggc gctcgatgac | 4560 |
| gccaactacc tctgatagtt gagtcgatac ttcggcgatc accgcttccc tcatgatgtt | 4620 |
| taactttgtt ttagggcgac tgccctgctg cgtaacatcg ttgctgctcc ataacatcaa | 4680 |
| acatcgaccc acggcgtaac gcgcttgctg cttggatgcc cgaggcatag actgtaccc | 4740 |
| aaaaaaacag tcataacaag ccatgaaaac cgccactgcg ccgttaccac cgctgcgttc | 4800 |
| ggtcaaggtt ctggaccagt tgcgtgagcg cat | 4833 |

<210> SEQ ID NO 4
<211> LENGTH: 5563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | |
|---|---|
| ctcgagttaa ttttttaaagt atgggcaatc aattgctcct gttaaaattg ctttagaaat | 60 |
| actttggcag cggtttgttg tattgagttt catttgcgca ttggttaaat ggaaagtgac | 120 |
| agtacgctca ctgcagccta atattttga aatatcccaa gagcttttc cttcgcatgc | 180 |

-continued

```
ccacgctaaa cattcttttt ctcttttggt taaatcgttg tttgatttat tatttgctat    240
atttattttt cgataattat caactagaga aggaacaatt aatggtatgt tcatacacgc    300
atgtaaaaat aaactatcta tatagttgtc tttttctgaa tgtgcaaaac taagcattcc    360
gaagccattg ttagccgtat gaatagggaa actaaaccca gtgataagac ctgatgtttt    420
cgcttcttta attacatttg gagattttt atttacagca ttgttttcaa atatattcca    480
attaattggt gaatgattgg agttagaata atctactata ggatcatatt ttattaaatt    540
agcgtcatca taatattgcc tccattttt agggtaatta tctagaattg aaatatcaga    600
tttaaccata gaatgaggat aaatgatcgc gagtaaataa tattcacaat gtaccatttt    660
agtcatatca gataagcatt gattaatatc attattgctt ctacaagctt taattttatt    720
aattattctg tatgtgtcgt cggcatttat gttttcata cccatctctt tatccttacc    780
tattgtttgt cgcaagtttt gcgtgttata tatcattaaa acggtaatgg attgacattt    840
gattctaata aattggattt ttgtcacact attgtatcgc tgggaataca attacttaac    900
ataagcacct gtaggatcgt acaggtttac gcaagaaaat ggtttgttat agtcgaatga    960
attcattaaa gaggagaaag gtaccatgag caaaggagaa gaacttttca ctggagttgt   1020
cccaattctt gttgaattag atggtgatgt taatgggcac aaattttctg tccgtggaga   1080
gggtgaaggt gatgctacaa acggaaaact caccctaaa tttatttgca ctactggaaa   1140
actacctgtt ccgtggccaa cacttgtcac tactctgacc tatggtgttc aatgcttttc   1200
ccgttatccg gatcacatga aacggcatga cttttcaag agtgccatgc ccgaaggtta   1260
tgtacaggaa cgcactatat ctttcaaaga tgacgggacc tacaagacgc gtgctgaagt   1320
caagtttgaa ggtgataccc ttgttaatcg tatcgagtta aagggtattg attttaaaga   1380
agatggaaac attcttggac acaaactcga gtacaacttt aactcacaca atgtatacat   1440
cacggcagac aaacaaaaga atggaatcaa agctaacttc aaaattcgcc acaacgttga   1500
agatggttcc gttcaactag cagaccatta tcaacaaaat actccaattg gcgatggccc   1560 tgtccttta ccagacaacc attacctgtc gacacaatct gtcctttcga aagatcccaa   1620
cgaaaagcgt gaccacatgg tccttcttga gtttgtaact gctgctggga ttacacatgg   1680
catggatgag ctctacaaag cagcgaacga cgaaaattac gcccttgcag cgtaaaagct   1740
taattagctg atctagacgc gtgctagagg catcaaataa aacgaaaggc tcagtcgaaa   1800
gactgggcct ttcgttttat ctgttgtttg tcggtgaacg ctctcctgag taggacaaat   1860
ccgccgccct agacctaggc gtcttcacct cgagttaatt tttaaagtat gggcaatcaa   1920
ttgctcctgt taaaattgct ttagaaatac tttggcagcg gtttgttgta ttgagtttca   1980
tttgcgcatt ggttaaatgg aaagtgacag tacgctcact gcagcctaat attttttgaaa  2040 tatcccaaga gcttttcct tcgcatgccc acgctaaaca ttcttttct cttttggtta    2100 aatcgttgtt tgatttatta tttgctatat ttattttcg ataattatca actagagaag   2160
gaacaattaa tggtatgttc atacacgcat gtaaaaataa actatctata tagttgtctt   2220
tttctgaatg tgcaaaacta agcattccga agccattgtt agccgtatga atagggaaac   2280
taaacccagt gataagacct gatgttttcg cttctttaat tacatttgga gattttttat   2340
ttacagcatt gttttcaaat atattccaat taattggtga atgattggag ttagaataat   2400
ctactatagg atcatatttt attaaattag cgtcatcata atattgcctc cattttttag   2460
ggtaattatc tagaattgaa atatcagatt taaccataga atgaggataa atgatcgcga   2520
gtaaataata ttcacaatgt accattttag tcatatcaga taagcattga ttaatatcat   2580
```

```
tattgcttct acaagcttta attttattaa ttattctgta tgtgtcgtcg gcatttatgt    2640
ttttcatacc catctcttta tccttaccta ttgtttgtcg caagttttgc gtgttatata    2700
tcattaaaac ggtaatggat tgacatttga ttctaataaa ttggatttt gtcacactat     2760 tgtatcgctg ggaatacaat tacttaacat aagcacctgt aggatcgtac aggtttacgc    2820
aagaaaatgg tttgttatag tcgaatgaat tcattaaaga ggagaaaggt accatgacta    2880
taatgataaa aaaatcggat tttttggcaa ttccatcgga ggagtataaa ggtattctaa    2940
gtcttcgtta tcaagtgttt aagcaaagac ttgagtggga cttagttgta gaaaataacc    3000
ttgaatcaga tgagtatgat aactcaaatg cagaatatat ttatgcttgt gatgatactg    3060
aaaatgtaag tggatgctgg cgtttattac ctacaacagg tgattatatg ctgaaaagtg    3120 ttttcctga attgcttggt caacagagtg ctcccaaaga tcctaatata gtcgaattaa    3180
gtcgttttgc tgtaggtaaa aatagctcaa agataaataa ctctgctagt gaaattacaa    3240
tgaaactatt tgaagctata tataaacacg ctgttagtca aggtattaca gaatatgtaa    3300
cagtaacatc aacagcaata gagcgatttt taaagcgtat taaagttcct tgtcatcgta    3360
ttggagacaa agaaattcat gtattaggtg atactaaatc ggttgtattg tctatgccta    3420
ttaatgaaca gtttaaaaaa gcagtcttaa atgcagcgaa cgacgaaaat tacgcccttg    3480
cagcgtaaac gcgtgctaga ggcatcaaat aaaacgaaag gctcagtcga agactgggc     3540 ctttcgtttt atctgttgtt tgtcggtgaa cgctctcctg agtaggacaa atccgccgcc    3600
ctagacctag ggcgttcggc tgcggcgagc ggtatcagct cactcaaagg cggtaatacg    3660
gttatccaca gaatcagggg ataacgcagg aaagaacatg tgagcaaaag gccagcaaaa    3720
ggccaggaac cgtaaaaagg ccgcgttgct ggcgttttc cataggctcc gcccccctga     3780
cgagcatcac aaaaatcgac gctcaagtca gaggtggcga acccgacag gactataaag     3840 ataccaggcg tttccccctg gaagctccct cgtgcgctct cctgttccga ccctgccgct    3900
taccggatac ctgtccgcct ttctccctt gggaagcgtg gcgctttctc atagctcacg     3960
ctgtaggtat ctcagttcgg tgtaggtcgt tcgctccaag ctgggctgtg tgcacgaacc    4020
ccccgttcag cccgaccgct cgccttatc cggtaactat cgtcttgagt ccaacccggt     4080
aagacacgac ttatcgccac tggcagcagc cactggtaac aggattagca gagcgaggta    4140
tgtaggcggt gctacagagt tcttgaagtg gtggcctaac tacggctaca ctagaaggac    4200
agtatttggt atctgcgctc tgctgaagcc agttaccttc ggaaaaagag ttggtagctc    4260
ttgatccggc aaacaaacca ccgctggtag cggtggtttt tttgtttgca agcagcagat    4320
tacgcgcaga aaaaaggat ctcaagaaga tccttgatc ttttctacgg ggtctgacgc       4380
tcagtggaac gaaaactcac gttaagggat tttggtcatg actagtgctt ggattctcac    4440
caataaaaaa cgcccggcgg caaccgagcg ttctgaacaa atccagatgg agttctgagg    4500
tcattactgg atctatcaac aggagtccaa gcgagctctc gaaccccaga gtcccgctca    4560
gaagaactcg tcaagaaggc gatagaaggc gatgcgctgc gaatcgggag cggcgatacc    4620
gtaaagcacg aggaagcggt cagcccattc gccgccaagc tcttcagcaa tatcacgggt    4680
agccaacgct atgtcctgat agcggtccgc cacacccagc cggccacagt cgatgaatcc    4740
agaaaagcgg ccattttcca ccatgatatt cggcaagcag gcatcgccat gggtcacgac    4800
gagatcctcg ccgtcgggca tgcgcgcctt gagcctggcg aacagttcgg ctggcgcgag    4860
cccctgatgc tcttcgtcca gatcatcctg atcgacaaga ccggcttcca tccgagtacg    4920
```

| | |
|---|---|
| tgctcgctcg atgcgatgtt tcgcttggtg gtcgaatggg caggtagccg gatcaagcgt | 4980 |
| atgcagccgc cgcattgcat cagccatgat ggatactttc tcggcaggag caaggtgaga | 5040 |
| tgacaggaga tcctgccccg gcacttcgcc aatagcagc cagtcccttc ccgcttcagt | 5100 |
| gacaacgtcg agcacagctg cgcaaggaac gcccgtcgtg gccagccacg atagccgcgc | 5160 |
| tgcctcgtcc tgcagttcat tcagggcacc ggacaggtcg gtcttgacaa aaagaaccgg | 5220 |
| gcgcccctgc gctgacagcc ggaacacggc ggcatcagag cagccgattg tctgttgtgc | 5280 |
| ccagtcatag ccgaatagcc tctccaccca agcggccgga gaacctgcgt gcaatccatc | 5340 |
| ttgttcaatc atgcgaaacg atcctcatcc tgtctcttga tcagatcttg atcccctgcg | 5400 |
| ccatcagatc cttggcggca agaaagccat ccagtttact ttgcagggct tcccaacctt | 5460 |
| accagagggc gccccagctg gcaattccga cgtctaagaa accattatta tcatgacatt | 5520 |
| aacctataaa aataggcgta tcacgaggcc ctttcgtctt cac | 5563 |

<210> SEQ ID NO 5
<211> LENGTH: 3893
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | |
|---|---|
| ctcgagttaa tttttaaagt atgggcaatc aattgctcct gttaaaattg ctttagaaat | 60 |
| actttggcag cggtttgttg tattgagttt catttgcgca ttggttaaat ggaaagtgac | 120 |
| agtacgctca ctgcagccta atattttga aatatcccaa gagcttttc cttcgcatgc | 180 |
| ccacgctaaa cattcttttt ctcttttggt taaatcgttg tttgatttat tatttgctat | 240 |
| atttatttt cgataattat caactagaga aggaacaatt aatggtatgt tcatacacgc | 300 |
| atgtaaaaat aaactatcta tatagttgtc ttttttctgaa tgtgcaaaac taagcattcc | 360 |
| gaagccattg ttagccgtat gaatagggaa actaaaccca gtgataagac ctgatgtttt | 420 |
| cgcttcttta attacatttg gagatttttt atttacagca ttgttttcaa atatattcca | 480 |
| attaattggt gaatgattgg agttagaata atctactata ggatcatatt ttattaaatt | 540 |
| agcgtcatca taatattgcc tccatttttt agggtaatta tctagaattg aaatatcaga | 600 |
| tttaaccata gaatgaggat aaatgatcgc gagtaaataa tattcacaat gtaccatttt | 660 |
| agtcatatca gataagcatt gattaatatc attattgctt ctacaagctt taattttatt | 720 |
| aattattctg tatgtgtcgt cggcatttat gttttcata cccatctctt tatccttacc | 780 |
| tattgtttgt cgcaagtttt gcgtgttata tatcattaaa acggtaatgg attgacattt | 840 |
| gattctaata aattggattt ttgtcacact attgtatcgc tgggaataca attacttaac | 900 |
| ataagcacct gtaggatcgt acaggtttac gcaagaaaat ggtttgttat agtcgaatga | 960 |
| attcattaaa gaggagaaag gtaccatgac agtaaagaaa ctttatttca tcccagcagg | 1020 |
| tcgttgcatg ttggatcatt cgtctgttaa cagtgcgtta acaccgggga actattaaa | 1080 |
| cttgccggtg tggtgttatc ttttggagac ggaagaaggt cctatttag tagacacagg | 1140 |
| tatgccagaa agtgcagtta ataatgaagg cttttttaac ggtacatttg ttgaaggaca | 1200 |
| gatcttaccg aaaatgactg aagaagatag aatcgtgaat atattaaagc gtgtagggta | 1260 |
| tgagccggac gaccttttat atattattag ttcctcactta catttgatc atgcaggagg | 1320 |
| aaacggtgct tttacaaata caccaattat tgtgcagcga acggaatatg aggcagcact | 1380 |

```
tcatagagaa gaatatatga aagaatgtat attaccgcat ttgaactaca aaattattga    1440 agggggattat gaagtggtac caggtgttca attattgtat acgccaggtc attctccagg   1500
ccatcagtcg ctattcattg agacggagca atccggttca gtttattaa cgattgatgc    1560 atcgtacacg aaagagaatt ttgaagatga agtgccgttc gcaggatttg atccagaatt   1620
agctttatct tcaattaaac gtttaaaaga agttgtgaaa aagagaaac caattatttt    1680 ctttggtcat gatatagagc aggaaaagag ttgtagagtg ttcccggaat atatagcagc   1740
gaacgacgaa aattacgccc ttgcagcgta aacgcgtgct agaggcatca aataaaacga   1800
aaggctcagt cgaaagactg ggcctttcgt tttatctgtt gtttgtcggt gaacgctctc   1860
ctgagtagga caaatccgcc gccctagacc taggggatat attccgcttc ctcgctcact   1920
gactcgctac gctcggtcgt tcgactgcgg cgagcgaaa tggcttacga acggggcgga    1980
gatttcctgg aagatgccag gaagatactt aacagggaag tgagagggcc gcggcaaagc   2040 cgttttttcca taggctccgc cccctgaca agcatcacga aatctgacgc tcaaatcagt   2100
ggtggcgaaa cccgacagga ctataaagat accaggcgtt tcccctggc ggctccctcg    2160 tgcgctctcc tgttcctgcc tttcggttta ccggtgtcat tccgctgtta tggccgcgtt   2220
tgtctcattc cacgcctgac actcagttcc gggtaggcag ttcgctccaa gctggactgt   2280
atgcacgaac cccccgttca gtccgaccgc tgcgccttat ccggtaacta tcgtcttgag   2340 tccaaccccgg aaagacatgc aaaagcacca ctggcagcag ccactggtaa ttgatttaga   2400
ggagttagtc ttgaagtcat gcgccggtta aggctaaact gaaaggacaa gttttggtga   2460
ctgcgctcct ccaagccagt tacctcggtt caaagagttg gtagctcaga gaaccttcga   2520
aaaaccgccc tgcaaggcgg ttttttcgtt ttcagagcaa gagattacgc gcagaccaaa   2580
acgatctcaa gaagatcatc ttattaatca gataaaatat ttctagattt cagtgcaatt   2640
tatctcttca aatgtagcac ctgaagtcag ccccatacga tataagttgt tactagtgct   2700
tggattctca ccaataaaaa acgcccggcg gcaaccgagc gttctgaaca aatccagatg   2760
gagttctgag gtcattactg gatctatcaa caggagtcca agcgagctcg taaacttggt   2820
ctgacagtta ccaatgctta atcagtgagg cacctatctc agcgatctgt ctatttcgtt   2880
catccatagt tgcctgactc cccgtcgtgt agataactac gatacgggag ggcttaccat   2940
ctggccccag tgctgcaatg ataccgcgag acccacgctc accggctcca gatttatcag   3000
caataaacca gccagccgga agggccgagc gcagaagtgg tcctgcaact ttatccgcct   3060
ccatccagtc tattaattgt tgccgggaag ctagagtaag tagttcgcca gttaatagtt   3120
tgcgcaacgt tgttgccatt gctacaggca tcgtggtgtc acgctcgtcg tttggtatgg   3180
cttcattcag ctccggttcc caacgatcaa ggcgagttac atgatccccc atgttgtgca   3240
aaaaagcggt tagctccttc ggtcctccga tcgttgtcag aagtaagttg gccgcagtgt   3300
tatcactcat ggttatggca gcactgcata attctcttac tgtcatgcca tccgtaagat   3360
gcttttctgt gactggtgag tactcaacca agtcattctg agaatagtgt atgcggcgac   3420
cgagttgctc ttgcccggcg tcaatacggg ataataccgc gccacatagc agaactttaa   3480
aagtgctcat cattggaaaa cgttcttcgg ggcgaaaact ctcaaggatc ttaccgctgt   3540
tgagatccag ttcgatgtaa cccactcgtg cacccaactg atcttcagca tcttttactt   3600
tcaccagcgt ttctgggtga gcaaaaacag gaaggcaaaa tgccgcaaaa aagggaataa   3660
gggcgacacg gaaatgttga atactcatac tcttcctttt tcaatattat tgaagcattt   3720
atcagggtta ttgtctcatg agcggataca tatttgaatg tatttagaaa aataaacaaa   3780
```

| tagggggttcc gcgcacattt ccccgaaaag tgccacctga cgtctaagaa accattatta | 3840 |
| tcatgacatt aacctataaa aataggcgta tcacgaggcc ctttcgtctt cac | 3893 |

<210> SEQ ID NO 6
<211> LENGTH: 4676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| tttccaagtt atctcaccta ccttaaggta atagtgtgat taatcatatg cgttttttggt | 60 |
| tatgtgttgt ttgacttaat atcagagccg agagatactt gttttctaca aaggagaggg | 120 |
| aaatgttgca actaacacca cttcagttat ttaaaaacct gtccgatgaa acccgtttgg | 180 |
| gtatcgtgtt gttgctcagg gagatgggag agttgggcgt gtgtgacttg catggcactg | 240 |
| gatcaatcac agcccaaaat atcccgtcat ctggcgatgc tacgggaaag tggaatcctt | 300 |
| ctggatcgta aacagggaaa atgggttcac taccgcttat caccgcatat tccttcatgg | 360 |
| gctgcccaga ttattgagca ggcctggtta agccaacagg acgacgttca ggtcatcgca | 420 |
| cgcaagctgg ctcagttaac tgcccggtag cagtaaggct gtctgcatct aaaaaatttg | 480 |
| cctgaattcc aagttatcca cctaccttaa ggtaatagtg tgattcatca tatgcgtttt | 540 |
| tggttatgtg aattaatcac tagagaattc attaaagagg agaaaggtac catgactata | 600 |
| atgataaaaa aatcggattt tttggcaatt ccatcggagg agtataaagg tattctaagt | 660 |
| cttcgttatc aagtgtttaa gcaaagactt gagtgggact tagttgtaga aaataacctt | 720 |
| gaatcagatg agtatgataa ctcaaatgca gaatatattt atgcttgtga tgatactgaa | 780 |
| aatgtaagtg gatgctggcg tttattacct acaacaggtg attatatgct gaaaagtgtt | 840 |
| tttcctgaat tgcttggtca acagagtgct cccaaagatc ctaatatagt cgaattaagt | 900 |
| cgttttgctg taggtaaaaa tagctcaaag ataaataact ctgctagtga aattacaatg | 960 |
| aaactatttg aagctatata taaacacgct gttagtcaag gtattacaga atatgtaaca | 1020 |
| gtaacatcaa cagcaataga gcgatttta aagcgtatta aagttccttg tcatcgtatt | 1080 |
| ggagacaaag aaattcatgt attaggtgat actaaatcgg ttgtattgtc tatgcctatt | 1140 |
| aatgaacagt ttaaaaaagc agtcttaaat gcagcgaacg acgaaaatta cgcccttgca | 1200 |
| gcgacgcgtg ctagaggcat caaataaaac gaaaggctca gtcgaaagac tgggcctttc | 1260 |
| gttttatctg ttgtttgtcg gtgaacgctc tcctgagtag gacaaatccg ccgccctaga | 1320 |
| cctagggtac gggttttgct gcccgcaaac gggctgttct ggtgttgcta gtttgttatc | 1380 |
| agaatcgcag atccggcttc aggtttgccg gctgaaagcg ctatttcttc cagaattgcc | 1440 |
| atgatttttt ccccacggga ggcgtcactg gctcccgtgt tgtcggcagc tttgattcga | 1500 |
| taagcagcat cgcctgtttc aggctgtcta tgtgtgactt tgagctgta acaagttgtc | 1560 |
| tcaggtgttc aatttcatgt tctagttgct ttgttttact ggtttcacct gttctattag | 1620 |
| gtgttacatg ctgttcatct gttacattgt cgatctgttc atggtgaaca gctttaaatg | 1680 |
| caccaaaaac tcgtaaaagc tctgatgtat ctatcttttt tacaccgttt tcatctgtgc | 1740 |
| atatggacag ttttcccttt gatatctaac ggtgaacagt tgttctactt tgtttgtta | 1800 |
| gtcttgatgc ttcactgata gatacaagag ccataagaac ctcagatcct ccgtatttta | 1860 |
| gccagtatgt tctctagtgt ggttcgttgt ttttgcgtga gccatgagaa cgaaccattg | 1920 |

```
agatcatgct tactttgcat gtcactcaaa aattttgcct caaaactggt gagctgaatt    1980
tttgcagtta aagcatcgtg tagtgttttt cttagtccgt tacgtaggta ggaatctgat    2040
gtaatggttg ttggtatttt gtcaccattc attttatct ggttgttctc aagttcggtt    2100
acgagatcca tttgtctatc tagttcaact tggaaaatca acgtatcagt cgggcggcct    2160
cgcttatcaa ccaccaattt catattgctg taagtgttta atctttact tattggtttc    2220 aaaacccatt ggttaagcct tttaaactca tggtagttat tttcaagcat taacatgaac    2280
ttaaattcat caaggctaat ctctatattt gccttgtgag ttttcttttg tgttagttct    2340
tttaataacc actcataaat cctcatagag tatttgtttt caaaagactt aacatgttcc    2400
agattatatt ttatgaattt ttttaactgg aaaagataag gcaatatctc ttcactaaaa    2460
actaattcta attttttcgct tgagaacttg gcatagtttg tccactggaa aatctcaaag    2520
cctttaacca aaggattcct gatttccaca gttctcgtca tcagctctct ggttgcttta    2580
gctaatacac cataagcatt tccctactg atgttcatca tctgagcgta ttggttataa    2640
gtgaacgata ccgtccgttc tttccttgta gggttttcaa tcgtggggtt gagtagtgcc    2700
acacagcata aaattagctt ggtttcatgc tccgttaagt catagcgact aatcgctagt    2760
tcatttgctt tgaaaacaac taattcagac atacatctca attggtctag gtgattttaa    2820
tcactatacc aattgagatg ggctagtcaa tgataattac tagtcctttt cccgggagat    2880
ctgggtatct gtaaattctg ctagacccttt gctggaaaac ttgtaaattc tgctagaccc    2940
tctgtaaatt ccgctagacc tttgtgtgtt ttttttgttt atattcaagt ggttataatt    3000
tatagaataa agaaagaata aaaaagata aaaagaatag atcccagccc tgtgtataac    3060
tcactacttt agtcagttcc gcagtattac aaaaggatgt cgcaaacgct gtttgctcct    3120
ctacaaaaca gaccttaaaa ccctaaaggc ttaagtagca ccctcgcaag ctcgggcaaa    3180
tcgctgaata ttcctttttgt ctccgaccat caggcacctg agtcgctgtc tttttcgtga    3240
cattcagttc gctgcgctca cggctctggc agtgaatggg ggtaaatggc actacaggcg    3300
ccttttatgg attcatgcaa ggaaactacc cataatacaa gaaaagcccg tcacgggctt    3360
ctcagggcgt tttatggcgg gtctgctatg tggtgctatc tgacttttttg ctgttcagca    3420 gttcctgccc tctgattttc cagtctgacc acttcggatt atcccgtgac aggtcattca    3480
gactggctaa tgcacccagt aaggcagcgg tatcatcaac aggcttaccc gtcttactgt    3540
ccctagtgct tggattctca ccaataaaaa acgcccggcg gcaaccgagc gttctgaaca    3600
aatccagatg gagttctgag gtcattactg gatctatcaa caggagtcca agcgagctct    3660
tatttgccga ctaccttggt gatctcgcct ttcacgtagt ggacaaattc ttccaactga    3720 tctgcgcgcag aggccaagcg atcttcttct tgtccaagat aagcctgtct agcttcaagt    3780
atgacgggct gatactgggc cggcaggcgc tccattgccc agtcggcagc gacatccttc    3840
ggcgcgattt tgccggttac tgcgctgtac caaatgcggg acaacgtaag cactacattt    3900
cgctcatcgc cagcccagtc gggcggcgag ttccatagcg ttaaggtttc atttagcgcc    3960
tcaaatagat cctgttcagg aaccggatca aagagttcct ccgccgctgg acctaccaag    4020
gcaacgctat gttctcttgc ttttgtcagc aagatagcca gatcaatgtc gatcgtggct    4080
ggctcgaaga tacctgcaag aatgtcattg cgctgccatt ctccaaattg cagttcgcgc    4140
ttagctggat aacgccacgg aatgatgtcg tcgtgcacaa caatggtgac ttctacagcg    4200
cggagaatct cgctctctcc aggggaagcc gaagtttcca aaaggtcgtt gatcaaagct    4260
```

```
cgccgcgttg tttcatcaag ccttacggtc accgtaacca gcaaatcaat atcactgtgt    4320
ggcttcaggc cgccatccac tgcggagccg tacaaatgta cggccagcaa cgtcggttcg    4380
agatggcgct cgatgacgcc aactacctct gatagttgag tcgatacttc ggcgatcacc    4440
gcttccctca tgatgtttaa cttttgtttta gggcgactgc cctgctgcgt aacatcgttg    4500
ctgctccata acatcaaaca tcgacccacg gcgtaacgcg cttgctgctt ggatgcccga    4560
ggcatagact gtaccccaaa aaacagtca taacaagcca tgaaaaccgc cactgcgccg    4620
ttaccaccgc tgcgttcggt caaggttctg gaccagttgc gtgagcgcat gacgtc    4676
```

<210> SEQ ID NO 7
<211> LENGTH: 4258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gacgtccata tacattaact ctggaggaaa ctgttatgaa aaacataaat gccgacgaca      60
catacagaat aattaataaa attaaagctt gtagaagcaa taatgatatt aatcaatgct     120
tatctgatat gactaaaatg gtacattgtg aatattattt actcgcgatc atttatcctc     180
attctatggt taaatctgat atttcaattc tagataatta ccctaaaaaa tggaggcaat     240
attatgatga cgctaattta ataaaatatg atcctatagt agattattct aactccaatc     300
attcaccaat taattggaat atatttgaaa acaatgctgt aaataaaaaa tctccaaatg     360
taattaaaga agcgaaaaca tcaggtctta tcactgggtt tagtttccct attcatacgg     420
ctaacaatgg cttcggaatg cttagttttg cacattcaga aaaagacaac tatatagata     480
gtttattttt acatgcgtgt atgaacatac cattaattgt tccttctcta gttgataatt     540
atcgaaaaat aaatatagca ataataaat caaacaacga tttaaccaaa agagaaaaag     600
aatgtttagc gtgggcatgc gaaggaaaaa gctcttggga tatttcaaaa atattaggct     660
gcagtgagcg tactgtcact ttccatttaa ccaatgcgca aatgaaactc aatacaacaa     720
accgctgcca aagtatttct aaagcaattt taacaggagc aattgattgc ccatacttta     780
aaaattaaac gcgtgctaga ggcatcaaat aaaacgaaag gctcagtcga agactgggc     840 ctttcgtttt atctgttgtt tgtcggtgaa cgctctcctg agtaggacaa atccgccgcc     900
ctagacctag gacagtaag acgggtaagc ctgttgatga taccgctgcc ttactgggtg     960
cattagccag tctgaatgac ctgtcacggg ataatccgaa gtggtcagac tggaaaatca    1020
gagggcagga actgctgaac agcaaaaagt cagatagcac cacatagcag acccgccata    1080
aaacgccctg agaagcccgt gacgggcttt tcttgtatta tgggtagttt ccttgcatga    1140
atccataaaa ggcgcctgta gtgccattta cccccattca ctgccagagc cgtgagcgca    1200
gcgaactgaa tgtcacgaaa aagacagcga ctcaggtgcc tgatggtcgg agacaaaagg    1260
aatattcagc gatttgcccg agcttgcgag ggtgctactt aagcctttag ggttttaagg    1320
tctgttttgt agaggagcaa acagcgtttt cgacatcctt ttgtaatact gcggaactga    1380
ctaaagtagt gagttataca cagggctggg atctattctt tttatctttt tttattcttt    1440
cttattccta taattataa ccacttgaat ataaacaaaa aaacacaca aaggtctagc    1500 ggaatttaca gagggtctag cagaatttac aagttttcca gcaaaggtct agcagaattt    1560 acagatatccc acaactcaaa ggaaaaggac aagtaattat cattgactag cccatctcaa    1620
```

```
ttggtatagt gattaaaatc acctagacca attgagatgt atgtctgaat tagttgtttt   1680
caaagcaaat gaactagcga ttagtcgcta tgacttaacg gagcatgaaa ccaagctaat   1740
tttatgctgt gtggcactac tcaaccccac gattgaaaac cctacaagga agaacggac    1800 ggtatcgttc acttataacc aatacgctca gatgatgaac atcagtaggg aaaatgctta   1860
tggtgtatta gctaaagcaa ccagagagct gatgacgaga actgtggaaa tcaggaatcc   1920
tttggttaaa ggctttaaga ttttccagtg acaaactat  gccaagttct caagcgaaaa   1980
attagaatta gttttagtg  aagagatatt gccttatctt ttccagttaa aaaaattcat   2040
aaaatataat ctggaacatg ttaagtcttt tgaaaacaaa tactctatga ggatttatga   2100
gtggttatta aaagaactaa cacaaaagaa aactcacaag gcaaatatag agattagcct   2160
tgatgaattt aagttcatgt taatgcttga aaataactac catgagttta aaaggcttaa   2220
ccaatgggtt ttgaaaccaa taagtaaaga tttaaacact tacagcaata tgaaattggt   2280
ggttgataag cgaggccgcc cgactgatac gttgattttc caagttgaac tagatagaca   2340
aatggatctc gtaaccgaac ttgagaacaa ccagataaaa atgaatggtg acaaaatacc   2400
aacaaccatt acatcagatt cctacctacg taacggacta agaaaaacac tacacgatgc   2460
tttaactgca aaaattcagc tcaccagttt tgaggcaaaa tttttgagtg acatgcaaag   2520
taagcatgat ctcaatggtt cgttctcatg gctcacgcaa aaacaacgaa ccacactaga   2580
gaacatactg gctaaatacg aaggatctg  aggttcttat ggctcttgta tctatcagtg   2640
aagcatcaag actaacaaac aaaagtagaa caactgttca ccgttagata tcaaagggaa   2700
aactgtccat atgcacagat gaaaacggtg taaaaaagat agatacatca gagcttttac   2760 gagttttgg  tgcatttaaa gctgttcacc atgaacagat cgacaatgta acagatgaac   2820
agcatgtaac acctaataga acaggtgaaa ccagtaaaac aaagcaacta gaacatgaaa   2880
ttgaacacct gagacaactt gttacagctc aacagtcaca catagacagc ctgaaacagg   2940
cgatgctgct tatcgaatca agctgccga  caacacggga gccagtgacg cctcccgtgg   3000
ggaaaaaatc atggcaattc tggaagaaat agcgctttca gccggcaaac cggctgaagc   3060
cggatctgcg attctgataa caaactagca acaccagaac agcccgtttg cgggcagcaa   3120
aacccgtaca ctagtgcttg gattctcacc aataaaaaac gcccggcggc aaccgagcgt   3180
tctgaacaaa tccagatgga gttctgaggt cattactgga tctatcaaca ggagtccaag   3240
cgagctctta tttgccgact accttggtga tctcgccttt cacgtagtgg acaaattctt   3300
ccaactgatc tgcgcgcgag gccaagcgat cttcttcttg tccaagataa gcctgtctag   3360
cttcaagtat gacgggctga tactgggccg gcaggcgctc cattgcccag tcggcagcga   3420
catccttcgg cgcgattttg ccggttactg cgctgtacca aatgcgggac aacgtaagca   3480
ctacatttcg ctcatcgcca gcccagtcgg gcggcgagtt ccatagcgtt aaggtttcat   3540
ttagcgcctc aaatagatcc tgttcaggaa ccggatcaaa gagttcctcc gccgctggac   3600
ctaccaaggc aacgctatgt tctcttgctt ttgtcagcaa gatagccaga tcaatgtcga   3660
tcgtggctgg ctcgaagata cctgcaagaa tgtcattgcg ctgccattct ccaaattgca   3720
gttcgcgctt agctggataa cgccacggaa tgatgtcgtc gtgcacaaca atggtgactt   3780
ctacagcgcg gagaatctcg ctctctccag gggaagccga gtttccaaa  aggtcgttga   3840 tcaaagctcg ccgcgttgtt tcatcaagcc ttacggtcac cgtaaccagc aaatcaatat   3900
cactgtgtgc cttcaggccg ccatccactg cggagccgta caaatgtacg ccagcaacg   3960 tcggttcgag atggcgctcg atgacgccaa ctacctctga tagttgagtc gatacttcgg   4020
```

| cgatcaccgc ttccctcatg atgtttaact ttgttttagg gcgactgccc tgctgcgtaa | 4080 |
| catcgttgct gctccataac atcaaacatc gacccacggc gtaacgcgct tgctgcttgg | 4140 |
| atgcccgagg catagactgt accccaaaaa aacagtcata acaagccatg aaaaccgcca | 4200 |
| ctgcgccgtt accaccgctg cgttcggtca aggttctgga ccagttgcgt gagcgcat   | 4258 |

```
<210> SEQ ID NO 8
<211> LENGTH: 4260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

| gacgtcttga ctctgtagtt gctacagggt gtgcaatatg aaaaacataa atgccgacga | 60 |
| cacatacaga ataattaata aaattaaagc ttgtagaagc aataatgata ttaatcaatg | 120 |
| cttatctgat atgactaaaa tggtacattg tgaatattat ttactcgcga tcatttatcc | 180 |
| tcattctatg gttaaatctg atatttcaat tctagataat taccctaaaa aatggaggca | 240 |
| atattatgat gacgctaatt taataaaata tgatcctata gtagattatt ctaactccaa | 300 |
| tcattcacca attaattgga atatatttga aaacaatgct gtaaataaaa aatctccaaa | 360 |
| tgtaattaaa gaagcgaaaa catcaggtct tatcactggg tttagtttcc ctattcatac | 420 |
| ggctaacaat ggcttcggaa tgcttagttt tgcacattca gaaaaagaca actatataga | 480 |
| tagtttattt ttacatgcgt gtatgaacat accattaatt gttccttctc tagttgataa | 540 |
| ttatcgaaaa ataaatatag caaataataa atcaaacaac gatttaacca aaagagaaaa | 600 |
| agaatgttta gcgtgggcat gcgaaggaaa aagctcttgg gatatttcaa aaatattagg | 660 |
| ctgcagtgag cgtactgtca ctttccattt aaccaatgcg caaatgaaac tcaatacaac | 720 |
| aaaccgctgc caaagtattt ctaaagcaat tttaacagga gcaattgatt gcccatactt | 780 |
| taaaaattaa acgcgtgcta gaggcatcaa ataaaacgaa aggctcagtc gaaagactgg | 840 |
| gcctttcgtt ttatctgttg tttgtcggtg aacgctctcc tgagtaggac aaatccgccg | 900 |
| ccctagacct agggacagta agacgggtaa gcctgttgat gataccgctg ccttactggg | 960 |
| tgcattagcc agtctgaatg acctgtcacg ggataatccg aagtggtcag actggaaaat | 1020 |
| cagagggcag gaactgctga acagcaaaaa gtcagatagc accacatagc agacccgcca | 1080 |
| taaaacgccc tgagaagccc gtgacgggct tttcttgtat tatgggtagt ttccttgcat | 1140 |
| gaatccataa aaggcgcctg tagtgccatt taccccatt cactgccaga gccgtgagcg | 1200 |
| cagcgaactg aatgtcacga aaagacagc gactcaggtg cctgatggtc ggagacaaaa | 1260 |
| ggaatattca gcgatttgcc cgagcttgcg agggtgctac ttaagccttt agggttttaa | 1320 |
| ggtctgtttt gtagaggagc aaacagcgtt tgcgacatcc ttttgtaata ctgcggaact | 1380 |
| gactaaagta gtgagttata cacagggctg ggatctattc tttttatctt tttttattct | 1440 |
| ttctttattc tataaattat aaccacttga atataaacaa aaaaaacaca caaaggtcta | 1500 |
| gcggaattta cagagggtct agcagaattt acagttttc cagcaaaggt ctagcagaat | 1560 |
| ttacagatac ccacaactca aaggaaaagg acaagtaatt atcattgact agcccatctc | 1620 |
| aattggtata gtgattaaaa tcacctagac caattgagat gtatgtctga attagttgtt | 1680 |
| ttcaaagcaa atgaactagc gattagtcgc tatgacttaa cggagcatga aaccaagcta | 1740 |
| attttatgct gtgtggcact actcaacccc acgattgaaa accctacaag gaaagaacgg | 1800 |

```
acggtatcgt tcacttataa ccaatacgct cagatgatga acatcagtag ggaaaatgct   1860
tatggtgtat tagctaaagc aaccagagag ctgatgacga gaactgtgga aatcaggaat   1920
cctttggtta aaggctttaa gattttccag tggacaaact atgccaagtt ctcaagcgaa   1980
aaattagaat tagtttttag tgaagagata ttgccttatc ttttccagtt aaaaaaattc   2040
ataaaatata atctggaaca tgttaagtct tttgaaaaca aatactctat gaggatttat   2100
gagtggttat taaagaact aacacaaaag aaaactcaca aggcaaatat agagattagc   2160
cttgatgaat ttaagttcat gttaatgctt gaaaataact accatgagtt taaaaggctt   2220
aaccaatggg ttttgaaacc aataagtaaa gatttaaaca cttacagcaa tatgaaattg   2280
gtggttgata agcgaggccg cccgactgat acgttgattt tccaagttga actagataga   2340
caaatggatc tcgtaaccga acttgagaac aaccagataa aaatgaatgg tgacaaaata   2400
ccaacaacca ttacatcaga ttcctaccta cgtaacggac taagaaaaac actacacgat   2460
gctttaactg caaaaattca gctcaccagt tttgaggcaa aatttttgag tgacatgcaa   2520
agtaagcatg atctcaatgg ttcgttctca tggctcacgc aaaaacaacg aaccacacta   2580
gagaacatac tggctaaata cggaaggatc tgaggttctt atggctcttg tatctatcag   2640
tgaagcatca agactaacaa acaaaagtag aacaactgtt caccgttaga tatcaaaggg   2700
aaaactgtcc atatgcacag atgaaaacgg tgtaaaaaag atagatacat cagagctttt   2760
acgagttttt ggtgcattta aagctgttca ccatgaacag atcgacaatg taacagatga   2820
acagcatgta acacctaata gaacaggtga aaccagtaaa acaaagcaac tagaacatga   2880
aattgaacac ctgagacaac ttgttacagc tcaacagtca cacatagaca gcctgaaaca   2940
ggcgatgctg cttatcgaat caaagctgcc gacaacacgg gagccagtga cgcctcccgt   3000
ggggaaaaaa tcatggcaat tctggaagaa atagcgcttt cagccggcaa accggctgaa   3060
gccggatctg cgattctgat aacaaactag caacaccaga acagcccgtt tgcgggcagc   3120
aaaacccgta cactagtgct tggattctca ccaataaaaa acgcccggcg caaccgagc   3180 gttctgaaca atccagatg gagttctgag gtcattactg gatctatcaa caggagtcca   3240
agcgagctct tatttgccga ctaccttggt gatctcgcct ttcacgtagt ggacaaattc   3300
ttccaactga tctgcgcgcg aggccaagcg atcttcttct tgtccaagat aagcctgtct   3360
agcttcaagt atgacgggct gatactgggc cggcaggcgc tccattgccc agtcggcagc   3420
gacatccttc ggcgcgattt tgccggttac tgcgctgtac caaatgcggg acaacgtaag   3480
cactacattt cgctcatcgc cagcccagtc gggcggcgag ttccatagcg ttaaggtttc   3540
atttagcgcc tcaaatagat cctgttcagg aaccggatca agagttcct ccgccgctgg   3600 acctaccaag gcaacgctat gttctcttgc ttttgtcagc aagatagcca gatcaatgtc   3660
gatcgtggct ggctcgaaga tacctgcaag aatgtcattg cgctgccatt ctccaaattg   3720
cagttcgcgc ttagctggat aacgccacgg aatgatgtcg tcgtgcacaa caatggtgac   3780
ttctacagcg cggagaatct cgctctctcc aggggaagcc gaagtttcca aaaggtcgtt   3840
gatcaaagct cgccgcgttg tttcatcaag ccttacggtc accgtaacca gcaaatcaat   3900
atcactgtgt ggcttcaggc cgccatccac tgcgagccg tacaaatgta cggccagcaa   3960
cgtcggttcg agatggcgct cgatgacgcc aactacctct gatagttgag tcgatacttc   4020
ggcgatcacc gcttccctca tgatgtttaa ctttgtttta gggcgactgc cctgctgcgt   4080
aacatcgttg ctgctccata acatcaaaca tcgacccacg gcgtaacgcg cttgctgctt   4140
```

```
ggatgcccga ggcatagact gtaccccaaa aaaacagtca taacaagcca tgaaaaccgc    4200
cactgcgccg ttaccaccgc tgcgttcggt caaggttctg gaccagttgc gtgagcgcat    4260

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caattactta acataagc                                                    18

<210> SEQ ID NO 10
<211> LENGTH: 4114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
catatacatt aactctggag gaaactgtta tgactataat gataaaaaaa tcggattttt      60
tggcaattcc atcggaggag tataaaggta ttctaagtct tcgttatcaa gtgtttaagc    120
aaagacttga gtgggactta gttgtagaaa ataaccttga atcagatgag tatgataact    180
caaatgcaga atatatttat gcttgtgatg atactgaaaa tgtaagtgga tgctggcgtt    240
tattacctac aacaggtgat tatatgctga aaagtgtttt tcctgaattg cttggtcaac    300
agagtgctcc caaagatcct aatatagtcg aattaagtcg ttttgctgta ggtaaaaata    360
gctcaaagat aaataactct gctagtgaaa ttacaatgaa actatttgaa gctatatata    420
aacacgctgt tagtcaaggt attacagaat atgtaacagt aacatcaaca gcaatagagc    480
gatttttaaa gcgtattaaa gttccttgtc atcgtattgg agacaaagaa attcatgtat    540
taggtgatac taaatcggtt gtattgtcta tgcctattaa tgaacagttt aaaaaagcag    600
tcttaaatgc agcgaacgac gaaaattacg cccttgcagc gacgcgtgct agaggcatca    660
aataaaacga aggctcagt cgaaagactg ggcctttcgt tttatctgtt gtttgtcggt    720
gaacgctctc ctgagtagga caaatccgcc gccctagacc tagggtacgg gttttgctgc    780
ccgcaaacgg gctgttctgg tgttgctagt ttgttatcag aatcgcagat ccggcttcag    840
gtttgccggc tgaaagcgct atttcttcca gaattgccat gatttttcc ccacgggagg    900 cgtcactggc tcccgtgttg tcggcagctt tgattcgata agcagcatcg cctgtttcag    960
gctgtctatg tgtgactgtt gagctgtaac aagttgtctc aggtgttcaa tttcatgttc   1020
tagttgcttt gttttactgg tttcacctgt tctattaggt gttacatgct gttcatctgt   1080
tacattgtcg atctgttcat ggtgaacagc tttaaatgca ccaaaaactc gtaaagctc    1140 tgatgtatct atcttttta caccgttttc atctgtgcat atggacagtt ttccctttga   1200
tatctaacgg tgaacagttg ttctactttt gtttgttagt cttgatgctt cactgataga   1260
tacaagagcc ataagaacct cagatccttc cgtatttagc cagtatgttc tctagtgtgg   1320
ttcgttgttt ttgcgtgagc catgagaacg aaccattgag atcatgctta ctttgcatgt   1380
cactcaaaaa ttttgcctca aaactggtga gctgaatttt tgcagttaaa gcatcgtgta   1440
gtgtttttct tagtccgtta cgtaggtagg aatctgatga aatggttgtt ggtatttgt    1500 caccattcat ttttatctgg ttgttctcaa gttcggttac gagatccatt tgtctatcta   1560
```

```
gttcaacttg gaaaatcaac gtatcagtcg ggcggcctcg cttatcaacc accaatttca   1620
tattgctgta agtgtttaaa tctttactta ttggtttcaa aacccattgg ttaagccttt   1680
taaactcatg gtagttattt tcaagcatta acatgaactt aaattcatca aggctaatct   1740
ctatatttgc cttgtgagtt ttcttttgtg ttagttcttt taataaccac tcataaatcc   1800
tcatagagta tttgttttca aaagacttaa catgttccag attatatttt atgaatttt    1860 ttaactggaa aagataaggc aatatctctt cactaaaaac taattctaat ttttcgcttg   1920
agaacttggc atagtttgtc cactggaaaa tctcaaagcc tttaaccaaa ggattcctga   1980
tttccacagt tctcgtcatc agctctctgg ttgctttagc taatacacca taagcatttt   2040
ccctactgat gttcatcatc tgagcgtatt ggttataagt gaacgatacc gtccgttctt   2100
tccttgtagg gttttcaatc gtggggttga gtagtgccac acagcataaa attagcttgg   2160
tttcatgctc cgttaagtca tagcgactaa tcgctagttc atttgctttg aaaacaacta   2220
attcagacat acatctcaat tggtctaggt gattttaatc actataccaa ttgagatggg   2280
ctagtcaatg ataattacta gtccttttcc cgggagatct gggtatctgt aaattctgct   2340
agacctttgc tggaaaactt gtaaattctg ctagaccctc tgtaaattcc gctagacctt   2400
tgtgtgtttt ttttgtttat attcaagtgg ttataattta tagaataaag aaagaataaa   2460
aaaagataaa aagaatagat cccagccctg tgtataactc actactttag tcagttccgc   2520
agtattacaa aaggatgtcg caaacgctgt ttgctcctct acaaaacaga ccttaaaacc   2580
ctaaaggctt aagtagcacc ctcgcaagct cgggcaaatc gctgaatatt ccttttgtct   2640
ccgaccatca ggcacctgag tcgctgtctt tttcgtgaca ttcagttcgc tgcgctcacg   2700
gctctggcag tgaatggggg taaatggcac tacaggcgcc ttttatggat tcatgcaagg   2760
aaactaccca taatacaaga aaagcccgtc acgggcttct cagggcgttt tatggcgggt   2820
ctgctatgtg gtgctatctg acttttgct gttcagcagt tcctgccctc tgattttcca   2880
gtctgaccac ttcggattat cccgtgacag gtcattcaga ctggctaatg cacccagtaa   2940
ggcagcggta tcatcaacag gcttacccgt cttactgtcc ctagtgcttg gattctcacc   3000
aataaaaaac gcccggcggc aaccgagcgt tctgaacaaa tccagatgga gttctgaggt   3060
cattactgga tctatcaaca ggagtccaag cgagctctta tttgccgact accttggtga   3120
tctcgccttt cacgtagtgg acaaattctt ccaactgatc tgcgcgcgag ccaagcgat    3180 cttcttcttg tccaagataa gcctgtctag cttcaagtat gacgggctga tactgggccg   3240
gcaggcgctc cattgcccag tcggcagcga catccttcgg cgcgattttg ccggttactg   3300
cgctgtacca aatgcgggac aacgtaagca ctacatttcg ctcatcgcca gcccagtcgg   3360
gcggcgagtt ccatagcgtt aaggtttcat ttagcgcctc aaatagatcc tgttcaggaa   3420
ccggatcaaa gagttcctcc gccgctggac ctaccaaggc aacgctatgt tctcttgctt   3480
ttgtcagcaa gatagccaga tcaatgtcga tcgtggctgg ctcgaagata cctgcaagaa   3540
tgtcattgcg ctgccattct ccaaattgca gttcgcgctt agctggataa cgccacggaa   3600
tgatgtcgtc gtgcacaaca atggtgactt ctacagcgcg gagaatctcg ctctctccag   3660
gggaagccga agtttccaaa aggtcgttga tcaaagctcg ccgcgttgtt tcatcaagcc   3720
ttacggtcac cgtaaccagc aaatcaatat cactgtgtgg cttcaggccg ccatccactg   3780
cggagccgta caaatgtacg gccagcaacg tcggttcgag atggcgctcg atgacgccaa   3840
ctacctctga tagttgagtc gatacttcgg cgatcaccgc ttccctcatg atgtttaact   3900
```

| | |
|---|---|
| ttgttttagg gcgactgccc tgctgcgtaa catcgttgct gctccataac atcaaacatc | 3960 |
| gacccacggc gtaacgcgct tgctgcttgg atgcccgagg catagactgt accccaaaaa | 4020 |
| aacagtcata acaagccatg aaaaccgcca ctgcgccgtt accaccgctg cgttcggtca | 4080 |
| aggttctgga ccagttgcgt gagcgcatga cgtc | 4114 |

<210> SEQ ID NO 11
<211> LENGTH: 4116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---|
| ttgactctgt agttgctaca gggtgtgcaa tatgactata atgataaaaa aatcggattt | 60 |
| tttggcaatt ccatcggagg agtataaagg tattctaagt cttcgttatc aagtgtttaa | 120 |
| gcaaagactt gagtgggact tagttgtaga aaataacctt gaatcagatg agtatgataa | 180 |
| ctcaaatgca gaatatattt atgcttgtga tgatactgaa aatgtaagtg gatgctggcg | 240 |
| tttattacct acaacaggtg attatatgct gaaaagtgtt tttcctgaat tgcttggtca | 300 |
| acagagtgct cccaaagatc taatatagt cgaattaagt cgttttgctg taggtaaaaa | 360 |
| tagctcaaag ataaataact ctgctagtga aattacaatg aaactatttg aagctatata | 420 |
| taaacacgct gttagtcaag gtattacaga atatgtaaca gtaacatcaa cagcaataga | 480 |
| gcgatttta aagcgtatta aagttccttg tcatcgtatt ggagacaaag aaattcatgt | 540 |
| attaggtgat actaaatcgg ttgtattgtc tatgcctatt aatgaacagt ttaaaaaagc | 600 |
| agtcttaaat gcagcgaacg acgaaaatta cgcccttgca gcgacgcgtg ctagaggcat | 660 |
| caaataaaac gaaaggctca gtcgaaagac tgggcctttc gttttatctg ttgtttgtcg | 720 |
| gtgaacgctc tcctgagtag acaaatccg ccgccctaga cctagggtac gggttttgct | 780 |
| gcccgcaaac gggctgttct ggtgttgcta gtttgttatc agaatcgcag atccggcttc | 840 |
| aggtttgccg gctgaaagcg ctatttcttc cagaattgcc atgatttttt ccccacggga | 900 |
| ggcgtcactg gctcccgtgt tgtcggcagc tttgattcga taagcagcat cgcctgtttc | 960 |
| aggctgtcta tgtgtgactg ttgagctgta acaagttgtc tcaggtgttc aatttcatgt | 1020 |
| tctagttgct ttgttttact ggtttcacct gttctattag gtgttacatg ctgttcatct | 1080 |
| gttacattgt cgatctgttc atggtgaaca gctttaaatg caccaaaaac tcgtaaaagc | 1140 |
| tctgatgtat ctatcttttt tacaccgttt tcatctgtgc atatgacag ttttcccttt | 1200 |
| gatatctaac ggtgaacagt tgttctactt tgtttgtta gtcttgatgc ttcactgata | 1260 |
| gatacaagag ccataagaac ctcagatcct tccgtattta gccagtatgt tctctagtgt | 1320 |
| ggttcgttgt ttttgcgtga gccatgagaa cgaaccattg agatcatgct actttgcat | 1380 |
| gtcactcaaa aattttgcct caaaactggt gagctgaatt tttgcagtta aagcatcgtg | 1440 |
| tagtgttttt cttagtccgt tacgtaggta ggaatctgat gtaatggttg ttggtatttt | 1500 |
| gtcaccattc atttttatct ggttgttctc aagttcggtt acgagatcca tttgtctatc | 1560 |
| tagttcaact tggaaaatca acgtatcagt cgggcggcct cgcttatcaa ccaccaattt | 1620 |
| catattgctg taagtgttta aatctttact tattggtttc aaaacccatt ggttaagcct | 1680 |
| tttaaactca tggtagttat tttcaagcat taacatgaac ttaaattcat caaggctaat | 1740 |
| ctctatattt gccttgtgag ttttcttttg tgttagttct tttaataacc actcataaat | 1800 |

-continued

```
cctcatagag tatttgtttt caaaagactt aacatgttcc agattatatt ttatgaattt      1860
ttttaactgg aaaagataag gcaatatctc ttcactaaaa actaattcta atttttcgct      1920
tgagaacttg gcatagtttg tccactggaa aatctcaaag cctttaacca aaggattcct      1980
gatttccaca gttctcgtca tcagctctct ggttgcttta gctaatacac cataagcatt      2040
ttccctactg atgttcatca tctgagcgta ttggttataa gtgaacgata ccgtccgttc      2100
tttccttgta gggttttcaa tcgtggggtt gagtagtgcc acacagcata aaattagctt      2160
ggtttcatgc tccgttaagt catagcgact aatcgctagt tcatttgctt tgaaaacaac      2220
taattcagac atacatctca attggtctag gtgattttaa tcactatacc aattgagatg      2280
ggctagtcaa tgataattac tagtccttt cccgggagat ctgggtatct gtaaattctg       2340
ctagaccttt gctggaaaac ttgtaaattc tgctagaccc tctgtaaatt ccgctagacc      2400
tttgtgtgtt ttttttgttt atattcaagt ggttataatt tatagaataa agaaagaata      2460
aaaaaagata aaaagaatag atcccagccc tgtgtataac tcactacttt agtcagttcc      2520
gcagtattac aaaaggatgt cgcaaacgct gtttgctcct ctacaaaaca gacccttaaaa     2580 ccctaaaggc ttaagtagca ccctcgcaag ctcgggcaaa tcgctgaata ttccttttgt     2640
ctccgaccat caggcacctg agtcgctgtc tttttcgtga cattcagttc gctgcgctca     2700
cggctctggc agtgaatggg ggtaaatggc actacaggcg ccttttatgg attcatgcaa     2760
ggaaactacc cataatacaa gaaaagcccg tcacgggctt ctcagggcgt tttatgcgg      2820 gtctgctatg tggtgctatc tgactttttg ctgttcagca gttcctgccc tctgatttc     2880 cagtctgacc acttcggatt atcccgtgac aggtcattca gactggctaa tgcacccagt     2940
aaggcagcgg tatcatcaac aggcttaccc gtcttactgt ccctagtgct tggattctca     3000
ccaataaaaa acgcccggcg gcaaccgagc gttctgaaca atccagatg gagttctgag      3060 gtcattactg gatctatcaa caggagtcca agcgagctct tatttgccga ctaccttggt     3120
gatctcgcct ttcacgtagt ggacaaattc ttccaactga tctgcgcgcg aggccaagcg     3180
atcttcttct tgtccaagat aagcctgtct agcttcaagt atgacgggct gatactgggc     3240
cggcaggcgc tccattgccc agtcggcagc gacatccttc ggcgcgattt tgccggttac     3300
tgcgctgtac caaatgcggg acaacgtaag cactacattt cgctcatcgc cagcccagtc     3360
gggcggcgag ttccatagcg ttaaggtttc atttagcgcc tcaaatagat cctgttcagg     3420
aaccggatca aagagttcct ccgccgctgg acctaccaag gcaacgctat gttctcttgc     3480
ttttgtcagc aagatagcca gatcaatgtc gatcgtggct ggctcgaaga tacctgcaag     3540
aatgtcattg cgctgccatt ctccaaattg cagttcgcgc ttagctggat aacgccacgg     3600
aatgatgtcg tcgtgcacaa caatggtgac ttctacagcg cggagaatct cgctctctcc     3660
aggggaagcc gaagtttcca aaaggtcgtt gatcaaagct cgccgcgttg tttcatcaag     3720
ccttacggtc accgtaacca gcaaatcaat atcactgtgt ggcttcaggc cgccatccac     3780
tgcggagccg tacaaatgta cggccagcaa cgtcggttcg agatggcgct cgatgacgcc     3840
aactacctct gatagttgag tcgatacttc ggcgatcacc gcttccctca tgatgtttaa     3900
ctttgtttta gggcgactgc cctgctgcgt aacatcgttg ctgctccata acatcaaaca     3960
tcgacccacg gcgtaacgcg cttgctgctt ggatgcccga ggcatagact gtaccccaaa     4020
aaaacagtca taacaagcca tgaaaaccgc cactgcgccg ttaccaccgc tgcgttcggt     4080
caaggttctg gaccagttgc gtgagcgcat gacgtc                               4116
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Asn Asp Glu Asn Tyr Ala Leu Ala Ala
1               5                   10
```